US007235244B2

(12) United States Patent
Howley et al.

(10) Patent No.: US 7,235,244 B2
(45) Date of Patent: Jun. 26, 2007

(54) COMPOSITIONS AND METHODS FOR TREATING PAPILLOMAVIRUS-INFECTED CELLS

(75) Inventors: Peter M. Howley, Wellesley, MA (US); John Benson, Brookline, MA (US); Hiroaki Kasukawa, Princeton, NJ (US)

(73) Assignee: President and Fellows of Harvard College, Cambridge, MA (US)

( * ) Notice: Subject to any disclaimer, the term of this patent is extended or adjusted under 35 U.S.C. 154(b) by 203 days.

(21) Appl. No.: 10/744,964

(22) Filed: Dec. 23, 2003

(65) Prior Publication Data

US 2005/0085411 A1 Apr. 21, 2005

Related U.S. Application Data

(63) Continuation of application No. 10/161,499, filed on Jun. 3, 2002, now Pat. No. 6,673,354, which is a continuation of application No. 09/347,504, filed on Jul. 2, 1999, now Pat. No. 6,399,075.

(60) Provisional application No. 60/091,661, filed on Jul. 2, 1998.

(51) Int. Cl.
A61K 39/12 (2006.01)

(52) U.S. Cl. .................. 424/204.1; 530/300; 435/69.1

(58) Field of Classification Search ............. 424/204.1; 530/300; 435/6, 69.1
See application file for complete search history.

(56) References Cited

U.S. PATENT DOCUMENTS

| 5,656,599 | A | * | 8/1997 | Androphy et al. ............ 514/12 |
| 5,821,048 | A | | 10/1998 | Howley et al. |
| 5,932,412 | A | | 8/1999 | Dillner et al. |
| 6,399,075 | B1 | | 6/2002 | Howley et al. |
| 6,673,354 | B2 | | 1/2004 | Howley et al. .......... 421/204.1 |
| 2003/0194698 | A1 | * | 10/2003 | White et al. .................. 435/5 |

FOREIGN PATENT DOCUMENTS

WO    WO 92/11290    7/1992
WO    WO 96/41018    12/1996

OTHER PUBLICATIONS

Derossi et al. The Journal of Biological Chemistry, 1996, vol. 27, No. 30, pp. 18188-18193.*
Abroi, A. et al. *Transcriptional and replicational activation functions in the papillomavirus type 1 E2 protein are encoded by different structural determinants*, J. VIROL 70: 6169-6179 (1996).
Breiding, D.E. et al, *Genetic analysis of the bovine papillomavirus E2 transcriptional activation domain*, VIROLOGY 221: 34-43 (1996).
Brokaw, J.L., *Amino acids critical for the functions of the bovine papillomavirus type 1 transactivator*, J. VIROL. 70: 23-29 (1996).
Ferguson, M.F., *Genetic analysis of the activation domain of bovine papillomavirus protein E2: its role in transcription and replication*, J. VIROL. 70: 4193-4199 (1996).
Grossel, M.J., *Transcriptional activation function is not required for stimulation of DNA replication by bovine papillomavirus type 1 E2*, J. VIROL. 70: 7264-7269 (1996).

Kuo, S., *Cell-free replication of humanpapillomavirus DNA with homologous viral E1 and E2 proteins and human cell extracts*, J. Biol. Chem. 269: 24058-24065 (1994).
Liu, J., *The functions of human papillomavirus type 11 E1, E2, and E2C proteins in cell-free DNA replication*, J. Biol. Chem. 270: 27283-27291 (1995).
Lusky, M., *Cooperative assembly of the bovine papilloma virus E1 and E2 proteins on the replication origin requires an intact E2 binding site*, J. Biol. Chem. 268: 15795-15803 (1993).
Lusky, M., *The bovine papillomavirus E2 protein modulates the assembly of but is not stnbly maintained in a replication-competent multimeric E1-replication origin complex*, Proc. Natl. Acad. Sci. USA 91: 8895-8899 (1994).
McBride, A.A., *The carboxy-terminal domain shared by the bovine papillomavirus E2 transactivator and repressor protein contains a specific DNA binding activity*, EMBO J. 7: 533-539 (1988).
McBride, A.A., *E2 polypeptides encoded by bovine papillomavirus type I form dimers through the common carboxyl-terminal domain: transactivation is mediated by the conserved amino-terminal domain*, Pros. Natl. Acad. Sci. USA 86: 510-514 (1989).
Mohr, I. Et al, *Targeting the E1 replication protein to the papillomavirus origin of replication by complex formation with the E2 transactivator*, SCIENCE 250: 1694-1699 (1990).
Sedman, J. et al, *Cooperative interaction between the initiator E1 and the transcriptional activator E2 is required for replication of bovine papillomavirus in vivo and in vitro*, EMBO J. 14: 6218-6228 (1995).
Sedman, T., *Binding of the E1 and E2 proteins to the origin of replication of bovine papillomavirus*, J. VIROL 71: 2887-2896 (1997).
Seo, Y., *Bovine pappiloma virus (BPV)- encoded E2 protein enhances binding of E1 protein ot the BPV replication origin*, Proc. Natl. Acad. Sci. USA 90: 2865-2869 (1993).
Sverdrup, F., *Replication of human papillomavirus (HPV) DNAs supported by the HPV type 18 E1 and E2 proteins*, J. VIROL. 68: 505-509 (1994).
Ustav, M., *Transient replication of BPV-1 requires two viral polypeptides encoded by the E1 and E2 open reading frames*, EMBO J. 10: 449-457 (1991).
Winokur, P.L., *Separation of the transcriptional activation and replication functions of the bovine papillomavirus-1 E2 protein*, EMBO. J. 11: 4111-4118 (1992).
Yang, L., *Activation of BPV-1 replication in vitro by the transcription factor E2*, Nature 353: 628-632 (1991).
Yasugi, T., *Mappingand characterization of the interaction domains of the human papillomavirus type 16 E1 and E2 proteins*, J. VIROL. 71: 891-899 (1997).
Yasugi, T., *Two classes of human papillomavirus type 16 E1 mutants suggest pleitropic conformational constraints affecting E1 multimerization, E2 interaction, and interaction with cellular proteins*, J. VIROL. 71: 5942-5951 (1997).
Zou, N., *The carboxyl-terminal region of the human papillomavirus type 16 E1 protein determindes E2 protein specificity during DNA replication*, J. VIROL. 72: 3436-3441 (1998).

* cited by examiner

*Primary Examiner*—Ali R. Salimi
(74) *Attorney, Agent, or Firm*—Foley Hoag LLP

(57) ABSTRACT

By virtue of the present invention, there is provided methods and compositions for interfering with the proliferation of cells infected and/or transformed by papillomaviruses. The processes and compositions of this invention may be used to treat any mammal, including humans. According to this invention, mammals are treated by the pharmaceutically acceptable administration of an E2 peptidomimetic to reduce the symptoms of the specific papillomavirus-associated disease, or to prevent their recurrence.

20 Claims, 15 Drawing Sheets

A

```
                              E39
                               ↓
HPV16    ...DY KH  L CA  YYK  EM F
BPV1     ...LY TA  T NT  LYA  KK V
HPV6b    ...LH KC  H SV  LYK  QM L
HPV11    ...MH KC  L SV  LHK  QM L
HPV31    ...DY KH  L CV  MYK  EM I
HPV18    ...Q QY QL W NA  FFA  EH I
```

Consensus: IXXWXXVRXEXX<u>M</u>XXXARXXG
                    I      L
                           I

```
W Q L M R L E Q A L L Y K A R      HPV3
W Q T L R K E A V L L Y Y A R      HPV5
W K C M R H E S V L L Y K A K      HPV6a
W K C M R H E S V L L Y K A K      HPV6b
W K Y I R Y E S V I Y Y T A R      HPV7
W K C I R L E S V L L H K A K      HPV11
W K C L R Y E S V L L H K A R      HPV13
W K H M R L E C A I Y Y K A R      HPV16
W Q L I R W E N A I F F A A R      HPV18
W Q A L R R E A V L L Y Y A R      HPV24
W K L V R Y E C A I F Y K A R      HPV26
W Y L M R V E S A L Y Y K A R      HPV29
W K A V R H E N V V L Y K A R      HPV30
W K H I R L E C V L M Y K A R      HPV31
W K C L R I E A A L L F K A R      HPV32
W K L I R M E C A L L Y T A K      HPV33
W K H V R L E N V L L H K A R      HPV34
W K L I R L E C A V F Y K A R      HPV35
W K C V R M E N A I F Y A A R      HPV39
W K Y I R Y E S A I Y Y T A R      HPV40
W K C L R M E A V V L Y K A R      HPV42
W K C I R Y E C V L L H K A K      HPV44
W Q L I R L E N A I L F T A R      HPV45
W K L T R M E C V L F Y K A K      HPV52
W K A V R Q E N V I Y Y K A R      HPV53
W K C I R L E C A L Q Y K A R      HPV54
W K C I R Y E C V L L H K A K      HPV55
W K L I R M E C A I M Y T A R      HPV58
W K A V R H E Y V L Y Y K A R      HPV66
W R L R R I E C A L Y Y K A K      HPV67
W K Y V R L E N A I F Y A A R      HPV70
W C L M R L E S V L L Y K A R      HPV77

W T A V R T E N T L L Y A A R      BPV1

W K C V R Y E N V L L H K A R      common chimpanzee PV 1
W K C V R H E N V L L Y K A R      Pygmy chimpanzee PV type 1
W K C V R Q E C A V L Y K A R      rhesus monkey PV
```

| Name | Amino Acid Sequence |
|------|---------------------|
| WP15 | W K H M R L E C A I Y Y K A R |
| W33A | A K H M R L E C A I Y Y K A R |
| K34A | W A H M R L E C A I Y Y K A R |
| H35A | W K A M R L E C A I Y Y K A R |
| M36A | W K H A R L E C A I Y Y K A R |
| R37A | W K H M A L E C A I Y Y K A R |
| L38A | W K H M R A E C A I Y Y K A R |
| E39A | W K H M R L A C A I Y Y K A R |
| C40A | W K H M R L E A A I Y Y K A R |
| I42A | W K H M R L E C A A Y Y K A R |
| Y43A | W K H M R L E C A I A Y K A R |
| Y44A | W K H M R L E C A I Y A K A R |
| K45A | W K H M R L E C A I Y Y A A R |
| R47A | W K H M R L E C A I Y Y K A A |

Figure 10

| Papillomavirus Type | Amino Acid Sequence |
|---|---|
| | 33                                                   47 |
| HPV-16 | W K H M R L E C A I Y Y K A R |
| HPV-18 | W Q L I R W E N A I F F A A R |
| HPV-1A | W N L I R Q E Q V L F H F A R |
| HPV-6b | W K C M R H E S V L L Y K A K |
| HPV-11 | W K C I R L E S V L L H K A K |
| HPV-31 | W K H I R L E C V L M Y K A R |
| HPV-33 | W K L I R M E C A L L Y T A K |
| HPV-35 | W K L I R L E C A V F Y K A R |
| HPV-57 | W A Q V R L E N V M L F K A R |
| BPV-1 | W T A V R T E N T L L Y A A R |

Figure 12

A. Autoradiography

B. Band Intensities

SEQUENCE LISTING

```
<160> NUMBER OF SEQ ID NOS: 79

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Formula
      peptide
<220> FEATURE:
<221> NAME/KEY: MOD_RES
<222> LOCATION: (2)
<223> OTHER INFORMATION: Xaa = an amino acid residue having a polar
      sidechain, such as Arg, Asn, Cys, Glu, Gln, His,
      Lys, Ser, Thr or Tyr, or an analog thereof
<220> FEATURE:
<221> NAME/KEY: MOD_RES
<222> LOCATION: (3)
<223> OTHER INFORMATION: Xaa = an amino acid residue having a neutral
      sidechain, such as Ala, Asn, Cys, Gln, Gly, His,
      Ile, Leu, Met, Phe, Pro, Ser, Thr, Trp, Tyr, or
      Val, or an analog thereof
<220> FEATURE:
<221> NAME/KEY: MOD_RES
<222> LOCATION: (4)
<223> OTHER INFORMATION: Xaa = an amino acid residue having a
      hydrophobic sidechain, such as Ala, Gly, Ile, Leu, Met, Phe,
      Pro, Trp, Tyr, or an analog thereof
<220> FEATURE:
<221> NAME/KEY: MOD_RES
<222> LOCATION: (6)
<223> OTHER INFORMATION: Xaa = an amino acid residue having a basic
      sidechain, such as Arg, His or Lys, or a neutral
      sidechain, such as Ala, Asn, Cys, Gln, Gly, His,
      Phe, Trp or Tyr, or an anlog thereof
<220> FEATURE:
<221> NAME/KEY: MOD_RES
```

-continued

```
<222> LOCATION: (8)..(11)
<223> OTHER INFORMATION: Xaa = an amino acid residue having a neutral
      sidechain, such as Ala, Asn, Cys, Gln, Gly, His,
      Ile, Leu, Met, Phe, Pro, Ser, Thr, Trp, Tyr, or
      Val, or an analog thereof
<220> FEATURE:
<221> NAME/KEY: MOD_RES
<222> LOCATION: (12)
<223> OTHER INFORMATION: Xaa = an amino acid residue having an aromatic
      sidechain, such as His, Phe, Trp or Tyr, or an
      analog thereof
<220> FEATURE:
<221> NAME/KEY: MOD_RES
<222> LOCATION: (13)
<223> OTHER INFORMATION: Xaa = an amino acid residue having a basic
      sidechain, such as Arg, His or Lys, or a neutral
      sidechain, such as Ala, Asn, Cys, Gln, Gly, His,
      Ile, Leu, Met, Phe, Pro, Ser, Thr, Tyr or Val, or
<220> FEATURE:
<221> NAME/KEY: MOD_RES
<222> LOCATION: (15)
<223> OTHER INFORMATION: Xaa = an amino acid residue having a basic
      sidechain, such as Arg, His or Lys, or an analog
      thereof

<400> SEQUENCE: 1

Trp Xaa Xaa Xaa Arg Xaa Glu Xaa Xaa Xaa Xaa Xaa Xaa Ala Xaa
  1               5                  10                  15

<210> SEQ ID NO 2
<211> LENGTH: 12
<212> TYPE: PRT
<213> ORGANISM: Unknown
<220> FEATURE:
<223> OTHER INFORMATION: Description of Unknown Organism: EGF (epidermal
      growth factor)-derived peptide

<400> SEQUENCE: 2

Cys Met His Ile Glu Ser Leu Asp Ser Tyr Thr Cys
  1               5                  10

<210> SEQ ID NO 3
<211> LENGTH: 12
<212> TYPE: PRT
<213> ORGANISM: Unknown
<220> FEATURE:
<223> OTHER INFORMATION: Description of Unknown Organism: EGF (epidermal
      growth factor)-derived peptide

<400> SEQUENCE: 3

Cys Met Tyr Ile Glu Ala Leu Asp Lys Tyr Ala Cys
  1               5                  10

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence:
      pH-dependent membrane-binding internalizing peptide
<220> FEATURE:
<221> NAME/KEY: MOD_RES
<222> LOCATION: (1)
<223> OTHER INFORMATION: Xaa = a unique residue, such as cysteine or
      lysine
<220> FEATURE:
<221> NAME/KEY: MOD_RES
<222> LOCATION: (2)..(3)
<223> OTHER INFORMATION: Xaa = an amino acid selected to modulate the
      affinity of the internalizing peptide for
      different membranes

<400> SEQUENCE: 4
```

```
Xaa Xaa Xaa Glu Ala Ala Leu Ala Glu Ala Leu Ala Glu Ala Leu Ala
 1               5                  10                  15
Glu Ala Leu Ala Glu Ala Leu Ala Glu Ala Leu Glu Ala Leu Ala Ala
             20                  25                  30
```

<210> SEQ ID NO 5
<211> LENGTH: 8
<212> TYPE: PRT
<213> ORGANISM: Unknown
<220> FEATURE:
<223> OTHER INFORMATION: Description of Unknown Organism: A peptide
      substrate for N-myristoyl transferase

<400> SEQUENCE: 5

```
Gly Asn Ala Ala Ala Ala Arg Arg
 1               5
```

<210> SEQ ID NO 6
<211> LENGTH: 10
<212> TYPE: PRT
<213> ORGANISM: Unknown
<220> FEATURE:
<223> OTHER INFORMATION: Description of Unknown Organism: peptide
      derived from laminin

<400> SEQUENCE: 6

```
Cys Asp Pro Gly Tyr Ile Gly Ser Arg Cys
 1               5                  10
```

<210> SEQ ID NO 7
<211> LENGTH: 75
<212> TYPE: DNA
<213> ORGANISM: Artificial Sequence
<220> FEATURE:
<223> OTHER INFORMATION: Description of Artificial Sequence: Nde1-EcoR1
      fragment

<400> SEQUENCE: 7

```
catatgggtg gctgccgtgg cgatatgttc ggttgcggtg ctcctccaaa aaagaagaga    60
aaggtagctg gattc                                                    75
```

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence: RGD/SV40
      peptide

<400> SEQUENCE: 8

```
Met Gly Gly Cys Arg Gly Asp Met Phe Gly Cys Gly Ala Pro Pro Lys
 1               5                  10                  15
Lys Lys Arg Lys Val Ala Gly Phe
             20
```

<210> SEQ ID NO 9
<211> LENGTH: 225
<212> TYPE: DNA
<213> ORGANISM: Artificial Sequence
<220> FEATURE:
<223> OTHER INFORMATION: Description of Artificial Sequence: Nde1-EcoR1
      fragment

<400> SEQUENCE: 9

```
catatggagc cagtagatcc tagactagag ccctggaagc atccaggaag tcagcctaaa    60
```

```
actgcttgta ccaattgcta ttgtaaaaag tgttgctttc attgccaagt ttgtttcata      120
acaaaagccc ttggcatctc ctatggcagg aagaagcgga gacagcgacg aagacctcct      180
caaggcagtc agactcatca gtttctcta agtaagcaag gattc                       225

<210> SEQ ID NO 10
<211> LENGTH: 72
<212> TYPE: PRT
<213> ORGANISM: HIV
<220> FEATURE:
<223> OTHER INFORMATION: HIV-1 tat(1-72) peptide

<400> SEQUENCE: 10

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln
65                  70

<210> SEQ ID NO 11
<211> LENGTH: 912
<212> TYPE: DNA
<213> ORGANISM: Artificial Sequence
<220> FEATURE:
<223> OTHER INFORMATION: Description of Artificial Sequence: NdeI-EcoR1
      fragment

<400> SEQUENCE: 11
catatgacct ctcgccgctc cgtgaagtcg gtccgcggg aggttccgcg cgatgagtac       60
gaggatctgt actacacccc gtcttcaggt atggcgagtc ccgatagtcc gcctgacacc     120
tcccgccgtg cgccctaca gacacgctcg cgccagaggg gcgaggtccg tttcgtccag      180
tacgacgagt cggattatgc cctctacggg ggctcgtcat ccgaagacga cgaacacccg    240
gaggtccccc ggacgcggcg tcccgttttc ggggcggttt tgtccggccc ggggcctgcg    300
cgggcgcctc cgccacccgc tgggtccgga ggggccggac gcacacccac caccgccccc    360
cgggcccccc gaacccagcg ggtggcgact aaggcccccg cggccccggc ggcggagacc   420
acccgcggca ggaaatcggc ccagccagaa tccgccgcac tcccagacgc cccgcgtcg    480 acggcgccaa cccgatccaa gacacccgcg cagggggctgg ccagaaagct gcactttagc  540
accgcccccc caaaccccga cgcgccatgg acccccgggg tggccggctt taacaagcgc  600
gtcttctgcg ccgcggtcgg gcgcctggcg gccatgcatg cccggatggc ggcggtccag  660
ctctgggaca tgtcgcgtcc gcgcacagac gaagacctca cgaactcct tggcatcacc   720 accatccgcg tgacggtctg cgagggcaaa aacctgcttc agcgcgccaa cgagttggtg   780
aatccagacg tggtgcagga cgtcgacgcg gccacggcga ctcgagggcg ttctgcggcg   840
tcgcgcccca ccgagcgacc tcgagcccca gcccgctccg cttctcgccc cagacggccc   900
gtcgaggaat tc                                                        912

<210> SEQ ID NO 12
<211> LENGTH: 301
<212> TYPE: PRT
```

```
<213> ORGANISM: HSV
<220> FEATURE:
<223> OTHER INFORMATION: HSV-1 VP22 peptide

<400> SEQUENCE: 12

Met Thr Ser Arg Arg Ser Val Lys Ser Gly Pro Arg Glu Val Pro Arg
 1               5                  10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gly Arg Val Ala
            115                 120                 125

Thr Lys Ala Pro Ala Ala Pro Ala Ala Glu Thr Thr Arg Gly Arg Lys
        130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
            195                 200                 205

Ala Ala Met His Ala Arg Met Ala Ala Val Gln Leu Trp Asp Met Ser
210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
            275                 280                 285

Pro Ala Arg Ser Ala Ser Arg Pro Arg Arg Pro Val Glu
        290                 295                 300

<210> SEQ ID NO 13
<211> LENGTH: 120
<212> TYPE: DNA
<213> ORGANISM: Artificial Sequence
<220> FEATURE:
<223> OTHER INFORMATION: Description of Artificial Sequence: Nde1-EcoR1
      fragment

<400> SEQUENCE: 13
catatggacg tcgacgcggc cacggcgact cgagggcgtt ctgcggcgtc gcgccccacc    60
gagcgacctc gagccccagc ccgctccgct tctcgcccca gacggcccgt cgaggaattc   120
```

```
<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: VP22
      (C-terminal domain) peptide

<400> SEQUENCE: 14

Met Asp Val Asp Ala Ala Thr Ala Thr Arg Gly Arg Ser Ala Ala Ser
1               5                   10                  15

Arg Pro Thr Glu Arg Pro Arg Ala Pro Ala Arg Ser Ala Ser Arg Pro
            20                  25                  30

Arg Arg Pro Val Glu
            35

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Linker

<400> SEQUENCE: 15

Gly Gly Gly Ser Gly Gly Gly Ser Gly Gly Gly Ser Gly Gly Gly Ser
1               5                   10                  15

<210> SEQ ID NO 16
<211> LENGTH: 15
<212> TYPE: PRT
<213> ORGANISM: Homo sapiens

<400> SEQUENCE: 16

Trp Lys His Met Arg Leu Glu Cys Ala Ile Tyr Tyr Lys Ala Arg
1               5                   10                  15

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: protected
      tetrapeptide isostere

<400> SEQUENCE: 17

Ala Ile Tyr Tyr
1

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Consensus
      peptide
<220> FEATURE:
<221> NAME/KEY: MOD_RES
<222> LOCATION: (2)..(3)
<223> OTHER INFORMATION: Xaa = variable amino acid
<220> FEATURE:
<221> NAME/KEY: MOD_RES
<222> LOCATION: (4)
<223> OTHER INFORMATION: Xaa = Met, Val or Ile
<220> FEATURE:
<221> NAME/KEY: MOD_RES
<222> LOCATION: (6)
<223> OTHER INFORMATION: Xaa = variable amino acid
<220> FEATURE:
<221> NAME/KEY: MOD_RES
```

```
<222> LOCATION: (8)..(9)
<223> OTHER INFORMATION: Xaa = variable amino acid
<220> FEATURE:
<221> NAME/KEY: MOD_RES
<222> LOCATION: (10)
<223> OTHER INFORMATION: Xaa = Ile or Leu
<220> FEATURE:
<221> NAME/KEY: MOD_RES
<222> LOCATION: (11)..(14)
<223> OTHER INFORMATION: Xaa = a variable amino acid

<400> SEQUENCE: 18

Trp Xaa Xaa Xaa Arg Xaa Glu Xaa Xaa Xaa Xaa Xaa Xaa Xaa Ala Arg
 1               5                  10                  15

<210> SEQ ID NO 19
<211> LENGTH: 23
<212> TYPE: PRT
<213> ORGANISM: Homo sapiens
<220> FEATURE:
<223> OTHER INFORMATION: HPV16

<400> SEQUENCE: 19

His Ile Asp Tyr Trp Lys His Met Arg Leu Glu Cys Ala Ile Tyr Tyr
 1               5                  10                  15

Lys Ala Arg Glu Met Gly Phe
            20

<210> SEQ ID NO 20
<211> LENGTH: 23
<212> TYPE: PRT
<213> ORGANISM: Bovine sp.
<220> FEATURE:
<223> OTHER INFORMATION: BPV1

<400> SEQUENCE: 20

His Ile Leu Tyr Trp Thr Ala Val Arg Thr Glu Asn Thr Leu Leu Tyr
 1               5                  10                  15

Ala Ala Arg Lys Lys Gly Val
            20

<210> SEQ ID NO 21
<211> LENGTH: 23
<212> TYPE: PRT
<213> ORGANISM: Homo sapiens
<220> FEATURE:
<223> OTHER INFORMATION: HPV6b

<400> SEQUENCE: 21

His Val Leu His Trp Lys Cys Met Arg His Glu Ser Val Leu Leu Tyr
 1               5                  10                  15

Lys Ala Lys Gln Met Gly Leu
            20

<210> SEQ ID NO 22
<211> LENGTH: 23
<212> TYPE: PRT
<213> ORGANISM: Homo sapiens
<220> FEATURE:
<223> OTHER INFORMATION: HPV11

<400> SEQUENCE: 22

His Ile Met His Trp Lys Cys Ile Arg Leu Glu Ser Val Leu Leu His
 1               5                  10                  15

Lys Ala Lys Gln Met Gly Leu
            20
```

```
<210> SEQ ID NO 23
<211> LENGTH: 23
<212> TYPE: PRT
<213> ORGANISM: Homo sapiens
<220> FEATURE:
<223> OTHER INFORMATION: HPV31

<400> SEQUENCE: 23

His Ile Asp Tyr Trp Lys His Ile Arg Leu Glu Cys Val Leu Met Tyr
  1               5                  10                  15

Lys Ala Arg Glu Met Gly Ile
             20

<210> SEQ ID NO 24
<211> LENGTH: 23
<212> TYPE: PRT
<213> ORGANISM: Homo sapiens
<220> FEATURE:
<223> OTHER INFORMATION: HPV18

<400> SEQUENCE: 24

Gln Ile Gln Tyr Trp Gln Leu Ile Arg Trp Glu Asn Ala Ile Phe Phe
  1               5                  10                  15

Ala Ala Arg Glu His Gly Ile
             20

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Consensus
      peptide
<220> FEATURE:
<221> NAME/KEY: MOD_RES
<222> LOCATION: (2)..(3)
<223> OTHER INFORMATION: Xaa = variable amino acid
<220> FEATURE:
<221> NAME/KEY: MOD_RES
<222> LOCATION: (5...6)
<223> OTHER INFORMATION: Xaa = variable amino acid
<220> FEATURE:
<221> NAME/KEY: MOD_RES
<222> LOCATION: (7)
<223> OTHER INFORMATION: Xaa = Met, Val or Ile
<220> FEATURE:
<221> NAME/KEY: MOD_RES
<222> LOCATION: (9)
<223> OTHER INFORMATION: Xaa = variable amino acid
<220> FEATURE:
<221> NAME/KEY: MOD_RES
<222> LOCATION: (11)..(12)
<223> OTHER INFORMATION: xaa = variable amino acid
<220> FEATURE:
<221> NAME/KEY: MOD_RES
<222> LOCATION: (13)
<223> OTHER INFORMATION: Xaa = Ile or Leu
<220> FEATURE:
<221> NAME/KEY: MOD_RES
<222> LOCATION: (14)..(16)
<223> OTHER INFORMATION: xaa = variable amino acid
<220> FEATURE:
<221> NAME/KEY: MOD_RES
<222> LOCATION: (19)..(20)
<223> OTHER INFORMATION: xaa = variable amino acid

<400> SEQUENCE: 25

Ile Xaa Xaa Trp Xaa Xaa Xaa Arg Xaa Glu Xaa Xaa Xaa Xaa Xaa Xaa
  1               5                  10                  15
```

-continued

Ala Arg Xaa Xaa Gly
        20

<210> SEQ ID NO 26
<211> LENGTH: 15
<212> TYPE: PRT
<213> ORGANISM: Homo sapiens
<220> FEATURE:
<223> OTHER INFORMATION: HPV3

<400> SEQUENCE: 26

Trp Gln Leu Met Arg Leu Glu Gln Ala Leu Leu Tyr Lys Ala Arg
 1               5                  10                  15

<210> SEQ ID NO 27
<211> LENGTH: 15
<212> TYPE: PRT
<213> ORGANISM: Homo sapiens
<220> FEATURE:
<223> OTHER INFORMATION: HPV5

<400> SEQUENCE: 27

Trp Gln Thr Leu Arg Lys Glu Ala Val Leu Tyr Tyr Ala Arg
 1               5                  10                  15

<210> SEQ ID NO 28
<211> LENGTH: 15
<212> TYPE: PRT
<213> ORGANISM: Homo sapiens
<220> FEATURE:
<223> OTHER INFORMATION: HPV6a

<400> SEQUENCE: 28

Trp Lys Cys Met Arg His Glu Ser Val Leu Leu Tyr Lys Ala Lys
 1               5                  10                  15

<210> SEQ ID NO 29
<211> LENGTH: 15
<212> TYPE: PRT
<213> ORGANISM: Homo sapiens
<220> FEATURE:
<223> OTHER INFORMATION: HPV6b

<400> SEQUENCE: 29

Trp Lys Cys Met Arg His Glu Ser Val Leu Leu Tyr Lys Ala Lys
 1               5                  10                  15

<210> SEQ ID NO 30
<211> LENGTH: 15
<212> TYPE: PRT
<213> ORGANISM: Homo sapiens
<220> FEATURE:
<223> OTHER INFORMATION: HPV7

<400> SEQUENCE: 30

Trp Lys Tyr Ile Arg Tyr Glu Ser Val Ile Tyr Tyr Thr Ala Arg
 1               5                  10                  15

<210> SEQ ID NO 31
<211> LENGTH: 15
<212> TYPE: PRT
<213> ORGANISM: Homo sapiens
<220> FEATURE:
<223> OTHER INFORMATION: HPV11

<400> SEQUENCE: 31

Trp Lys Cys Ile Arg Leu Glu Ser Val Leu Leu His Lys Ala Lys

-continued

<210> SEQ ID NO 32
<211> LENGTH: 15
<212> TYPE: PRT
<213> ORGANISM: Homo sapiens
<220> FEATURE:
<223> OTHER INFORMATION: HPV13

<400> SEQUENCE: 32

Trp Lys Cys Leu Arg Tyr Glu Ser Val Leu Leu His Lys Ala Arg
 1               5                  10                  15

<210> SEQ ID NO 33
<211> LENGTH: 15
<212> TYPE: PRT
<213> ORGANISM: Homo sapiens
<220> FEATURE:
<223> OTHER INFORMATION: HPV16

<400> SEQUENCE: 33

Trp Lys His Met Arg Leu Glu Cys Ala Ile Tyr Tyr Lys Ala Arg
 1               5                  10                  15

<210> SEQ ID NO 34
<211> LENGTH: 15
<212> TYPE: PRT
<213> ORGANISM: Homo sapiens
<220> FEATURE:
<223> OTHER INFORMATION: HPV18

<400> SEQUENCE: 34

Trp Gln Leu Ile Arg Trp Glu Asn Ala Ile Phe Phe Ala Ala Arg
 1               5                  10                  15

<210> SEQ ID NO 35
<211> LENGTH: 15
<212> TYPE: PRT
<213> ORGANISM: Homo sapiens
<220> FEATURE:
<223> OTHER INFORMATION: HPV24

<400> SEQUENCE: 35

Trp Gln Ala Leu Arg Arg Glu Ala Val Leu Leu Tyr Tyr Ala Arg
 1               5                  10                  15

<210> SEQ ID NO 36
<211> LENGTH: 15
<212> TYPE: PRT
<213> ORGANISM: Homo sapiens
<220> FEATURE:
<223> OTHER INFORMATION: HPV26

<400> SEQUENCE: 36

Trp Lys Leu Val Arg Tyr Glu Cys Ala Ile Phe Tyr Lys Ala Arg
 1               5                  10                  15

<210> SEQ ID NO 37
<211> LENGTH: 15
<212> TYPE: PRT
<213> ORGANISM: Homo sapiens
<220> FEATURE:
<223> OTHER INFORMATION: HPV29

<400> SEQUENCE: 37

Trp Tyr Leu Met Arg Val Glu Ser Ala Leu Tyr Tyr Lys Ala Arg
 1               5                  10                  15

<210> SEQ ID NO 38
<211> LENGTH: 15
<212> TYPE: PRT
<213> ORGANISM: Homo sapiens
<220> FEATURE:
<223> OTHER INFORMATION: HPV30

<400> SEQUENCE: 38

Trp Lys Ala Val Arg His Glu Asn Val Val Leu Tyr Lys Ala Arg
 1               5                  10                  15

<210> SEQ ID NO 39
<211> LENGTH: 15
<212> TYPE: PRT
<213> ORGANISM: Homo sapiens
<220> FEATURE:
<223> OTHER INFORMATION: HPV31

<400> SEQUENCE: 39

Trp Lys His Ile Arg Leu Glu Cys Val Leu Met Tyr Lys Ala Arg
 1               5                  10                  15

<210> SEQ ID NO 40
<211> LENGTH: 15
<212> TYPE: PRT
<213> ORGANISM: Homo sapiens
<220> FEATURE:
<223> OTHER INFORMATION: HPV32

<400> SEQUENCE: 40

Trp Lys Cys Leu Arg Ile Glu Ala Ala Leu Leu Phe Lys Ala Arg
 1               5                  10                  15

<210> SEQ ID NO 41
<211> LENGTH: 15
<212> TYPE: PRT
<213> ORGANISM: Homo sapiens
<220> FEATURE:
<223> OTHER INFORMATION: HPV33

<400> SEQUENCE: 41

Trp Lys Leu Ile Arg Met Glu Cys Ala Leu Leu Tyr Thr Ala Lys
 1               5                  10                  15

<210> SEQ ID NO 42
<211> LENGTH: 15
<212> TYPE: PRT
<213> ORGANISM: Homo sapiens
<220> FEATURE:
<223> OTHER INFORMATION: HPV34

<400> SEQUENCE: 42

Trp Lys His Val Arg Leu Glu Asn Val Leu Leu His Lys Ala Arg
 1               5                  10                  15

<210> SEQ ID NO 43
<211> LENGTH: 15
<212> TYPE: PRT
<213> ORGANISM: Homo sapiens
<220> FEATURE:
<223> OTHER INFORMATION: HPV35

<400> SEQUENCE: 43

Trp Lys Leu Ile Arg Leu Glu Cys Ala Val Phe Tyr Lys Ala Arg
 1               5                  10                  15

```
<210> SEQ ID NO 44
<211> LENGTH: 15
<212> TYPE: PRT
<213> ORGANISM: Homo sapiens
<220> FEATURE:
<223> OTHER INFORMATION: HPV39

<400> SEQUENCE: 44

Trp Lys Cys Val Arg Met Glu Asn Ala Ile Phe Tyr Ala Ala Arg
 1               5                  10                  15

<210> SEQ ID NO 45
<211> LENGTH: 15
<212> TYPE: PRT
<213> ORGANISM: Homo sapiens
<220> FEATURE:
<223> OTHER INFORMATION: HPV40

<400> SEQUENCE: 45

Trp Lys Tyr Ile Arg Tyr Glu Ser Ala Ile Tyr Tyr Thr Ala Arg
 1               5                  10                  15

<210> SEQ ID NO 46
<211> LENGTH: 15
<212> TYPE: PRT
<213> ORGANISM: Homo sapiens
<220> FEATURE:
<223> OTHER INFORMATION: HPV42

<400> SEQUENCE: 46

Trp Lys Cys Leu Arg Met Glu Ala Val Val Leu Tyr Lys Ala Arg
 1               5                  10                  15

<210> SEQ ID NO 47
<211> LENGTH: 15
<212> TYPE: PRT
<213> ORGANISM: Homo sapiens
<220> FEATURE:
<223> OTHER INFORMATION: HPV44

<400> SEQUENCE: 47

Trp Lys Cys Ile Arg Tyr Glu Cys Val Leu Leu His Lys Ala Lys
 1               5                  10                  15

<210> SEQ ID NO 48
<211> LENGTH: 15
<212> TYPE: PRT
<213> ORGANISM: Homo sapiens
<220> FEATURE:
<223> OTHER INFORMATION: HPV45

<400> SEQUENCE: 48

Trp Gln Leu Ile Arg Leu Glu Asn Ala Ile Leu Phe Thr Ala Arg
 1               5                  10                  15

<210> SEQ ID NO 49
<211> LENGTH: 15
<212> TYPE: PRT
<213> ORGANISM: Homo sapiens
<220> FEATURE:
<223> OTHER INFORMATION: HPV52

<400> SEQUENCE: 49

Trp Lys Leu Thr Arg Met Glu Cys Val Leu Phe Tyr Lys Ala Lys
 1               5                  10                  15
```

```
<210> SEQ ID NO 50
<211> LENGTH: 15
<212> TYPE: PRT
<213> ORGANISM: Homo sapiens
<220> FEATURE:
<223> OTHER INFORMATION: HPV53

<400> SEQUENCE: 50

Trp Lys Ala Val Arg Gln Glu Asn Val Ile Tyr Tyr Lys Ala Arg
 1               5                  10                  15

<210> SEQ ID NO 51
<211> LENGTH: 15
<212> TYPE: PRT
<213> ORGANISM: Homo sapiens
<220> FEATURE:
<223> OTHER INFORMATION: HPV54

<400> SEQUENCE: 51

Trp Lys Cys Ile Arg Leu Glu Cys Ala Leu Gln Tyr Lys Ala Arg
 1               5                  10                  15

<210> SEQ ID NO 52
<211> LENGTH: 15
<212> TYPE: PRT
<213> ORGANISM: Homo sapiens
<220> FEATURE:
<223> OTHER INFORMATION: HPV55

<400> SEQUENCE: 52

Trp Lys Cys Ile Arg Tyr Glu Cys Val Leu Leu His Lys Ala Lys
 1               5                  10                  15

<210> SEQ ID NO 53
<211> LENGTH: 15
<212> TYPE: PRT
<213> ORGANISM: Homo sapiens
<220> FEATURE:
<223> OTHER INFORMATION: HPV58

<400> SEQUENCE: 53

Trp Lys Leu Ile Arg Met Glu Cys Ala Ile Met Tyr Thr Ala Arg
 1               5                  10                  15

<210> SEQ ID NO 54
<211> LENGTH: 15
<212> TYPE: PRT
<213> ORGANISM: Homo sapiens
<220> FEATURE:
<223> OTHER INFORMATION: HPV66

<400> SEQUENCE: 54

Trp Lys Ala Val Arg His Glu Tyr Val Leu Tyr Tyr Lys Ala Arg
 1               5                  10                  15

<210> SEQ ID NO 55
<211> LENGTH: 15
<212> TYPE: PRT
<213> ORGANISM: Homo sapiens
<220> FEATURE:
<223> OTHER INFORMATION: HPV67

<400> SEQUENCE: 55

Trp Arg Leu Arg Arg Ile Glu Cys Ala Leu Tyr Tyr Lys Ala Lys
 1               5                  10                  15

<210> SEQ ID NO 56
```

-continued

```
<211> LENGTH: 15
<212> TYPE: PRT
<213> ORGANISM: Homo sapiens
<220> FEATURE:
<223> OTHER INFORMATION: HPV70

<400> SEQUENCE: 56

Trp Lys Tyr Val Arg Leu Glu Asn Ala Ile Phe Tyr Ala Ala Arg
 1               5                  10                  15

<210> SEQ ID NO 57
<211> LENGTH: 15
<212> TYPE: PRT
<213> ORGANISM: Homo sapiens
<220> FEATURE:
<223> OTHER INFORMATION: HPV77

<400> SEQUENCE: 57

Trp Cys Leu Met Arg Leu Glu Ser Val Leu Leu Tyr Lys Ala Arg
 1               5                  10                  15

<210> SEQ ID NO 58
<211> LENGTH: 15
<212> TYPE: PRT
<213> ORGANISM: Bovine sp.
<220> FEATURE:
<223> OTHER INFORMATION: BPV1

<400> SEQUENCE: 58

Trp Thr Ala Val Arg Thr Glu Asn Thr Leu Leu Tyr Ala Ala Arg
 1               5                  10                  15

<210> SEQ ID NO 59
<211> LENGTH: 15
<212> TYPE: PRT
<213> ORGANISM: Pan Troglodytes
<220> FEATURE:
<223> OTHER INFORMATION: common PV1

<400> SEQUENCE: 59

Trp Lys Cys Val Arg Tyr Glu Asn Val Leu Leu His Lys Ala Arg
 1               5                  10                  15

<210> SEQ ID NO 60
<211> LENGTH: 15
<212> TYPE: PRT
<213> ORGANISM: Pan Troglodytes
<220> FEATURE:
<223> OTHER INFORMATION: pygmy PV

<400> SEQUENCE: 60

Trp Lys Cys Val Arg His Glu Asn Val Leu Leu Tyr Lys Ala Arg
 1               5                  10                  15

<210> SEQ ID NO 61
<211> LENGTH: 15
<212> TYPE: PRT
<213> ORGANISM: Callimico goeldi
<220> FEATURE:
<223> OTHER INFORMATION: rhesus PV

<400> SEQUENCE: 61

Trp Lys Cys Val Arg Gln Glu Cys Ala Val Leu Tyr Lys Ala Arg
 1               5                  10                  15

<210> SEQ ID NO 62
<211> LENGTH: 15
```

```
<212> TYPE: PRT
<213> ORGANISM: Homo sapiens
<220> FEATURE:
<223> OTHER INFORMATION: WP15

<400> SEQUENCE: 62

Trp Lys His Met Arg Leu Glu Cys Ala Ile Tyr Tyr Lys Ala Arg
 1               5                  10                  15

<210> SEQ ID NO 63
<211> LENGTH: 15
<212> TYPE: PRT
<213> ORGANISM: Homo sapiens
<220> FEATURE:
<223> OTHER INFORMATION: W33A

<400> SEQUENCE: 63

Ala Lys His Met Arg Leu Glu Cys Ala Ile Tyr Tyr Lys Ala Arg
 1               5                  10                  15

<210> SEQ ID NO 64
<211> LENGTH: 15
<212> TYPE: PRT
<213> ORGANISM: Homo sapiens
<220> FEATURE:
<223> OTHER INFORMATION: K34A

<400> SEQUENCE: 64

Trp Ala His Met Arg Leu Glu Cys Ala Ile Tyr Tyr Lys Ala Arg
 1               5                  10                  15

<210> SEQ ID NO 65
<211> LENGTH: 15
<212> TYPE: PRT
<213> ORGANISM: Homo sapiens
<220> FEATURE:
<223> OTHER INFORMATION: H35A

<400> SEQUENCE: 65

Trp Lys Ala Met Arg Leu Glu Cys Ala Ile Tyr Tyr Lys Ala Arg
 1               5                  10                  15

<210> SEQ ID NO 66
<211> LENGTH: 15
<212> TYPE: PRT
<213> ORGANISM: Homo sapiens
<220> FEATURE:
<223> OTHER INFORMATION: M36A

<400> SEQUENCE: 66

Trp Lys His Ala Arg Leu Glu Cys Ala Ile Tyr Tyr Lys Ala Arg
 1               5                  10                  15

<210> SEQ ID NO 67
<211> LENGTH: 15
<212> TYPE: PRT
<213> ORGANISM: Homo sapiens
<220> FEATURE:
<223> OTHER INFORMATION: R37A

<400> SEQUENCE: 67

Trp Lys His Met Ala Leu Glu Cys Ala Ile Tyr Tyr Lys Ala Arg
 1               5                  10                  15

<210> SEQ ID NO 68
<211> LENGTH: 15
<212> TYPE: PRT
```

```
<213> ORGANISM: Homo sapiens
<220> FEATURE:
<223> OTHER INFORMATION: L38A

<400> SEQUENCE: 68

Trp Lys His Met Arg Ala Glu Cys Ala Ile Tyr Tyr Lys Ala Arg
 1               5                  10                  15

<210> SEQ ID NO 69
<211> LENGTH: 15
<212> TYPE: PRT
<213> ORGANISM: Homo sapiens
<220> FEATURE:
<223> OTHER INFORMATION: E39A

<400> SEQUENCE: 69

Trp Lys His Met Arg Leu Ala Cys Ala Ile Tyr Tyr Lys Ala Arg
 1               5                  10                  15

<210> SEQ ID NO 70
<211> LENGTH: 15
<212> TYPE: PRT
<213> ORGANISM: Homo sapiens
<220> FEATURE:
<223> OTHER INFORMATION: C40A

<400> SEQUENCE: 70

Trp Lys His Met Arg Leu Glu Ala Ala Ile Tyr Tyr Lys Ala Arg
 1               5                  10                  15

<210> SEQ ID NO 71
<211> LENGTH: 15
<212> TYPE: PRT
<213> ORGANISM: Homo sapiens
<220> FEATURE:
<223> OTHER INFORMATION: I42A

<400> SEQUENCE: 71

Trp Lys His Met Arg Leu Glu Cys Ala Ala Tyr Tyr Lys Ala Arg
 1               5                  10                  15

<210> SEQ ID NO 72
<211> LENGTH: 15
<212> TYPE: PRT
<213> ORGANISM: Homo sapiens
<220> FEATURE:
<223> OTHER INFORMATION: Y43A

<400> SEQUENCE: 72

Trp Lys His Met Arg Leu Glu Cys Ala Ile Ala Tyr Lys Ala Arg
 1               5                  10                  15

<210> SEQ ID NO 73
<211> LENGTH: 15
<212> TYPE: PRT
<213> ORGANISM: Homo sapiens
<220> FEATURE:
<223> OTHER INFORMATION: Y44A

<400> SEQUENCE: 73

Trp Lys His Met Arg Leu Glu Cys Ala Ile Tyr Ala Lys Ala Arg
 1               5                  10                  15

<210> SEQ ID NO 74
<211> LENGTH: 15
<212> TYPE: PRT
<213> ORGANISM: Homo sapiens
```

```
<220> FEATURE:
<223> OTHER INFORMATION: K45A

<400> SEQUENCE: 74

Trp Lys His Met Arg Leu Glu Cys Ala Ile Tyr Tyr Ala Ala Arg
 1               5                  10                  15

<210> SEQ ID NO 75
<211> LENGTH: 15
<212> TYPE: PRT
<213> ORGANISM: Homo sapiens
<220> FEATURE:
<223> OTHER INFORMATION: R47A

<400> SEQUENCE: 75

Trp Lys His Met Arg Leu Glu Cys Ala Ile Tyr Tyr Lys Ala Ala
 1               5                  10                  15

<210> SEQ ID NO 76
<211> LENGTH: 15
<212> TYPE: PRT
<213> ORGANISM: Homo sapiens
<220> FEATURE:
<223> OTHER INFORMATION: HPV-1A

<400> SEQUENCE: 76

Trp Asn Leu Ile Arg Gln Glu Gln Val Leu Phe His Phe Ala Arg
 1               5                  10                  15

<210> SEQ ID NO 77
<211> LENGTH: 15
<212> TYPE: PRT
<213> ORGANISM: Homo sapiens
<220> FEATURE:
<223> OTHER INFORMATION: HPV-57

<400> SEQUENCE: 77

Trp Ala Gln Val Arg Leu Glu Asn Val Met Leu Phe Lys Ala Arg
 1               5                  10                  15

<210> SEQ ID NO 78
<211> LENGTH: 31
<212> TYPE: PRT
<213> ORGANISM: Homo sapiens

<400> SEQUENCE: 78

Gly Arg Lys Lys Arg Arg Gln Arg Arg Pro Pro Gln Cys Gly Gly
 1               5                  10                  15

Trp Lys His Met Arg Leu Glu Cys Ala Ile Tyr Tyr Lys Ala Arg
                20                  25                  30

<210> SEQ ID NO 79
<211> LENGTH: 34
<212> TYPE: PRT
<213> ORGANISM: Homo sapiens

<400> SEQUENCE: 79

Glu Arg Gln Ile Lys Ile Trp Phe Gln Asn Arg Arg Met Lys Trp Lys
 1               5                  10                  15

Lys Gly Gly Trp Lys His Met Arg Leu Glu Cys Ala Ile Tyr Tyr Lys
                20                  25                  30

Ala Arg
```

COMPOSITIONS AND METHODS FOR TREATING PAPILLOMAVIRUS-INFECTED CELLS

CROSS REFERENCE TO RELATED APPLICATIONS

This application is a continuation of U.S. patent application Ser. No. 10/161,499, filed Jun. 3, 2002 now U.S. Pat No. 6,673, 354, which is a continuation of U.S. patent application Ser. No. 09/347,504 filed Jul. 2, 1999 now U.S. Pat. No. 6,399,075, which claims the benefit of U.S. Provisional Application No. 60/091,661, filed Jul. 2, 1998, the contents of both of which are specifically incorporated by reference herein.

BACKGROUND OF THE INVENTION

Papillomaviruses (PV) have been linked to widespread, serious human diseases, especially carcinomas of the genital and oral mucosa. Tens of millions of women suffer from human papilloma virus (HPV) infection of the genital tract. Approximately 500,000 women worldwide develop cancer of the cervix each year and it is the second most common cause of cancer deaths in women worldwide. Approximately 90–95% of all cervical cancers may be linked to HPV.

In addition to causing severe cancerous conditions, Papillomaviruses more commonly induce benign, dysplastic and malignant hyperproliferations of skin and mucosal epithelium (see, for example, Mansur and Androphy, (1993) Biochem Biophys Acta 1155:323–345; Shah and Howley (1996) Fields Virology, 3$^{rd}$ Ed., 2077–2110; and Howley (1996) Fields Virology, 3$^{rd}$ Ed., 2045–2076, for reviews of the molecular, cellular, and clinical aspects of the papillomaviruses). For example, a wide variety of warts are found on human skin and are caused by the human papillomavirus (HPV). Examples of such warts include common warts (verruca vulgaris), plantar warts, palmar warts, planar warts (verruca plana), mosaic warts, and venereal warts (condyloma accuminatum). These skin growths are unsightly, irritating, and potentially carcinogenic, and their removal is desirable.

Over 70 different HPV types have been identified, and these different papillomavirus types are known to cause distinct diseases, c.f., zur Hausen, (1996) Biophysica Acta 1288:55–78; Pfister, (1987) Adv. Cancer Res., 48:113–147; and Syrjanen, (1984) Obstet. Gynecol. Survey 39:252–265. The HPVs that cause anogenital warts can be further classified either high risk (such as HPV type 16 [HPV-16] and HPV-18) or low risk (or HPV-6 and HPV-11) on the basis of the clinical lesions with which they are associated and the relative propensity for these lesions to progress to cancer. For example, HPV types 1 and 2 cause common warts, and types 6 and 11 cause warts of the external genitalia, anus and cervix. HPV's of the high risk classification can be identified in the majority of cervical cancers, e.g., approximately 90% of human cervical cancers harbor the DNA of a high-risk HPV. Types 16, 18, 31 and 33 are particularly common; HPV-16 is present in about 50 percent of all cervical cancers.

The genetic organization of the papillomaviruses are defined by ten open reading frames (ORFs) which are located on one strand of the viral DNA. These 10 genes are classified as early (E) and late (L) genes, depending on the time at which they are expressed in the viral life cycle, as shown in FIG. 1. Several of the papillomavirus early genes code for regulatory proteins that are of particular interest. The high-risk HPV encoded E6 protein, for example, causes p53 degradation and the E7 protein interacts with Rb and other pocket proteins (Howley et al., Fields Virology, Third Ed., Philadelphia: 1996). Notably, the E1 and E2 regulatory proteins play important roles in papillomavirus transcriptional regulation and viral DNA replication.

The biological life cycle of the papillomaviruses appears to differ from most other viral pathogens. These viruses are believed to infect the basal or stem cells of the squamous epithelium. Rather than proceeding to a lytic infection in which viral replication kills the cell, viral DNA transcription and replication are maintained at very low levels until the infected epithelial cell migrates into the upper strata of the squamous epithelium. There, presumably in response to differentiation-specific signals, the progression of viral transcription changes, viral DNA synthesis begins and infectious virions assemble. In this type of replication, hundreds of copies of the genomes are produced per cell, and these are packaged into progeny virions. High levels of E1 and E2 are observed in cells undergoing papillomavirus vegetative replication.

The papillomavirus E1 protein is the most conserved papillomavirus protein. The HPV-16 E1 protein is 649 amino acids long and has a molecular weight of 68-kd. The E1 protein is the only papillamovirus encoded DNA replication enzyme. All other replication enzymes, e.g., polymerases, primases, etc. are provided by the infected host cell. The E1 protein is a nuclear phosphoprotein and ATP-dependent DNA helicase that binds to the origin of DNA replication (ori), thus initiating viral plasmid replication (Howley 1996). The minimal DNA binding domain of the E1 proteins is found in the amino terminus. The HPV-16 E1 carboxy-terminus contains a domain that is necessary and sufficient for interaction with the E2 protein. This domain also includes an ATP binding pocket similar to that found in SV40 large T antigen (LgT).

Interestingly, the papillomavirus E1 protein shares many structural and functional similarities with the large T antigen (LgT) of simian virus (SV40), the replication protein of that virus. Both E1 and LgT bind a region of dyad symmetry within the DNA replication origin and have ATP-dependent DNA helicase activity that can catalyze the unwinding of ori-containing double-stranded DNA templates (Smelkova and Borowiec, Journal of Virology, 1997, 71, 8766; Chen et al., Journal of Virology, 1997, 72, 2567). One important difference between the two proteins is that LgT is the only viral protein required for initiation of SV40 replication (Bullock et al., Critical Reviews in Biochemistry and Molecular Biology, 1997, 32, 503), whereas E1 is efficiently recruited to the viral DNA replication origin, only through interaction with the virus encoded E2 protein (see below).

The papillomavirus E2 protein is a critical regulator of both viral DNA replication and gene expression. HPV-16 E2 is 365 amino acids long and has a molecular weight of 38-kD. E2 proteins are composed of two well-conserved functional domains, as shown in FIG. 2. The E2 carboxy-terminus includes a DNA binding domain that binds as a dimer to the ACCN6GGT recognition sequence (Andropy et al., Nature, 1987, 325, 70). The E2 amino-terminus features a transcriptional activation domain that regulates viral gene expression and interacts with components of the host cell apparatus. The E2 N-terminus also interacts with the E1 protein. These amino-terminal and the carboxy-terminal domains are connected by a hinge region that is dispensable for both replication and transcriptional activation.

Genetic studies have revealed that stable BPV-1 plasmid replication requires the expression of the viral E1 and E2 genes (DelVecchio et al., Journal of Virology, 1992, 66, 5949; Di Maio et al., EMBO, 1988, 7, 1197; Sarver et al., Journal of Virology, 1984, 52, 377). Though E1 and E2 are both essential factors for stable DNA replication, it appears that only E1 is directly involved in plasmid replication (DiMaio and Settlement 1986, Ustav et al. 1991). However, extensive research over the past ten years has been conducted to elucidate the role of E2 in DNA replication, and the results of these numerous studies suggest that (1) HPV-16 E2 transactivation functions are independent of and separable from its E1 interaction (i.e., replication activity), (2) E1 binding is necessary for E2 stimulation of DNA replication. E2, by binding to ACC 6GT recognition sequences that flank the viral DNA replication origin, recruits E1 to the origin. In this way, E2 effects initiation of the formation of the viral replication complex.

Thus, since the formation of an E1–E2 complex is necessary for stimulation of DNA replication, moieties that can block the formation of this complex could serve to inhibit viral DNA replication and thus the proliferation of harmful conditions as described above.

Towards this end, European patent application 302,758 refers to the use of modified forms of E2 protein that bind to, and block, E2 binding sites on papillomavirus DNA without resulting in trans-activation. That application also refers to repression of E2 activation through the use of DNA fragments that mimic E2 binding sites, and thus bind with E2 trans-activators, making them unavailable for binding to E2 sites on the viral DNA.

Additionally, U.S. Pat. No. 5,219,990 describes the use of E2 trans-activation repressors which interfere with normal functioning of the native full-length E2 transcriptional activation protein of the papillomavirus. However, the E2 trans-activation repressors of the '990 patent are proteins that dimerize with the full-length native E2 protein to form inactive heterodimers, thus interfering with the formation of active homodimers comprising full-length native E2 polypeptides and thereby repressing papillomavirus transcription and replication. The E2 trans-activation repressors are described as fragments of the E2 polypeptide in which the dimerization function has been separated from its DNA binding function, e.g., the E2 trans-activation repressors includes at least the dimerization region, but less than the DNA binding domain, of the E2 polypeptide.

Although these references are directed towards the blocking of complex formation, each of these references describes the use of large biological molecules, namely proteins, to achieve this goal. Clearly, there remains a need for the development of simpler, preferably cell-permeable, small molecule therapeutics capable of treating a papillomavirus-induced condition, lessening the severity of such condition, or preventing the occurrence of such condition.

SUMMARY OF THE INVENTION

One aspect of the present invention provides a method of treating, e.g., lessening the severity or preventing the occurrence of a papillomavirus-induced condition, such as a papillomavirus-induced lesion. In general, the subject method comprises administering to an animal, e.g. a human, infected with a papillomavirus a pharmaceutical preparation comprising a therapeutically effective amount of a small organic molecule which can inhibit E1-E2 interaction. In preferred embodiments, the inhibitor has a molecular weight of less than 10,000 amu, more preferably less than 7500 amu, 5000 amu, and even more preferably less than 3000 armu. For instance, the E2 inhibitor can be either (i) an E2 peptide or peptidomimetic, preferably corresponding in length to a 3–25 mer, e.g., in certain embodiments, containing a core sequence of R-X(4)-E-X(5)-X(6)-X(7) and in other embodiments, including the core sequence W-X(1)-X(2)-X(3)-R-X(4)-E-X(5)-X(6)-X(7)-X(8)-X(9)-X(10)-A-X(11), or (ii) a gene construct for expressing the E2 peptide. The E2 peptide, peptidomimetic or gene construct is formulated in the pharmaceutical preparation for delivery into PV-infected cells of the animal.

In preferred embodiments, the subject method is used to treat a human who is infected with a human papillomavirus (HPV), particularly a high risk HPV such as HPV-16, HPV-18, HPV-31 and HPV-33. In other preferred embodiments, treatment of low risk HPV conditions, e.g., particular topical treatment of cutaneous or mucosal low risk HPV lesions, is also contemplated.

The subject method can be used to inhibit pathological progression of papillomavirus infection, such as preventing or reversing the formation of warts, e.g. Plantar warts (verruca plantaris), common warts (verruca plana), Butcher's common warts, flat warts, genital warts (condyloma acuminatum), or epidermodysplasia verruciformis; as well as treating papillomavirus-infected cells which have become, or are at risk of becoming, transformed and/or immortalized, e.g. cancerous, e.g. a laryngeal papilloma, a focal epithelial, a cervical carcinoma, or as an adjunct to chemotherapy, radiation, surgical or other therapies for eliminating residual infected or pre-cancerous cells.

Yet another aspect of the invention relates to a pharmaceutical preparation comprising a therapeutically effective amount of an E2 peptidomimetic, formulated in the pharmaceutical preparation for delivery into PV-infected cells of an animal. In preferred embodiments, the polypeptide is formulated as a liposome.

As will be appreciated by one of ordinary skill in the art, the compositions and preparations described herein can also be utilized serially or in combination with conventional therapeutic agents or regimens including, but not limited to, salicylic acid, podophyllotoxin, retinoic acid, surgery, laser therapy, radiation, and cryotherapy.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

BRIEF DESCRIPTION OF THE FIGURES

FIG. 5A. Derivation of candidate HPV16 E1–E2 interaction inhibitory peptides based on conserved residues within the E2 amino terminus. Mutagenesis studies identified residue E39 of HPV16 E2 as critical for interaction with E1. The upper panel shows an alignment of conserved proximal sequences in other papillomavirus E2 proteins. A deduced consensus sequence is shown in the middle panel. The lower panel shows the sequences of the synthetic peptides derived from this portion of HPV16 E2. WP peptides retain the conserved glutamic acid at the position analogous to E39 of HPV16 E2, whereas the MP peptides contain a substituted alanine at this position.

FIG. 5B. Sequence alignment of various papillomavirus E2 proteins.

FIG. 10. Amino acid sequences of HPV-16 E2 derived 15-amino acid peptides containing single amino acid alanine substitutions. Wild-type peptide is denoted as "WP15". For mutant peptides, name describes position and identity of original residue for which an alanine was substituted. Each substituted residue is underlined.

FIG. 12. Alignment of conserved E39-proximal amino acid sequences of papillomavirus E2 proteins. Conserved residues are highlighted by the boxes.

DETAILED DESCRIPTION OF THE INVENTION

I. Overview

According to the present invention, there is provided methods and compositions for interfering with papillomavirus DNA replication. The processes and compositions of this invention may be used to treat any mammal, including humans. According to this invention, mammals are treated by the pharmaceutically acceptable administration of an E2-derived peptide or peptidomimetic (herein collectively "E2 peptidomimetic) or other small molecule inhibitor of E2 function, either directly or by gene transfer techniques, to reduce the symptoms of the specific papillomavirus-associated disease, or to prevent their recurrence.

As discussed above, the papillomaviruses (PV) are infectious agents that can cause benign epithelial tumors, or warts, in their natural hosts. Infection with specific human papillomaviruses (HPV) is also associated with human epithelial malignancies, including malignancies of the uterine cervix, genitalia, skin and, though less frequently, other sites.

Figure 6:
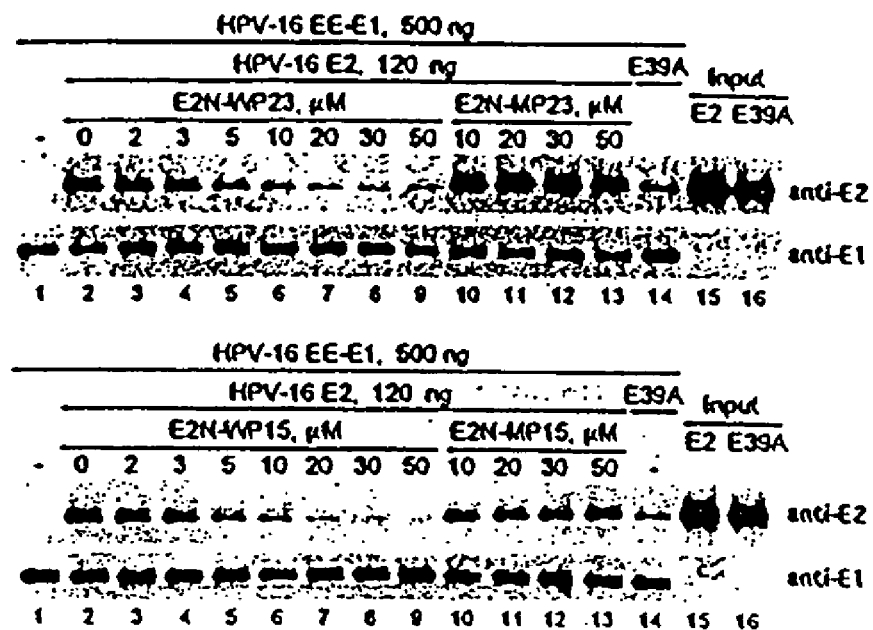
FIG. 6, Panels A and B. Peptides derived from the HPV16 E2 amino terminus inhibit in vitro interaction between HPV16 E1 and E2. A. Indicated amounts of epitope tagged HPV16 E1 (EE-E1) and HPV16 E2 were incubated in NET-gel buffer in the presence of increasing concentrations of the 23-mer (E2N-WP23; upper panel lanes 2–9) of the 15-mer (E2N-WP15; lower panel lanes 2–9). Binding of EE-E1 to E2 was determined by immunoprecipitation using an anti-EE epitope monoclonal antibody, and E2 was detected using anti-HPV16 E2C antiserum (31). Precipitation of E1 in each reaction was confirmed by probing the same blot with polyclonal antisera recognizing HPV16 E1. Increasing amounts of E2N-MP23 and E2N-MP15 peptides were used in lanes 10–13 (upper and lower panels). Lane 14 represents the level of interaction observed between the HPV16 E39A mutant protein and EE-E1. Input wild type and E39A mutant HPV16 E2 proteins are shown in lanes 15 and 16. B. Phosphorimager quantitation of the E2 reactive bands from the experiments shown in panel A.
Figure 6:
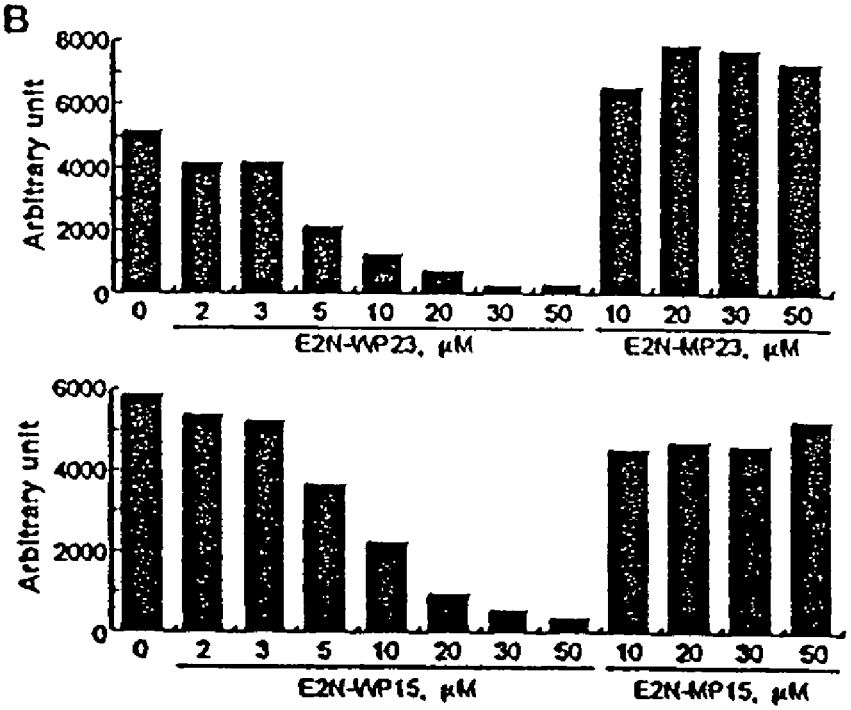
Figure 7:
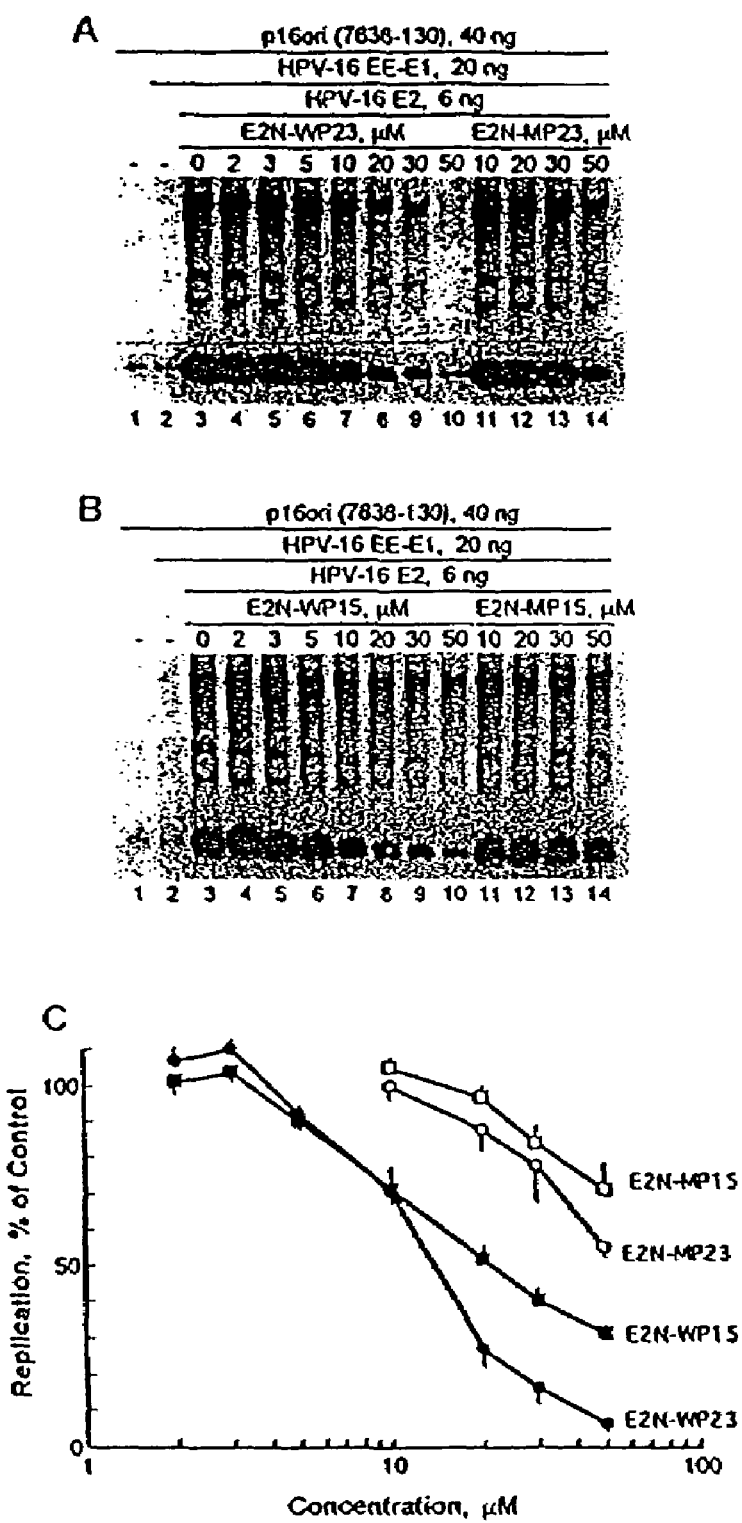
FIG. 7, Panels A, B and C. Peptides derived from the HPV16 E2 amino terminus inhibit replication of HPV16 in vitro. A and B. In vitro replication of HPV16 DNA replication was determined using 40 ng EE-E1 and 6 ng HPV16 E2 in the presence of increasing amounts of E2N-WP23 or E2N-WP15 (FIGS. 7A and 7B, respectively). Negative controls included reactions with only 293 cell extract and p16ori (lane 1, 7A and 7B), EE-E1 in the absence of E2 (lane 2, A and B), or complete replication reactions containing increasing concentrations of E2N-WP23 and E2NWP15 (FIGS. 7A and B, lanes 11–14). C. Phosphorimager quantitation of the replication experiments shown in FIGS. 7A and B. The amount of replication relative to that in lanes 3, in the absence of inhibitory peptide, is plotted logarithmically as a function of peptide concentration.
Figure 8:
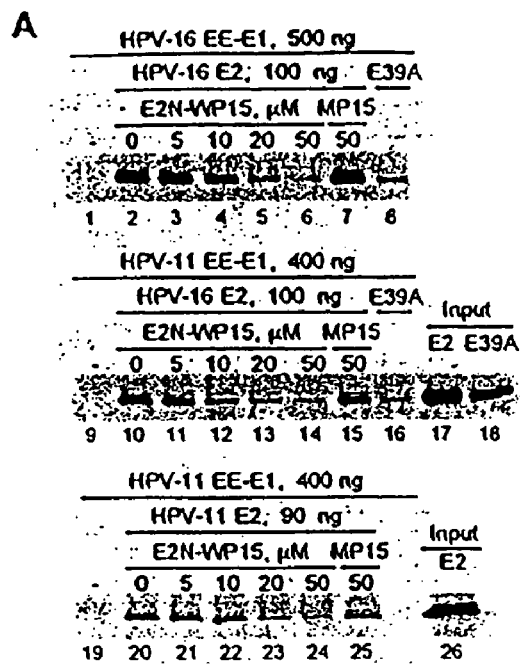
FIG. 8, Panels A, B and C. E2N-WP15 inhibits E1–E2 interaction and in vitro DNA replication of HPV11. A. Inhibition of E1–E2 interaction was compared between HPV16 E1 and HPV16 E2 (lanes 1–8), HPV11 E1 and HPV16 E2 (lanes 9–18), and between HPV11 E1 and HPV11 E2 (lanes 19–26). Epitope tagged E1 proteins were precipitated using anti-EE epitope monoclonal antibody, and associated E2 proteins were detected by Western blot using anti-E2 antiserum. Negative control reactions containing EE-E1 with no E2 are shown in lanes 1, 9, and 19. The amounts of input HPV16 E2 and E39A used in lanes 1–16 are shown in lanes 17 and 18. The input amount of E2 used in the HPV11 E2 experiment (lanes 19–25) is shown in lane 26. B. In vitro replication of the HPV11 origin plasmid p1 lori(7874–99) using increasing amounts of purified HPV11 EE-E1 in the presence (lanes 6–9) or absence (lanes 2–5) of 6ng HPV16 E2. The reaction in lane 1 contained no HPV proteins. C. The ability of E2N-WP15 to inhibit in vitro replication of the HPV11 or using HPV11 EE-E1 and HPV16 E2 was tested (lanes 4–8). Effects of equivalent concentrations of E2N-MP15 peptide were also determined (lanes 9-11).
Figure 8:
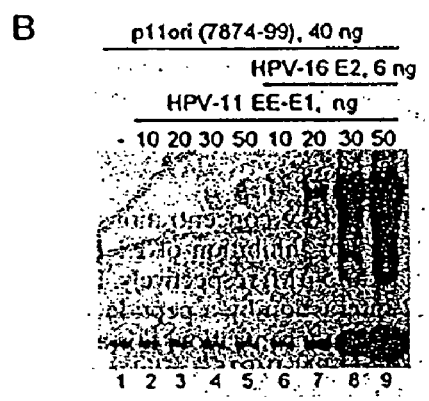
Figure 8:
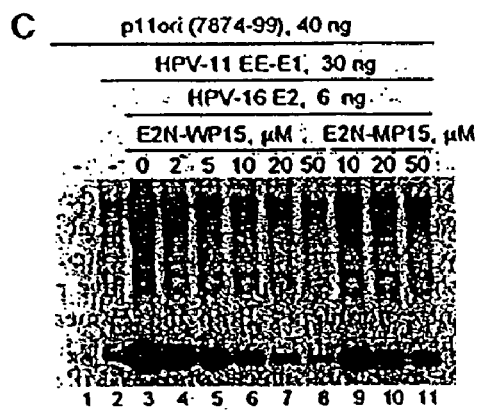

As described in the appended examples, and as shown in detail in FIGS. 6, 7, and 8, we have discovered that mutation of the conserved glutamic acid residue at position 39 of HPV16 E2 to alanine (E39A) disrupts its E1 interaction activity and its replication function in transient replication assays, but does not affect E2 transcriptional activation (Sakai et al. (1996) *J Virol* 70:1602–1611). This E39A mutation also disrupts replication activity of HPV16 E2 in HPV16 in vitro DNA replication. On this basis, we designed peptides derived from HPV16 E2 sequences flanking the E39 residue and tested the ability of these peptides to inhibit interaction between HPV16 E1 and E2 in vitro. The inhibitory activity of these peptides was specific, since analogous peptides that substituted alanine for the E39 residue did not inhibit interaction. The peptide E2N-WP15 (described below), for example, effectively inhibited HPV16 E1–E2 interaction. This peptide also inhibited in vitro replication of HPV16 DNA. The efficacy of E2N-WP15 was not exclusive to HPV16: this peptide also inhibited interaction of HPV11 E1 with the E2 proteins of both HPV11 and HPV16, and inhibited in vitro replication with these same combinations of E1 and E2 proteins. These results constitute the first demonstration that inhibition of E1–E2 interaction is sufficient to prevent HPV DNA replication in vitro.

In order to further define the E1–E2 interaction and design more efficient peptides peptidomimetics, an alanine scanning approach was used to determine specific residues within the E2N-WP15 peptide that are important for the inhibition of E1–E2 interaction. In general, for HPV-16 E2, residues R37, L38, E39, and I42 were found to be important for the inhibitory activity of the peptide for HPV-16. FIG. 12 depicts the alignment of conserved E39-proximal amino acid sequences, in which conserved residues are highlighted by the boxes. This further demonstrates the importance of R37 and E39 in the E1–E2 interaction, and together with the information obtained from HPV-16 E2, enables the development of core peptides and peptidomimetics to be used in the inhibition of the E1–E2 interaction, as described herein.

In preferred embodiments, the present invention provides a peptide, or peptidomimetic that inhibits the biological activity of the PV E2 protein, such as E2 dependent replications. The peptide/peptidomimetic can, in certain, preferred embodiments range in size from 3–25 amino acid residues. In certain embodiments, the E2 inhibitor of the present invention includes a core structure having the formula: R-X(4)-E-X(5)-X(6)-X(7) or a mimetic thereof. In certain other embodiments, the peptide may include a core structure having the formula: W-X(1)-X(2)-X(3)-R-X(4)-E-X(5)-X(6)-X(7)-X(8)-X(9)-X(10)-A-X(11), wherein:

W represents a tryptophan residue, or an analog thereof;
R represents an arginine residue, or an analog thereof;
E represents a glutamic acid residue, or an analog thereof;
A represents an alanine residue, or an analog thereof;
X(1) represents an amino acid residue having a polar sidechain, such as arg, asn, asp, cys, glu, gln, his, lys, ser, thr or tyr, or an analog thereof;
X(2), X(5), X(6), X(7) and X(8) each, independently, represent an amino acid residue having a neutral sidechain, such as ala, asn, cys, gin, gly, his, ile, leu, met, phe, pro, ser, thr, trp, tyr, or val, or an analog thereof;
X(3) represents an amino acid residue having a hydrophobic sidechain, such as ala, gly, ile, leu, met, phe, pro, trp, tyr, or an analog thereof;
X(4) and X(10) each, independently, represent an amino acid residue having a basic sidechain, such as arg, his or lys, or a neutral sidechain, such as ala, asn, cys, gin, gly, his, ile, leu, met, phe, pro, ser, thr, trp, tyr or val, or an analog thereof;
X(9) represents an amino acid residue having an aromatic sidechain, such as his, phe, trp or tyr, or an analog thereof; and
X(11) represents an amino acid residue having a basic sidechain, such as arg, his or lys, or an analog thereof.

It will also be appreciated that other core structures having a greater number of residues than the abovedescribed six membered core, and fewer residues than the above-described fifteen membered core, is also contemplated by the present invention.

In certain embodiments of the subject E2 peptidomimetic: X(1), X(2), X(3), X(9), X(10) and X(11) are as defined above; X(4) represents an amino acid residue having a basic sidechain or a neutral hydrophobic sidechain, such as ala, gly, ile, leu, met, phe, pro, trp, tyr or val, or an analog thereof; X(5) represents an amino acid residue having a neutral polar sidechain, such as asn, cys, gin, his, ser or thr, or an analog thereof; X(6) and X(7) each independently represent an amino acid residue having neutral aliphatic sidechain, such as ala, gly, ile, leu, or val, or an analog thereof; and X(8) represents an amino acid residue having a large hydrophobic sidechain, such ile, leu, met, phe, trp, or tyr or an analog thereof.

In preferred embodiments of the subject E2 peptidomimetic: X(1) represents gin, lys, tyr, cys or thr or an analog thereof, and more preferably gin, lys or cys or an analog thereof; X(2) represents leu, thr, cys, tyr, his, ala or cys or an analog thereof; X(3) represents met, leu, ile, val, thr or arg or an analog thereof, or an analog thereof, and more preferably met, leu, ile or val or an analog thereof; X(4) represents leu, lys, his, tyr, trp, arg, val, ile, met, gin or thr or an analog thereof, and even more preferably leu, lys, his, tyr, trp, arg, vat, ile or met or an analog thereof; X(5) represents gin, ala, ser, cys, asn or tyr or an analog thereof; X(6) represents ala, val or thr or an analog thereof, and even more preferably ala or val or an analog thereof; X(7) represents leu, ile or val or an analog thereof, and even more preferably leu or ile or an analog thereof; X(8) represents leu, tyr, phe, met or gln or an analog thereof; X(9) represents tyr, his or phe or an analog thereof, and even more preferably tyr or his or an analog thereof; X(10) represents lys, tyr, thr or ala or an analog thereof, and even more preferably lys or tyr or an analog thereof; and X(11) represents arg or lys or an analog thereof.

In other preferred embodiments, the peptide or peptidomimetic represents the six sequence core wherein X(4) represents leu, trp, gin, his, met, or thr, or an analog thereof; X(5) represents cys, asn, gin or ser, or an analog thereof; X(6) represents ala, val, or thr, or an analog thereof; and X(7) represents ile, leu, val, or met, or an analog thereof.

Moreover, Applicants believe that the subject peptides are the first example of any small molecule capable of inhibiting E1–E2 interaction. Prior to Applicants' discovery, there was no evidence to suggest that a small molecule would be capable of inhibiting that complex and thereby be useful for treatment of PV-related diseases. In fact, prior studies have actually suggested that multiple large domains were required for the necessary interaction (see, for example, Abroi, A., R. Kurg, and M. Ustav. 1996, J. Virol. 70: 6169–6179; Breiding, D. E., M. J. Grossel, and E. J. Androphy. 1996, Virology 221: 34–43; Grossel, M. J., F. Sverdrup, D. E. Breiding, and E. J. Androphy. 1996, J. Virol. 70: 7264–7269; Sakai, H., T. Yasugi, J. D. Benson, J. J. Dowhanick, and P. M. Howley. 1996, J. Virol. 70: 1602–1611; Winokur, P. L. and A. A. McBride. 1992. EMBO J. 11: 4111–4118). Thus, the present invention provides a general approach to the treatment of PV-related diseases utilizing peptidyl and non-peptidyl small molecule inhibitors of E1–E2 interaction.

II. Definitions

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_{1-C30}$ for straight chain, $C_{3-C30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

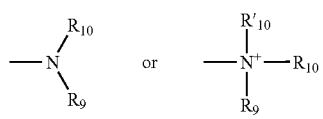

wherein R$_9$, R$_{10}$ and R'$_{10}$ each independently represent a hydrogen, an alkyl, an alkenyl, —(CH$_2$)$_m$—R$_8$, or R$_9$ and R$_{10}$ taken together with the N atom to which they are attached complete a heterocycle having from 4 to 8 atoms in the ring structure; R$_8$ represents an aryl, a cycloalkyl, a cycloalkenyl, a heterocycle or a polycycle; and m is zero or an integer in the range of 1 to 8. In preferred embodiments, only one of R$_9$ or R$_{10}$ can be a carbonyl, e.g., R$_9$, R$_{10}$ and the nitrogen together do not form an imide. In even more preferred embodiments, R$_9$ and R$_{10}$ (and optionally R'$_{10}$) each independently represent a hydrogen, an alkyl, an alkenyl, or —(CH$_2$)$_m$—R$_8$. Thus, the term "alkylamine" as used herein means an amine group, as defined above, having a substituted or unsubstituted alkyl attached thereto, i.e., at least one of R$_9$ and R$_{10}$ is an alkyl group.

The term "acylamino" is art-recognized and refers to a moiety that can be represented by the general formula:

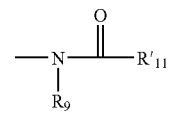

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

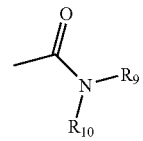

wherein R$_9$, R$_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

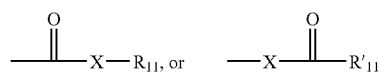

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R$_{11}$ is hydrogen, the formula represents a "formate". In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

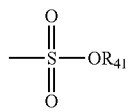

in which $R_{41}$ is an electron pair, hydrogen, alkyl, cycloalkyl, or aryl.

The term "sulfate" is art recognized and includes a moiety that can be represented by the general formula:

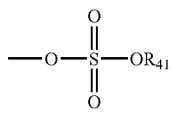

in which $R_{41}$ is as defined above.

The term "sulfonamido" is art recognized and includes a moiety that can be represented by the general formula:

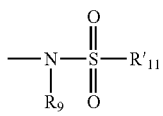

in which $R_9$ and $R'_{11}$ are as defined above.

The term "sulfamoyl" is art-recognized and includes a moiety that can be represented by the general formula:

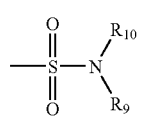

in which $R_9$ and $R_{10}$ are as defined above.

The term "sulfonyl", as used herein, refers to a moiety that can be represented by the general formula:

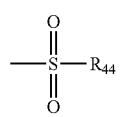

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

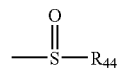

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

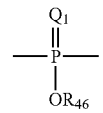

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

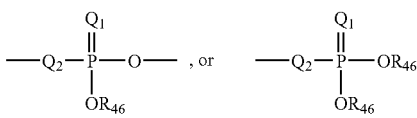

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

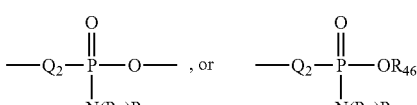

wherein $R_9$ and $R_{10}$ are as defined above, and $Q_2$ represents O, S or N.

A "phosphonamidite" can be represented in the general formula:

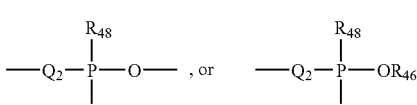

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se-$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P.G.M. *Protective Groups in Organic Synthesis*, 2$^{nd}$ ed.; Wiley: New York, 1991).

The term "amino acid residue" is known in the art. In general the abbreviations used herein for designating the amino acids and the protecting groups are based on recommendations of the IUPAC-IUB Commission on Biochemical Nomenclature (see Biochemistry (1972) 11:1726–1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers. D- and L-α-Amino acids are represented by the following Fischer projections and wedge-and-dash drawings. In the majority of cases, D- and L-amino acids have R- and S-absolute configurations, respectively.

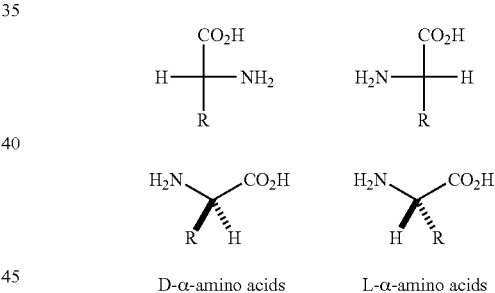

D-α-amino acids    L-α-amino acids

A "reversed" or "retro" peptide sequence as disclosed herein refers to that part of an overall sequence of covalently-bonded amino acid residues (or analogs or mimetics thereof) wherein the normal carboxyl to amino direction of peptide bond formation in the amino acid backbone has been reversed such that, reading in the conventional left-to-right direction, the amino portion of the peptide bond precedes (rather than follows) the carbonyl portion. See, generally, Goodman, M. and Chorev, M. *Accounts of Chem. Res.* 1979, 12, 423.

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). A peptide (amide) bond cannot be formed at the interface between a normal orientation residue and a reverse orientation residue.

Therefore, certain reversed peptide compounds of the invention can be formed by utilizing an appropriate amino acid mimetic moiety to link the two adjacent portions of the sequences depicted above utilizing a reversed peptide (reversed amide) bond. In case (a) above, a central residue of a diketo compound may conveniently be utilized to link structures with two amide bonds to achieve a peptidomimetic structure. In case (b) above, a central residue of a diamino compound will likewise be useful to link structures with two amide bonds to form a peptidomimetic structure.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is preferably (D), and the configuration of the non-reversed portion is preferably (L). Opposite or mixed configurations are acceptable when appropriate to optimize a binding activity.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g. the ability to bind to opioid receptors), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures. Thus, the contemplated equivalents include small molecule inhibitors of the E1–E2 infections which, e.g., bind either E1 or E2. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "transfection" means the introduction of a nucleic acid, e.g., an expression vector, into a recipient cell by nucleic acid-mediated gene transfer.

"Transcriptional regulatory sequence" is a generic term used throughout the specification to refer to DNA sequences, such as initiation signals, enhancers, and promoters, which induce or control transcription of protein coding sequences with which they are operably linked.

Operably linked is intended to mean that the nucleotide sequence is linked to a regulatory sequence in a manner which allows expression of the nucleotide sequence. Regulatory sequences are art-recognized and are selected to direct expression of the subject peptide. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990).

The term "gene construct" refers to a vector, plasmid, viral genome or the like which includes a coding sequence, can transfect cells, preferably mammalian cells, and can cause expression of the E2 for an E2 peptide of the cells transfected with the construct. The term "gene construct" does not include a wild-type papillomavirus genome, and preferably does not include expressible coding sequences for one or more of a papillomavirus E6 or E7 proteins.

As used herein, the term "pharmaceutically acceptable" refers to a carrier medium which does not interfere with the effectiveness of the biological activity of the active ingredients and which is not excessively toxic to the hosts of the concentrations of which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

As used herein, the term "prophylactic or therapeutic" treatment refers to administration to the host of the papillomavirus medicament. If it is administered prior to exposure to the virus, the treatment is prophylactic (i.e., it protects the host against infection), whereas if administered after infection or initiation of the disease, the treatment is therapeutic (i.e., it combats the existing infection or cancer).

As used herein the term "papillomavirus disease" refers to any kind of infection or disorder caused by the virus, including cancers and warts. Thus, the term includes symptoms and side effect of any papillomavirus infection, including latent, persistent and sub-clinical infections, whether or not the infection is clinically apparent.

The term "cell-proliferative disorder" denotes malignant as well as nonmalignant cell populations which morphologically often appear to differ from the surrounding tissue.

III. Methods of Treatment

Diseases which may be prevented and/or treated by the processes and compositions of this invention are those caused by the etiological agent, papillomavirus, and may be the result of clinical or sub-clinical PV infections. Such diseases include, for example, epithelial malignancies, anogenital malignancies, such as cervical cancer, malignant lesions, benign lesions, papillomacarcinomas, papilloadeno-cystomas, papilloma neurophathicum, papillomatosis, cutaneous and mucosal papillomas, condylomas, oral, pharyngeal, laryngeal, and tongue papillomas, fibroblastic tumors and other pathological conditions associated with papillomavirus. The E2 inhibitors of this invention may also be used to treat epithelial and internal fibropapillomas in animals.

In addition, as described above, a wide variety of warts are found on human skin and are caused by the human papillomavirus (HPV). For example, the following types of warts are found on human skin and are caused by the human papillomavirus (HPV): common warts (verruca vulgaris), plantar warts, palmar warts, planar warts (verruca plana), mosaic warts, and venereal warts (condyloma accuminatum). These skin growths are unsightly, irritating, and potentially oncogenic (carcinogenic), and their removal is desired.

Genital warts, also referred to as venereal warts and condylomata acuminata, are one of the most serious manifestations of HPV infection. As reported by the Center for Disease Control, the sexual mode of transmission of genital warts is well established and the incidence of genital warts is on the increase. The seriousness of genital warts is underlined by the finding that HPV DNA can be found in all grades of cervical intraepithelial neoplasia (CIN I–III) and that a specific subset of HPV types can be found in carcinoma in situ of the cervix. Consequently, women with genital warts, containing specific HPV types are now considered at high risk for the development of cervical cancer. Current treatments for genital warts are inadequate. According to the present invention, a method of treating a patient having one or more genital warts comprises the administration of a pharmaceutical composition including an E2 peptidomimetic, or a gene construct encoding an E2 peptide including E39, so as to inhibit growth of the wart. In preferred embodiments, the wart(s), or other PV-containing cells, are contacted directly with the pharmaceutical composition. The subject method can be used to treat, e.g., condyloma acuminata and/or flat cervical warts.

Laryngeal papillomas are benign epithelial tumors of the larynx. Two PV types, HPV-6 and HPV-11, are most commonly associated with laryngeal papillomas. According to the method of the present invention, laryngeal papillomas are treated administrating a pharmaceutical composition including the therapeutic E2 peptidomimetic, or a gene construct encoding an E2-derived peptide, so as to inhibit growth of the papillomas.

The most common disease associated with papillomavirus infection are benign skin warts. Common warts generally contain HPV types 1, 2, 3, 4 or 10. These warts typically occur on the soles of feet, plantar warts, or on the hands. Common skin warts are most often found in children and young adults. Later in life the incidence of common warts decreases presumably due to immunologic and physiologic changes. Plantar warts can often be debilitating and require surgical removal and they frequently reoccur after surgery. As above, patients suffering from common warts can be treated by the administration of a effective amount of an E2 peptidomimetic according to the present invention, or a gene therapy construct which encodes the therapeutic E2 peptide. In preferred embodiments, the peptide or gene construct are applied, in the appropriate formulations, directly to the area of the skin afflicted with the wart(s). Similar methods and compositions may be useful in the treatment if epidermodysplasia verruciformis (EV), a rare genetically transmitted disease which is characterized by disseminated flat warts that appear as small reddish macules.

In addition, the subject method and compositions may be used to treat lesions resulting from cellular transformation for which HPV is a etiological agent, e.g., in the treatment of cervical cancer.

IV. Exemplary Drug Screening Assays

A variety of drug screening techniques can be readily adapted to the E1–E2 interaction in order to provide high throughput screening of peptide, peptidomimetic or other small molecule libraries. Such assays can be used to optimize a lead compound, or to assess the potential PV inhibitory effect of a test compound.

In one embodiment, simple competition assays can be used to assess the ability of a test compound to disrupt the interaction of an E1–E2 complex. In other embodiments, cell-based assays which detect PV replication or Papilloma virus replication can be used to assess the biological activity of a test compound.

V. Exemplary Compositions

In certain embodiments of the present invention, such as for topical administration to the epidermis, the subject E2 pharmaceutical can be a peptide, e.g., having a naturally occurring peptide backbone and amino acid side chains, though it may be N-terminally and/or C-terminally protected.

In preferred embodiments, the peptidyl component of the subject compounds includes, in addition to the core E2 sequences, as described herein, no more than about 25 amino acid residues of a protein in which an E2 motif naturally exists, more preferably no more than 10–15, and even more preferably 6 or less. With the exception of certain chimeric E2 compositions described herein, such as fusion proteins, a preferred composition (especially for ectopic application) includes a peptide comprising an E2 core motif and having a molecular weight in the range of about 1500 to 7500 daltons, more preferably from about 2000 to 5000 daltons, and even more preferably in the range of about 2000 to 2750 daltons. The peptide, in addition to the E2 core motif, may include other amino acid residues, such as a transcytosis peptide, and may be derivatized at one or more backbone or sidechain points with, e.g. peptides, nucleic acids, carbohydrates, etc. In certain embodiments, the peptide is derivatized with one or more functional groups that enhance cellular uptake and/or impair the half-life of the E2 core motif.

This invention further contemplates a method of generating sets of combinatorial libraries of the subject E2 peptides which is especially useful for identifying potential variant sequences (e.g. homologs) that are functional in inhibiting E1–E2 interactions. Combinatorially-derived homologs can be generated which have, e.g., greater affinity, a enhanced potency relative to native E2 peptide sequences, or intracellular half-lives different than the corresponding wild-type E2 peptide. For example, the altered peptide can be rendered either more stable or less stable to proteolytic degradation or other cellular process which result in destruction of, or otherwise inactivation of, the peptide. Such homologs can be utilized to alter the envelope of therapeutic application by modulating the half-life of the peptide. For instance, a short half-life can give rise to more transient biological effects and can allow tighter control of peptide levels within the cell.

In a representative embodiment of this method, the amino acid sequences for a population of E2 motifs are aligned, preferably to promote the highest homology possible. Such a population of variants can include, for example, E2 peptides from both high and low risk human papillomaviruses, as well as PV from other animals. Amino acids which appear at each position of the aligned sequences are selected to create a degenerate set of combinatorial sequences. To illustrate, as set out above inspection of E2 sequences reveals a consensus sequence (see FIGS. 5A and 5B). Similarly, FIG. 12 reveals a shorter consensus sequence based upon critical binding residues. Based on these alignments, combinatorial libraries can be generated from this portion of E2 peptides so as to have an amino acid sequence that includes an E2 core sequence represented by the formula:
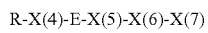
R- cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for E2 homologs which can then be screened for further PV inhibitory activities. Subsequent selection, e.g. of a reduced set of variants from the library, may then be based upon more meaningful criteria rather than simple E1-binding ability. For instance, intracellular half-life or selectivity can become selection criteria in secondary screens.

Combined with certain formulations, such peptides can be effective intracellular agents for, e.g., inhibiting PV infection of epithelial cells. However, in order to increase the efficacy of such peptides, the E2 peptide can be provided a fusion peptide along with a second peptide which promotes "transcytosis", e.g., uptake of the peptide by epithelial cells. To illustrate, the E2 peptide of the present invention can be provided as part of a fusion polypeptide with all or a fragment of the N-terminal domain of the HIV protein Tat, e.g., residues 1–72 of Tat or a smaller fragment thereof which can promote transcytosis. In other embodiments, the E2 peptide can be provided a fusion polypeptide with all or a portion of the antenopedia III protein.

To further illustrate, the E2 peptide (or peptidomimetic) can be provided as a chimeric peptide which includes a heterologous peptide sequence ("internalizing peptide") which drives the translocation of an extracellular form of a E2 peptide sequence across a cell membrane in order to facilitate intracellular localization of the E2 peptide. In this regard, the therapeutic E2 sequence is one which is active intracellularly. The internalizing peptide, by itself, is capable of crossing a cellular membrane by, e.g., transcytosis, at a relatively high rate. The internalizing peptide is conjugated, e.g., as a fusion protein, to the E2 peptide. The resulting chimeric peptide is transported into cells at a higher rate relative to the activator polypeptide alone to thereby provide an means for enhancing its introduction into cells to which it is applied, e.g., to enhance topical applications of the E2 peptide.

In one embodiment, the internalizing peptide is derived from the *Drosophila* antennapedia protein, or homologs thereof. The 60 amino acid long long homeodomain of the homeo-protein antennapedia has been demonstrated to translocate through biological membranes and can facilitate the translocation of heterologous polypeptides to which it is couples. See for example Derossi et al. (1994) *J Biol Chem* 269:10444–10450; and Perez et al. (1992) *J Cell Sci* 102: 717–722. Recently, it has been demonstrated that fragments as small as 16 amino acids long of this protein are sufficient to drive internalization. See Derossi et al. (1996) *J Biol Chem* 271:18188–18193.

The present invention contemplates an E2 peptide or peptidomimetic sequence as described herein, and at least a portion of the Antennapedia protein (or homolog thereof) sufficient to increase the transmembrane transport of the chimeric protein, relative to the E2 peptide or peptidomimetic, by a statistically significant amount. As discussed in the Exemplification, fusion peptides were tested for their ability to inhibit HPV-16 E1–E2 interaction in vitro. FIG. 14 depicts the inhibition of Ant-WP peptide at levels comparable to that of wild-type peptide. The similar inhibition of the E39A counterpart is also contemplated.

Another example of an internalizing peptide is the HIV transactivator (TAT) protein. This protein appears to be divided into four domains (Kuppuswamy et al. (1989) *Nucl. Acids Res.* 17:3551–3561). Purified TAT protein is taken up by cells in tissue culture (Frankel and Pabo, (1989) *Cell* 55:1189–1193), and peptides, such as the fragment corresponding to residues 37–62 of TAT, are rapidly taken up by cell in vitro (Green and Loewenstein, (1989) *Cell* 55:1179–1188). The highly basic region mediates internalization and targeting of the internalizing moiety to the nucleus (Ruben et al., (1989) *J. Virol.* 63:1–8).

Another exemplary transcellular polypeptide can be generated to include a sufficient portion of mastoparan (T. Higashijima et al., (1990) *J. Biol. Chem.* 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefor serve as an internalizing peptide for the subject transcellular peptides and peptidomimetics. Preferred growth factor-derived internalizing peptides include EGF (epidermal growth factor)-derived peptides, such as CMHIESLDSYTC and CMYIEALDKYAC; TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0–5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of E2 peptides and peptidomimetics, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5–7, so that a sufficient uncharged membrane-binding domain will be present within the peptide at pH 5 to allow insertion into the target cell membrane.

A particularly preferred pH-dependent membrane-binding internalizing peptide in this regard is aa1-aa2-aa3-EAALA$(EALA)_4$-EALEALAA-amide, which represents a modification of the peptide sequence of Subbarao et al. (*Biochemistry* 26:2964, 1987). Within this peptide sequence, the first amino acid residue (aa1) is preferably a unique residue, such as cysteine or lysine, that facilitates chemical conjugation of the internalizing peptide to a targeting protein conjugate. Amino acid residues 2–3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2–3 are neutral amino acids, the internalizing peptide will insert into neutral membranes.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the E2 peptide or peptidomimetic, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (Eubanks et al., in: *Peptides, Chemistry and Biology*, Garland Marshall (ed.), ESCOM, Leiden, 1988, pp. 566–69) In this construct, an internalizing peptide would be attached to the C-terminus of the accessory peptide, since the N-terminal glycine is critical for the accessory moiety's activity. This hybrid peptide, upon attachment to an E2 peptide or peptidomimetic at its C-terminus, is N-myristylated and further anchored to the target cell membrane, e.g., it serves to increase the local concentration of the peptide at the cell membrane.

To further illustrate use of an accessory peptide, a phosphorylatable accessory peptide is first covalently attached to the C-terminus of an internalizing peptide and then incorporated into a fusion protein with an E2 peptide or peptidomimetic. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the polypeptide into the cell cytoplasm.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) *Ann. Rev. Biochem.* 56:63–87). Accessory peptides that contain the sequence x-NLT-x thus will enhance target cell retention of corresponding polypeptide.

In another embodiment of this aspect of the invention, an accessory peptide can be used to enhance interaction of the E2 peptide or peptidomimetic with the target cell. Exemplary accessory peptides in this regard include peptides derived from cell adhesion proteins containing the sequence "RGD", or peptides derived from laminin containing the sequence CDPGYIGSRC. Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bi of complement, von-Willebrand factor, EGF receptor, transforming growth factor beta, collagen type I, lambda receptor of *E. Coli*, fibrinogen and Sindbis coat protein (E. Ruoslahti, *Ann. Rev. Biochem.* 57:375–413, 1988). Cell surface receptors that recognize RGD sequences have been grouped into a superfamily of related proteins designated "integrins". Binding of "RGD peptides" to cell surface integrins will promote cell-surface retention, and ultimately translocation, of the polypeptide.

As described above, the internalizing and accessory peptides can each, independently, be added to E2 peptide or peptidomimetic by either chemical cross-linking or in the form of a fusion protein. In the instance of fusion proteins, unstructured polypeptide linkers can be included between each of the peptide moieties.

In general, the internalization peptide will be sufficient to also direct export of the polypeptide. However, where an accessory peptide is provided, such as an RGD sequence, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein.

In an exemplary embodiment, an E2 peptide or peptidomimietic is engineered to include an integrin-binding RGD peptide/SV40 nuclear localization signal (see, for example Hart SL et al., 1994; J. Biol. Chem., 269:12468–12474), such as encoded by the nucleotide sequence provided in the Nde1-EcoR1 fragment: catatgggtggctgccgtggcgatatgt-tcggttgcggtgctcctccaaaaaagaagagaaag-gtagctggattc, which encodes the RGD/SV40 nucleotide sequence: MGGCRGD-MFGCGAPP-KKKRKVAGF. In another embodiment, the protein can be engineered with the HIV-1 tat(1–72) polypeptide, e.g., as provided by the Nde1-EcoR1 fragment:catatg-gagccagtagatcctagactagagccctggaagcatccaggaagtcagcctaaa-actgcttgtaccaattgctattgtaaaaagtgttgctttcattgccaagtttgtttcata-acaaagcccttggcatctcctatggcaggaagaagcggagacagcgacgaaga-cctcctcaaggcagtcagactcatcaagtttctctaagtaagcaaggattc, which encodes the HIV-1 tat(1–72) peptide sequence: MEPVD-PRLEPWKHPGSQPKTACTNCYCKKCCFHCQVCFIT-KALGISYGRKKRRQRRRPPQGSQTHQVSLSKQ. In still another embodiment, the fusion protein includes the HSV-1 VP22 polypeptide (Elliott G., O'Hare P (1997) Cell, 88:223–233) provided by the Nde1-EcoR1 fragment: cat atg acc tct cgc cgc tcc gtg aag tcg ggt ccg cgg gag gtt ccg cgc gat gag tac gag gat ctg tac tac acc ccg tct tca ggt atg gcg agt ccc gat agt ccg cct gac acc tcc cgc cgt ggc gcc cta cag aca cgc tcg cgc cag agg ggc gag gtc cgt ttc gtc cag tac gac gag tcg gat tat gcc ctc tac ggg ggc tcg tca tcc gaa gac gac gaa cac ccg gag gtc ccc cgg acg cgg cgt ccc gtt tcc ggg gcg gtt ttg tcc ggc ccg ggg cct gcg cgg gcg cct ccg cca ccc gct ggg tcc gga ggg gcc gga cgc aca ccc acc acc gcc ccc cgg gcc ccc cga acc cag cgg gtg gcg act aag gcc ccc gcg gcc ccg gcg gcg gag acc acc cgc ggc agg aaa tcg gcc cag cca gaa tcc gcc gca ctc cca gac gcc ccc gcg tcg acg gcg cca acc cga tcc aag aca ccc gcg cag ggg ctg gcc aga aag ctg cac ttt agc acc gcc ccc cca aac ccc gac gcg cca tgg acc ccc cgg gtg gcc ggc ttt aac aag cgc gtc ttc tgc gcc gcg gtc ggg cgc ctg gcg gcc atg cat gcc cgg atg gcg gcg gtc cag ctc tgg gac atg tcg cgt ccg cgc aca gac gaa gac ctc aac gaa ctc ctt ggc atc acc acc atc cgc gtg acg gtc tgc gag ggc aaa aac ctg ctt cag cgc gcc aac gag ttg gtg aat cca gac gtg gtg cag gac gtc gac gcg gcc acg gcg act cga ggg cgt tct gcg gcg tcg cgc ccc acc gag cga cct cga gcc cca gcc cgc tcc gct tct cgc ccc aga cgg ccc gtc gag gaa ttc which encodes the HSV-1 VP22 peptide having the sequence:

MTSRRSVKSGPREVPRDEYEDLYYTPSSGMASDSPPDTSRRGALQT

RSRQRGEVRFVQYDESDYALYGGSSSEDDEHPEVPRTRRPVSGAVLSGPG

PARAPPPPAGSGGAGRTPTTAPRAPRTGRVATKAPAAPAAETTRGRKSAQ

PESAALPDAPASTAPTRSKTPAQGLARKLHFSTAPPNPDAPWTPRVAGFN

KRVFCAAVGRLAAMHARMAAVQLWDMSRPRTDEDLNELLGITTIRVTVCE

GKNLLQRANELVNPDVVQDVDAATATRGRSAASRPTERPRAPARSASRPR

RPVE

In still another embodiment, the fusion protein includes the C-terminal domain of the VP22 protein from, e.g., the nucleotide sequence (Nde1-EcoR1 fragment): cat atg gac gtc gac gcg gcc acg gcg act cga ggg cgt tct gcg gcg tcg cgc ccc acc gag cga cct cga gcc cca gcc cgc tcc gct tct cgc ccc aga cgg ccc gtc gag gaa ttc which encodes the VP22 (C-terminal domain) peptide sequence:

MDVDAATATRGRSA-ASRPTERPRAPARSASRPRRPVE

In certain instances, it may also be desirable to include a nuclear localization signal as part of the E2 peptide.

In the generation of fusion polypeptides including the subject E2 peptides, it may be necessary to include unstructured linkers in order to ensure proper folding of the various peptide domains, and prevent steric or other inteference of the heterologous domains with the PV inhibitory activity of the E2 peptide. Many synthetic and natural linkers are known in the art and can be adapted for use in the present invention, including the $(Gly_3Ser)_4$ linker.

In other embodiments, the subject E2 therapeutics are peptidomimetics of the E2 peptide. Peptidomimetics are compounds based on, or derived from, peptides and proteins. The E2 peptidomimetics of the present invention typically can be obtained by structural modification of a known E2 peptide sequence using unnatural amino acids, conformational restraints, isosteric replacement, and the like. The subject peptidomimetics constitute the continuum of structural space between peptides and non-peptide synthetic structures; E2 peptidomimetics may be useful, therefore, in delineating pharmacophores and in helping to translate peptides into nonpeptide compounds with the activity of the parent E2 peptides.

Moreover, as is apparent from the present disclosure, mimetopes of the subject E2 peptides can be provided. Such peptidomimetics can have such attributes as being non-hydrolyzable (e.g., increased stability against proteases or other physiological conditions which degrade the corresponding peptide), increased specificity and/or potency for inhibition of PV replication, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p123), C-7 mimics (Huffman et al. in Peptides: Chemistry and Biologyy, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), β-aminoalcohols (Gordon et al. (1985) Biochem Biophys Res Commun126:419; and Dann et al. (1986) Biochem Biophys Res Commun 134:71), diaminoketones (Natarajan et al. (1984) Biochem Biophys Res Commun 124:141), and methyleneamino-modifed (Roark et al. in Peptides: Chemistry and Biology, G. R. Marshall ed., ESCOM Publisher: Leiden, Netherlands, 1988, p134). Also, see generally, Session III: Analytic and synthetic methods, in in Peptides: Chemistry and Biology, G. R. Marshall ed., ESCOM Publisher: Leiden, Netherlands, 1988).

In addition to a variety of sidechain replacements which can be carried out to generate the subject E2 peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

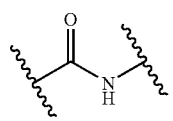
amide bond

EXAMPLES OF SURROGATES

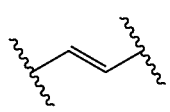  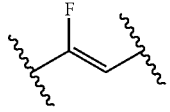  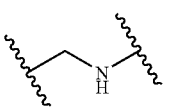

trans olefin    fluoroalkene    methyleneamino

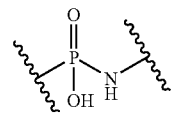  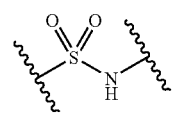

phosphoamide    sulfonamide

Additionally, peptidomimietics based on more substantial modifications of the backbone of the E2 peptide can be used. Peptidomimetics which fall in this category include (i) retro-inverso analogs, and (ii) N-alkyl glycine analogs (so-called peptoids).

dipeptide

EXAMPLES OF ANALOGS retro-inverso

N-alkyl glycine

Furthermore, the methods of combinatorial chemistry are being brought to bear, e,g, by G. L. Verdine at Harvard University, on the development of new peptidomimetics. For example, one embodiment of a so-called "peptide morphing" strategy focuses on the random generation of a library of peptide analogs that comprise a wide range of peptide bond substitutes.

dipeptide

↓ peptide morphing

In

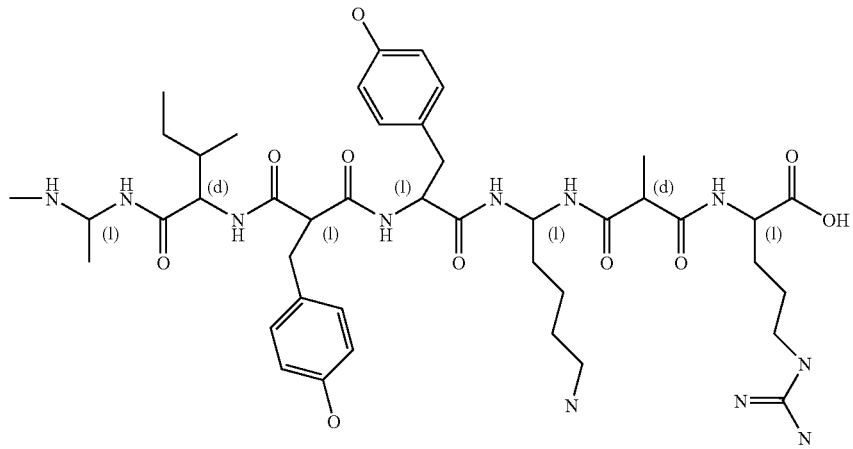

Such retro-inverso analogs can be made according to the methods known in the art, such as that described by the Sisto et al. U.S. Pat. No. 4,522,752. For example, the illustrated retro-inverso analog can be generated as follows. The geminal diamine corresponding to the N-terminal tryptophan is synthesized by treating a protected tryptophan analog with ammonia under HOBT-DCC coupling conditions to yield the N-Boc amide, and then effecting a Hofmann-type rearrangement with I,I-bis-(trifluoroacetoxy)iodobenzene (TIB), as described in Radhakrishna et al. (1979) *J. Org. Chem.* 44:1746. The product amine salt is then coupled to a side-chain protected (e.g., as the benzyl ester) N-Fmoc D-lys residue under standard conditions to yield the pseudodipeptide. The Fmoc (fluorenylmethoxycarbonyl) group is removed with piperidine in dimethylformamide, and the resulting amine is trimethylsilylated with bistrimethylsilylacetamide (BSA) before condensation with suitably alkylated, side-chain protected derivative of Meldrum's acid, as described in U.S. Pat. No. 5,061,811 to Pinori et al., to yield the retro-inverso tripeptide analog WKH. The pseudotripeptide is then coupled with with an L-methionine analog under standard conditions to give the protected tetrapeptide analog. The protecting groups are removed to release the product, and the steps repeated to enlogate the tetrapeptide to the full length peptidomimetic. It will be understood that a mixed peptide, e.g. including some normal peptide linkages, will be generated. As a general guide, sites which are most susceptible to proteolysis are typically altered, with less susceptible amide linkages being optional for mimetic switching The final product, or intermediates thereof, can be purified by HPLC.

In another illustrative embodiment, the peptidomimetic can be derived as a retro-enatio analog of the peptide, such as the exemplary retro-enatio peptide analog derived for the illustrative WKHMRLECAIYYKAR peptide:

NH$_2$-(d)Arg-(d)Ala-(d)Lys-(d)Tyr-(d)Tyr-(d)Ile-(d)Ala-(d)Cys-(d)Glu-(d)Leu-(d)Arg-(d)Met-(d)His-(d)Lys-(d)Trp-COOH

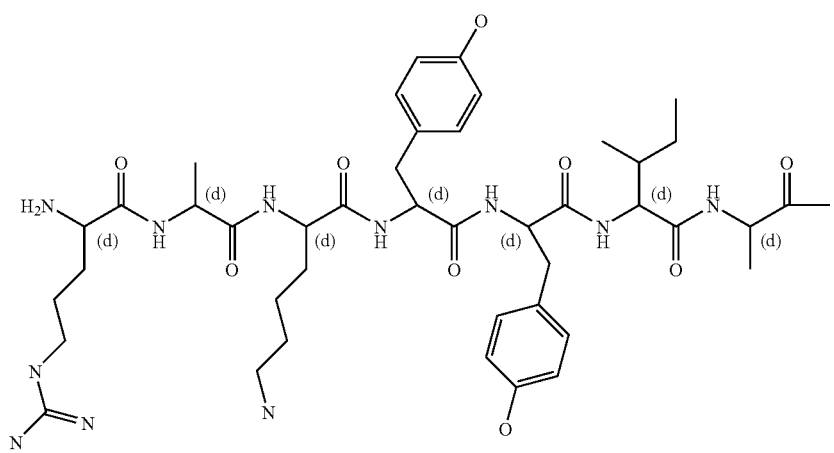

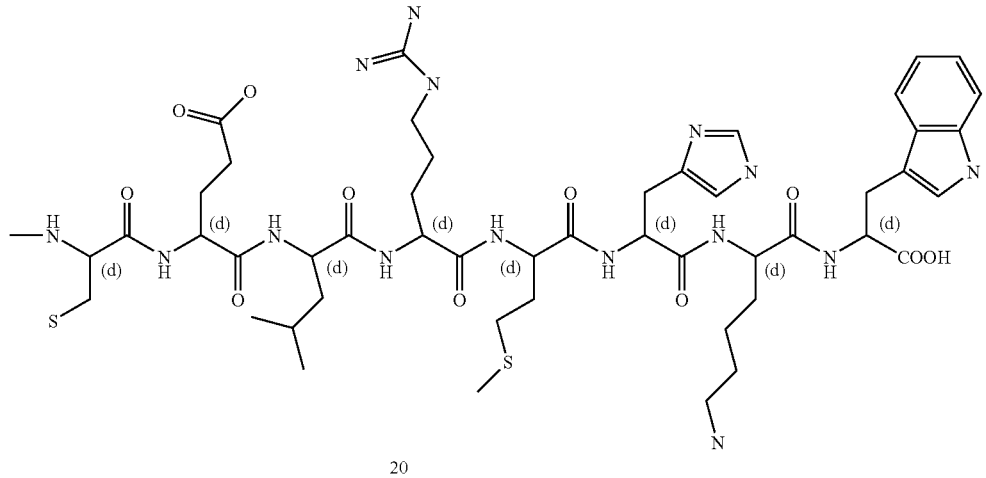

20

Retro-enantio analogs such as this can be synthesized commercially available D-amino acids (or analogs thereof) and standard solid- or solution-phase peptide-synthesis techniques. For example, in a preferred solid-phase synthesis method, a suitably amino-protected (t-butyloxycarbonyl, Boc) D-trp residue (or analog thereof) is covalently bound to a solid support such as chloromethyl resin. The resin is washed with dichloromethane (DCM), and the BOC protecting group removed by treatment with TFA in DCM. The resin is washed and neutralized, and the next Boc-protected D-amino acid (D-lys) is introduced by coupling with diisopropylcarbodiimide. The resin is again washed, and the cycle repeated for each of the remaining amino acids in turn (D-his, D-met, etc). When synthesis of the protected retro-enantio peptide is complete, the protecting groups are removed and the peptide cleaved from the solid support by treatment with hydrofluoric acid/anisole/dimethyl sulfide/thioanisole. The final product is purified by HPLC to yield the pure retro-enantio analog.

In still another illustrative embodiment, trans-olefin derivatives can be made for the subject polypeptide. For example, an exemplary olefin analog is derived for the illustrative WKHMRLECAIYYKAR peptide:

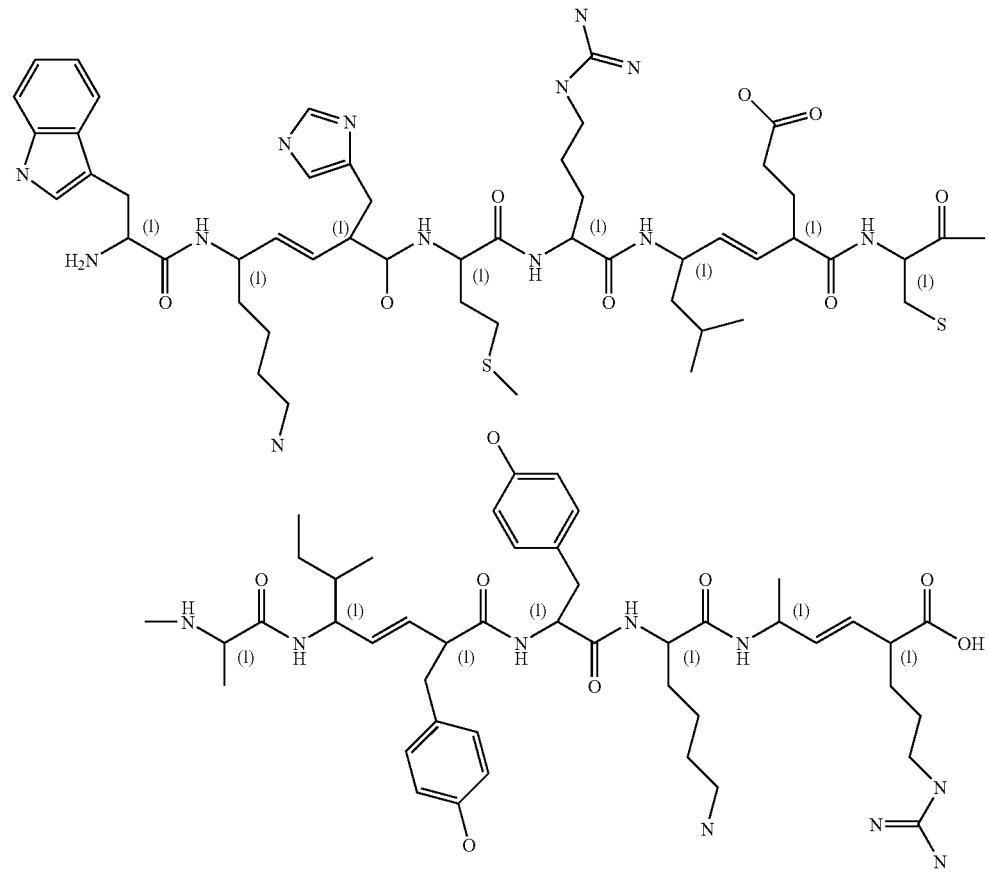

The trans olefin analog of an E2 peptide can be synthesized according to the method of Y. K. Shue et al. (1987) *Tetrahedron Letters* 28:3225. Referring to the illustrated example, Boc-amino L-Ile is converted to the corresponding α-amino aldehyde, which is treated with a vinylcuprate to yield a diastereomeric mixture of alcohols, which are carried on together. The allylic alcohol is acetylated with acetic anhydride in pyridine, and the olefin is cleaved with osmium tetroxide/sodium periodate to yield the aldehyde, which is condensed with the Wittig reagent derived from a protected tyrosine precursor, to yield the allylic acetate. The allylic acetate is selectively hydrolyzed with sodium carbonate in methanol, and the allylic alcohol is treated with triphenylphosphine and carbon tetrabromide to yield the allylic bromide. This compound is reduced with zinc in acetic acid to give the transposed trans olefin as a mixture of diastereomers at the newly-formed center. The diastereomers are separated and the pseudodipeptide is obtained by selective transfer hydrogenolysis to unveil the free carboxylic acid.

The pseudodipeptide is then coupled at the C-terminus, according to the above example, with a suitably protected tyrosine residue, and at the N-terminus with a protected alanine residue, by standard techniques, to yield the protected tetrapeptide isostere A-I-Y-Y. The terapeptide is then further condensed with the olefinic tripeptide analog derived by similar means for Lys-Ala-Arg, and so forth to build up the full E2 peptide. The protecting groups are then removed with strong acid to yield the desired peptide analog, which can be further purified by HPLC.

Other pseudodipeptides can be made by the method set forth above merely by substitution of the appropriate starting Boc amino acid and Wittig reagent. Variations in the procedure may be necessary according to the nature of the reagents used, but any such variations will be purely routine and will be obvious to one of skill in the art.

It is further possible couple the pseudodipeptides synthesized by the above method to other pseudodipeptides, to make peptide analogs with several olefinic functionalities in place of amide functionalities. For example, pseudodipeptides corresponding to Met-Arg or Tyr-Lys, etc. could be made and then coupled together by standard techniques to yield an analog of the E2 peptide which has alternating olefinic bonds between residues.

Still another class of peptidomimetic derivatives include the phosphonate derivatives, such as the partially phosphonate derivatived WKHMRLECAIYYKAR peptide:

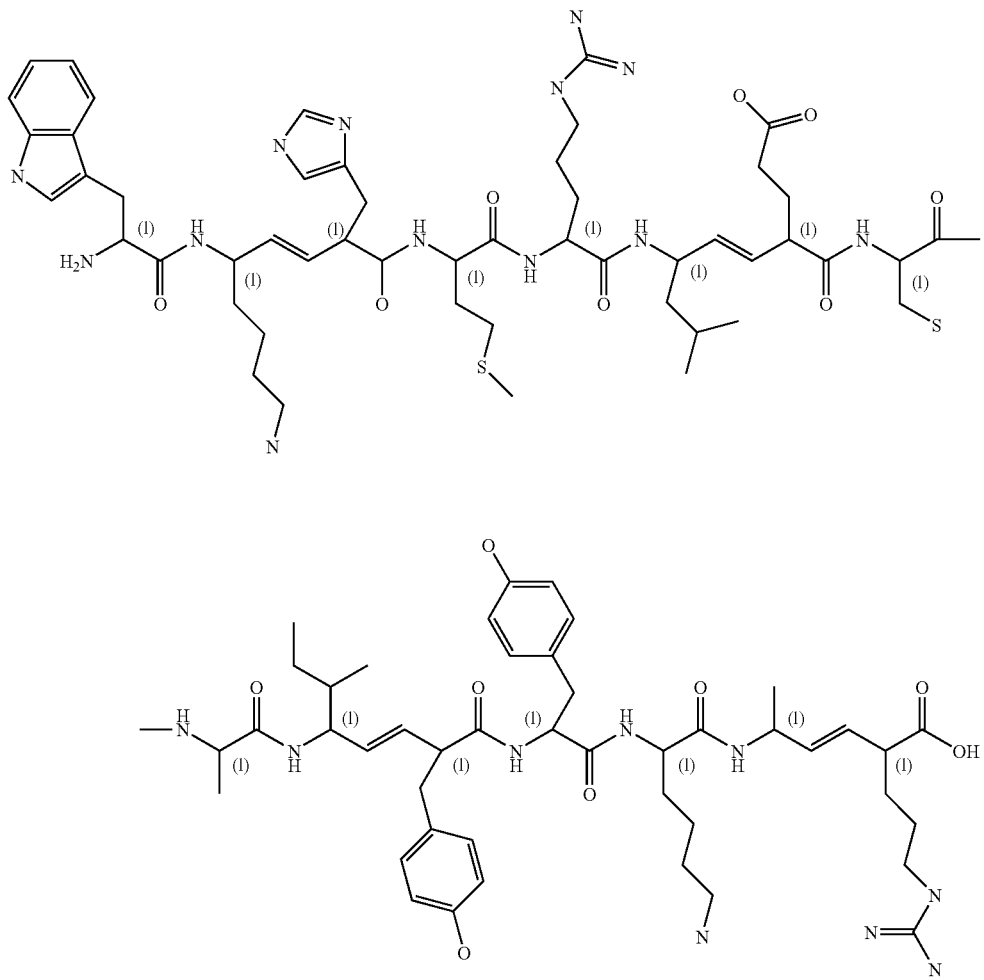

The synthesis of such phosphonate derivatives can be adapted from known synthesis schemes. See, for example, Loots et al. in *Peptides: Chemistry and Biology*, (Escom Science Publishers, Leiden, 1988, p. 118); Petrillo et al. in *Peptides: Structure and Function* (Proceedings of the 9th American Peptide Symposium, Pierce Chemical Co. Rockland, Ill., 1985).

Many other peptidomimetic structures are known in the art and can be readily adapted for use in the the subject E2 peptidomimetics. To illustrate, the E2 peptidomimetic may incorporate the 1-azabicyclo[4.3.0]nonane surrogate (see Kim et al. (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analogue (see Williams et al. (1996) *J. Med. Chem.* 39:1345–1348). In still other embodiments, certain amino acid residues can be replaced with aryl and bi-aryl moieties, e.g., monocyclic or bicyclic aromatic or heteroaromatic nucleus, or a biaromatic, aromatic-heteroaromatic, or biheteroaromatic nucleus.

The subject E2 peptidomimetics can be optimized by, e.g., combinatorial synthesis techniques combined with such high throughput screening as described herein.

Moreover, other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof. A mimetope can be obtained by, for example, screening libraries of natural and synthetic compounds for compounds capable of inhibiting E1–E2 interaction. A mimetope can also be obtained, for example, from libraries of natural and synthetic compounds, in particular, chemical or combinatorial libraries (i.e., libraries of compounds that differ in sequence or size but that have the same building blocks). A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling the predicted mimetope structures can then be produced by, for example, chemical synthesis, recombinant DNA technology, or by isolating a mimetope from a natural source (e.g., plants, animals, bacteria and fungi).

VI. Pharmaceutical Preparations of E2 Peptides and Peptidomimetics

According to another aspect of this invention, E2 peptides and peptidomimetics may be administered directly to PV infected cells. Direct delivery of such E2 therapeutics may be facilitated by formulation of the peptidyl compound in any pharmaceutically acceptable dosage form, e.g., for delivery orally, intratumorally, peritumorally, interlesionally, intravenously, intramuscularly, subcutaneously, periolesionally, or (preferably) topical routes, to exert local therapeutic effects.

Topical administration of the therapeutic is advantageous since it allows localized concentration at the site of administration with minimal systemic adsorption. This simplifies the delivery strategy of the agent to the disease site and reduces the extent of toxicological characterization. Furthermore, the amount of material to be applied is far less than that required for other administration routes. Effective delivery requires the agent to diffuse into the affected cells. Successful intracellular delivery of agents not naturally taken up by cells has been achieved by exploiting the natural process of intracellular membrane fusion, or by direct access of the cell's natural transport mechanisms which include endocytosis and pinocytosis (Duzgunes (1985) *Subcellular Biochemistry* 11:195–286). Such processes are also useful in the direct delivery and uptake of the subject E2 peptides and peptidomimetic by papillomavirus-infected cells.

In one embodiment, the membrane barrier can be overcome by associating the E2 protein in complexes with lipid formulations closely resembling the lipid composition of natural cell membranes. In particular, the subject E2 peptidomimetics are encapsulated in liposomes to form pharmaceutical preparations suitable for administration to living cells and, in particular, suitable for topical administration to human skin. The Yarosh U.S. Pat. No. 5,190,762 demonstrates that proteins can be delivered across the outer skin layer and into living cells, without receptor binding, by liposome encapsulation.

These lipids are able to fuse with the cell membranes on contact, and in the process, the associated E2 peptidomimetic is delivered intracellularly. Lipid complexes can not only facilitate intracellular transfers by fusing with cell membranes but also by overcoming charge repulsions between the cell membrane and the molecule to be inserted. The lipids of the formulations comprise an amphipathic lipid, such as the phospholipids of cell membranes, and form hollow lipid vesicles, or liposomes, in aqueous systems. This property can be used to entrap the E2 peptidomimetic within the liposomes.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Liposomes have been described in the art as in vivo delivery vehicles. The structure of various types of lipid aggregates varies, depending on composition and method of forming the aggregate. Such aggregates include liposomes, unilamellar vesicles, multilameller vesicles, micelles and the like, having particle sizes in the nanometer to micrometer range. Methods of making lipid aggregates are by now well-known in the art. For example, the liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity.

In one embodiment, pH sensitive liposomes are a preferred type of liposome for use with the present invention. One pathway for the entry of liposomes into cellular cytoplasm is by endocytosis into lysozymes of low pH. Accordingly, liposomes which are stable at neutral pH but release their contents at acidic pH can be used to deliver enzymes into the lysozymes of the cytoplasm, whereupon the contents are released.

Liposomes can be made sensitive to the low pH of the lysozymes by the lipid composition. In particular, pH sensitive liposomes can be prepared by using phospholipids which form lipid bilayers when charged but fail to stack in an ordered fashion when neutralized. An example of such a phospholipid is phosphatidylethanolamine, which is negatively charged above pH 9. The net charge of a phospholipid can be maintained at a pH which would otherwise neutralize the head groups by including charged molecules in the lipid bilayer which themselves can become neutralized. Examples of these charged molecules are oleic acid and cholesteryl hemisuccinate, which are negatively charged at neutral pH but become neutralized at pH 5. The effect of combining these together in a lipid bilayer is that at pH 9 all molecules are charged; at pH 7 the net negative charge of the oleic acid and cholesteryl hemisuccinate maintains the stability of the phosphatidylethanolamine, and at pH 5 all components are protonated and the lipid membrane is destabilized. Additional neutral molecules, such as phosphatidylcholine, can be added to the liposomes as long as they do not interfere with stabilization of the pH sensitive phospholipid by the charged molecules.

In another embodiment, the E2 peptidomimetic is formulated with a positively charged synthetic (cationic) lipid N-[1-(2,3-dioleyloxy)propyl]-N,N,N-trimethylammonium chloride (DOTMA), in the form of liposomes, or small vesicles, which can fuse with the negatively charged lipids of the cell membranes of mammalian cells, resulting in uptake of the contents of the liposome (see, for example, Felgner et al. (1987) *PNAS* 84:7413–7417; and U.S. Pat. No. 4,897,355 to Eppstein, D. et al.). Another cationic lipid which can be used to generate E2 peptidomimetic containing liposomes is the DOTMA analogue, 1,2-bis(oleoyloxy)-3-(trimethyl-ammonio)propane (DOTAP) in combination with a phospholipid to form delivery vesicles.

Lipofectin™ (Bethesda Research Laboratories, Gaithersburg, Md.) and/or LipofectAMINE™, commercially available reagents, can be used to deliver the E2 peptidomimetic directly into cells. Positively charged complexes prepared in this way spontaneously attach to negatively charged cell surfaces, fuse with the plasma membrane, and can efficiently deliver functional E2 peptidomimetic into, for example, keratinocytes. Sells et al. (1995) *Biotechniques* 19:72–76 describe a procedure for delivery of purified proteins into a variety of cells using such ploycationic lipid preparations.

A significant body of information is emerging regarding the use of other cationic lipids for the delivery of macromolecules into cells. Other suitable lipid vesicles for direct delivery of the E2 peptidomimetic include vesicles containing a quaternary ammonium surfactant (Ballas et al. (1988) *Biochim. Biophys Acta* 939:8–18); lipophilic derivatives of spermine (Behr et al. (1989) *PNAS* 86:6982–6986).

The lipid formulations of the subject E2 peptidomimetic can be used in pharmaceutical formulations to deliver the E2 peptidomimetic by various routes and to various sites in the animal body to achieve the desired therapeutic effect. Local or systemic delivery of the therapeutic agent can be achieved by administration comprising application or insertion of the formulation into body cavities, inhalation or insufflation of an aerosol, or by parenteral introduction, comprising intramuscular, intravenous, intradermal, peritoneal, subcutaneous and topical administration.

Topical formulations are those advantageously applied to the skin or mucosa. Target mucosa can be that of the vaginal, cervical, vulvar, penal or anorectal mucosa, or target mucosa can be that of the gastrointestinal tract, comprising the mouth, larynx, esophagous and stomach. Other target tissues can be the accessible epidermal tissues which are infected by HPV. Lipids present in topical formulations can act to facilitate introduction of therapeutic E2 peptidomimetic into the target tissue, such as the stratum or corneum of the skin, by perturbing the barrier properties of the protective membrane, or by introducing perturbing agents or penetration enhancers such as DMSO, Azone™ or by promoting the activity of these penetration enhancers.

Other pharmaceutical formulations comprising the cationic lipids of the invention are topical preparations containing an anesthetic or cytostatic agent, immunomodulators, bioactive peptides or oligonucleotides, sunscreens or cosmetics. Preparations for topical use are conveniently prepared with hydrophilic and hydrophobic bases in the form of creams, lotions, ointments or gels; alternatively, the preparation may be in the form of a liquid that is sprayed on the skin. The effect of the cationic lipids is to facilitate the penetration of the active antiviral agent through the stratum corneum of the dermis.

The composition and form of pharmaceutical preparations comprising the liposome, in combination with the E2 peptidomimetic, can vary according to the intended route of administration.

Also, by suitable modifications of the liposome membranes, the liposomes can be made to bind to specific sub-populations of cells.

In still another embodiment, the therapeutic E2 peptidomimetic can be delivered by way of an artificial viral envelope (AVE). The art as described a number of viral envelopes which which exploit molecular recognition of cell surface receptors by viral surface proteins as a means for selective intracellular delivery of macromolecules, including proteins. According to the method of Schreier, et. al., U.S. Pat. No. 5,252,348, a virtually unlimited number of artificial viral envelopes can be prepared and applied using recombinant or isolated surface determinants. For example, the AVEs be generated as viral mimetics of a number of human viruses including arboviruses; flaviviridae; bunyaviridae; hepatitis viruses; Epstein-Barr viruses; herpes viruses; paramyxoviruses; respiratory syncytical virus; retroviruses including human T-lymphotrophic virus type I and II (HTLV-I/II) and human immunodeficiency virus type 1 and 2 (HIV-1/2); rhinoviruses; orthopoxviruses; and human papilloma viruses (particularly those engineered not to express E6 and/or E7).

In another embodiment, direct delivery of a therapeutic E2 peptidomimetic may be facilitated by chemical modification of the polypeptide itself. One such modification involves increasing the lipophilicity of the E2 peptidomimetic in order to increase binding to the cell surface, in turn, stimulating non-specific endocytosis of the protein. Lipophilicity may be increased by adding a lipophilic moiety (e.g., one or more fatty acid molecules) to the E2 peptidomimetic. A wide variety of fatty acids may be employed. For example, the protein may be palmitoylated. Alternatively, a lipopeptide may be produced by fusion or cross-linking, to permit the E2 peptidomimetic to resemble the natural lipopeptide from *E. coli*, tripalmitoyl-S-glycerylcysteilseryl-serine, at its amino terminus. This lipopeptide has been shown to increase the uptake of fused peptides (P. Hoffmann et al., (1988) *Immunobiol.* 177:158–70). Lipophilicity may also be increased by esterification of the protein at tyrosine residues or other amino acid residues. And uptake of the E2 peptidomimetic may be increased by addition of a basic polymer such as polyarginine or polylysine (Shen et al. (1978) *PNAS* 75:1872–76).

Direct delivery of E2 peptidomimetics according to this invention may also be effected by the use of transport moieties, such as protein carriers known to cross cell membranes. For example, an E2 peptide may be fused to a carrier protein, preferably by a genetic fusion which may be expressed in a system such as *E. coli*, barulovirus or yeast.

According to one embodiment of this invention, the amino terminus of the E2 peptide may be fused to the carboxy terminus of a transport moiety using standard techniques.

Nucleotide sequences encoding such carrier-E2 peptide fusion proteins, operatively linked to regulatory sequences, may be constructed and introduced into appropriate expression systems using conventional recombinant DNA procedures. The resulting fusion protein may then be purified and tested for its capacity to (1) enter intact eukaryotic cells and (2) inhibit viral DNA replication once inside the intact eukaryotic cells.

In choosing a useful carrier protein, those of skill in the art will recognize the desirability of appropriate control experiments designed, inter alia, to test the possibility that the carrier portion of the fusion protein itself interacts with elements of the E1/E2 DNA replication transcriptional regulation system. If the carrier portion of the fusion protein is found to have undesirable interactions, such as enhancement of papillomavirus DNA replication, the portions of the carrier sequence responsible for these interactions should be identified and deleted in a way which permits the sequence to retain its carrier capacity. Alternately, one of several conventional carrier sequences which do not interact with elements of the E1/E2 DNA replications system can be substituted.

Useful carrier proteins include, for example, bacterial hemolysins or "blending agents", such as alamethicin or sulfhydryl activated lysins. Other carrier moieties which may be used include cell entry components of bacterial toxins, such as *Pseudomonas* exotoxin, tetanus toxin, ricin toxin, and diphtheria toxin. Also useful is melittin, from bee venom. Other useful carrier proteins include proteins which are viral receptors, cell receptors or cell ligands for specific receptors that are internalized, i.e., those which cross mammalian cell membranes via specific interaction with cell surface receptors, recognized and taken into the cell by cell surface receptors. Such cell ligands include, for example, epidermal growth factor, fibroblast growth factor, transferrin and platelet-derived growth factor. Alternatively, the ligand may be a non-peptide, such as mannose-6-phosphate, which permits internalization by the mannose-6-phosphate receptor. The transport moiety may also be selected from bacterial immunogens, parasitic immunogens, viral immunogens, immunoglobulins or fragments thereof that bind to target molecules, cytokines, growth factors, colony stimulating factors and hormones. A transport moiety may also be derived from the tat protein of HIV-1.

As an alternative or addition to the above-described chemical modifications and protein carriers, which may be employed alone or in combination, other agents which allow penetration of the keratinized cell layer may be employed to facilitate delivery of the E2 peptidomimetics of this invention to papillomavirus-infected cells. In topical applications, for example, the E2 peptidomimetic may be administered in combination with dimethylsulfoxide, an agent which promotes penetration of cell membranes by substances mixed with it. Useful keratinolytic agents include, for example, salicylic acid, urea, and alpha-hydroxyacids. For such applications, the E2 peptidomimetic and any other agent may be administered topically, in cream or gel form.

According to an alternate embodiment of this invention, the therapeutic E2 peptidomimetic may be administered serially or in combination with other therapeutics used in the treatment of papillomavirus infections or diseases caused by them. Such therapeutics include interferons, such as IFN-γ, IFN-α and IFN-β derived from natural sources or produced by recombinant techniques, other cell mediators formed by leukocytes or produced by recombinant techniques such as for example, interleukin-1, interleukin-2, tumor necrosis factor, macrophage colony stimulating factor, macrophage migration inhibitory factor, macrophage activation factor, lymphotoxin and fibroblast growth factor. Alternatively, the E2 peptidomimetic may be administered serially or in combination with conventional therapeutic agents or regimens such as, for example, salicylic acid, podophyllotoxin, retinoic acid, surgery, laser therapy and cryotherapy. Such combination therapies may advantageously utilize less than conventional dosages of those agents, or involve less radical regimens, thus avoiding any potential toxicity or risks associated with those therapies.

It will also be understood by those skilled in the art that any of the above enumerated delivery methods may be augmented, where topical application is being carried out, by the use of ultrasound or iontophoretic delivery devises which facilitate transdermal delivery of proteins. See, for example, Banga et al. (1993) *Pharm Res* 10:697–702; and Mitragotri et al. (1995) Science 269:850–853.

VII. Gene Therapy

In another aspect, the present invention relates to gene therapy constructs containing a nucleic acid encoding a papillomavirus E2 peptide of the present invention, operably linked to at least one transcriptional regulatory sequence. The gene constructs of the present invention are formulated to be used as a part of a gene therapy protocol to deliver the subject therapeutic protein to a papillomavirus-infected or -transformed cell in an animal.

Any of the methods known to the art for the insertion of DNA fragments into a vector may be used to construct expression vectors consisting of appropriate transcriptional/translational control signals and the desired E2 peptide-encoding nucleotide sequence. See, for example, Maniatis T., Fritsch E. F., and Sambrook J. (1989): *Molecular Cloning* (A Laboratory Manual), Cold Spring Harbor Laboratory, Cold Spring Harbor, N.Y.; and Ausubel F. M., Brent R., Kingston R. E., Moore, D. D., Seidman J. G., Smith J. A., and Struhl K. (1992): *Current Protocols in Molecular Biology*, John Wiley & Sons, New York. These methods may include in vitro DNA recombinant and synthetic techniques and in vivo genetic recombination. Expression of a nucleic acid sequence encoding an E2 peptide may be regulated by a second nucleic acid sequence so that the peptide is expressed in a host infected or transfected with the recombinant DNA molecule. For example, expression of an E2 peptide may be controlled by any promoter/enhancer element known in the art. The promoter activation may be tissue specific or inducible by a metabolic product or administered substance.

Promoters/enhancers which may be used to control the expression of the E2 peptide in vivo include, but are not limited to, the native E2 promoter, the cytomegalovirus (CMV) promoter/enhancer (Karasuyama et al., 1989, *J. Exp. Med.*, 169:13), the human β-actin promoter (Gunning et al. (1987) *PNAS* 84:4831–4835), the glucocorticoid-inducible promoter present in the mouse mammary tumor virus long terminal repeat (MMTV LTR) (Klessig et al. (1984) *Mol. Cell Biol.* 4:1354–1362), the long terminal repeat sequences of Moloney murine leukemia virus (MuLV LTR) (Weiss et al. (1985) RNA Tumor Viruses, Cold Spring Harbor Laboratory, Cold Spring Harbor, N.Y.), the SV40 early or late region promoter (Bemoist et al. (1981) *Nature* 290:304–310; Templeton et al. (1984) *Mol. Cell Biol.*, 4:817; and Sprague et al. (1983) *J. Virol.*, 45:773), the promoter contained in the 3' long terminal repeat of Rous sarcoma virus (RSV) (Yamamoto et al., 1980, *Cell,* 22:787–797), the herpes simplex virus (HSV) thymidine kinase promoter/enhancer (Wagner et al. (1981) *PNAS* 82:3567–71), and the herpes simplex virus LAT promoter (Wolfe et al. (1992) *Nature Genetics,* 1:379–384), and Keratin gene promoters, such as Keratin 14.

Expression constructs of the subject E2 peptides may be administered in any biologically effective carrier, e.g. any formulation or composition capable of effectively delivering the recombinant gene to cells in vivo. Approaches include insertion of the E2 peptide coding sequence in viral vectors including recombinant retroviruses, adenovirus, adeno-associated virus, and herpes simplex virus-1, or recombinant eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid into a cell is by use of a viral vector containing nucleic acid encoding the particular E2 peptide desired. Infection of cells with a viral vector has the advantage that a large proportion of the targeted cells can receive the nucleic acid. Additionally, molecules encoded within the viral vector, e.g., the recombinant E2 peptide, are expressed efficiently in cells which have taken up viral vector nucleic acid.

In addition to viral transfer methods, such as those illustrated above, non-viral methods can also be employed to cause expression of a E2 peptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the E2 peptide-encoding gene by the targeted cell. Exemplary gene delivery systems of this type include liposomal derived systems, poly-lysine conjugates, and artificial viral envelopes.

In clinical settings, the gene delivery systems for the therapeutic E2 peptide coding sequence can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or "gene gun" techniques. In preferred embodiments, the gene therapy construct of the present invention is applied topically to HPV infected or transformed cells of the skin or mucusal tissue. An E2 peptide gene construct can, in one embodiment, be delivered in a gene therapy construct by electroporation using techniques described, for example, by Dev et al. ((1994) *Cancer Treat Rev* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

EXEMPLIFICATION

The invention now being generally described, it will be more readily understood by reference to the following examples which are included merely for purposes of illustration of certain aspects and embodiments of the present invention, and are not intended to limit the invention.

In the results presented here, we have achieved replication of HPV 16 DNA in vitro. This replication mimics that seen in transient in vivo replication assays, in that it requires interaction of E2 with E1 (31, 32). Furthermore, we demonstrate the ability of 23 or 15 amino acid peptides derived from the HPV16 E2 amino terminus to disrupt both interaction between E1 and E2, and papillomavinis DNA replication in vitro. The activity of such a peptide as a functional inhibitor in these assays has several implications: (i) it identifies a discrete region of E2 that is necessary and sufficient for specific interaction with E1; (ii) it provides proof-of-concept that a relatively small molecule may be used to inhibit E1–E2 interaction and papillomavirus DNA replication; (iii) provides a starting point for the design or discovery of biologically active molecules capable of inhibiting papillomavirus DNA replication, of both low and high risk subtypes; (iv) provides a reagent that may facilitate functional disection of the dynamic processes that result in the stepwise assembly of the papillomavirus DNA replication initiation complex. Furthermore, we have utilized an alanine scanning approach to determine specific residues within the 15-amino acid peptide that are important to inhibition of E1–E2 interaction. For HPV-16E2 protein it was determined that residues R37, L38, E39 and I42 are important for the inhibitory activity of the peptide. In addition, a fusion peptide in which the wild-type inhibitory peptide was fused to a membrane-translocating region of the *Drosophila* Antennapedia protein retained inhibitory activity comparable to the wild-type peptide. These observations may aid in the identification of effective bioactive anti-viral compounds that would inhibit HPV DNA replication.

Materials and Methods

Baculovirus expression of HPV E1 and E2 proteins. An NcoI-SmaI fragment from pUC-E116 (9) containing the HPV-16 E1 protein coding region was made blunt by using T4 polymerase and inserted into the blunt-ended BamHI site of pBS-EE to generate pBS-EE-E116. [PBS-EE was generated by cloning the XbaI-Bam HI fragment encoding the polyomavirus middle T antigen EE epitope (18) from pUC-EE into pBluescript-SK (+) (Stratagene).] The Eco RI-NotI fragment from pBS-EE-E116 was recloned into the pVL1392 baculovirus transfer vector (Pharningen). HPV-16 E2 and HPV-16 E2 E39A were cloned as Bam HI-Eco RI fragments into pVL 1392.

Recombinant baculovirus expressing HPV-11 EE-E1 and HPV-11 E2 were generously provided by Louise Chow. Hi-Five cells were infected at a multiplicity of 5 to 10 PFU per cell and incubated at 27° C. for 48 h. Cells were scraped into ice-cold phosphate-buffered saline, pelleted by centrifugation in a Sorvall RT6000D tabletop centrifuge at 1,000 rpm for 5 min, washed once in ice-cold phosphate-buffered saline, and repelleted. The cell pellet was then resuspended in hypotonic buffer (buffer A) containing 10 mM HEPES-K+ (pH 7.5), 10 mM KCl, 1.5 mM MgCl2, 0.5 mM dithiothreitol (DTT) and protease inhibitor cocktail (PIC; 1 mM phenylmethylsulfonyl fluoride, 10 µg/ml aprotinin, 10-µg/ml leupeptin, 10-µg/ml pepstatin A, 10-µg/ml phenanthroline, 16-µg/ml benzamidine). Cells were pelleted as before, resuspended in buffer A containing 0.5% Nonidet P-40 (NP-40), and incubated on ice for 10 nin. Lysates were then spun at 4° C. in a Sorvall tabletop microcentrifuge (3,000 rpm). The cytoplasmic extract supernatant was removed, and an equal volume of 50% (vol/vol) glycerol was added. Lysates were quick-frozen on dry ice and stored at −70° C. until use. The nuclear pellet was washed once in buffer A without NP-40, resuspended in buffer C (20 mM HEPES-K+ [pH 7.9], 429 mM NaCl, 1.5 mM MgCl2, 0.2 mM EDTA, 25% [vol/vol] glycerol, 0.5 mM DTT containing PIC), and incubated on ice for 30 to 40 min with intermittant vortexing. After clarification by centrifugation at full speed in a Sorvall microcentrifuge for 10 min at 4° C., the nuclear extract was quick frozen on dry ice and stored at −70° C. until use.

In vitro HPV E1–E2 binding assay. 300–500 ng protein from HPV16 or HPV11 EE-E1 expressing recombinant baculovirus infected cell nuclear extracts and 80–120 ng from HPV E2 baculovirus infected cell nuclear extracts were incubated in 50011 NET-gel buffer (50 mM Tris-HClpH7.5, 150 mM NaCl, 0.1% NP-40, 1 mM EDTA, 0.25% gelatin) at 4° C. for one hour. 1–2 µg anti-EE monoclonal antibody was added and incubated with shaking at 4° C. for one hour. Immune complexes were precipitated with protein-G agarose beads and washed twice for 30 minutes with ice cold NET-gel buffer. Precipitated proteins were detected by Western blot using appropriate primary antibodies and anti-rabbit IgG HRP or anti-mouse IgG HRP (Amersham). Membranes were blocked for one hour in TNET (10 mM Tris 7.5, 2.5 mM EDTA, 50 mM NaCl, 0.1% Tween-20) containing 4%(w/v) dry milk. Washes and antibody reactions were carried out in TNET, and proteins were visualized by chemiluminescence (Reneaissance ECL, NEN) and autoradiography. Bands were quantitated using the NIH image program.

Purification of HPV EE-E1 and E2 proteins. EE-E1 containing baculovirus infected cell nuclear extract (3–5 mg total protein) containing 1% NP-40 was passed over a mono-Q column (Econo-Pac Q cartridge, Bio-Rad, No.732–0025). The flowthrough was incubated at 4° C. for one hour with 200 µl anti-EE monoclonal antibody that had been covalently crosslinked to protein G sepharose beads. Beads were pelleted by centrifugation and washed once with 800 µl (1%) NP-40 lysis buffer with proteinase inhibitor cocktail (PIC). Beads were then washed three times for ten minutes at 4° C. with 800 µl high salt buffer (20 mM Tris pH7.0, 0.5M NaCl, 0.5 mM DTT, 0.1% NP-40, and PIC), followed by three ten minute washes with 800 µl sodium phosphate buffer (10 mM $NaPO_4$ pH 8.0, 0.5 mM DTT, 0.1% NP-40, PIC). EE-E1 was eluted from the pelleted beads in 100 mM triethylamine (pH 11.5). The beads were pelleted by centrifugation at 4° C., and the supernatant was dialyzed for 3 hours at 4° C. against one liter of dialysis buffer [HEPES-K+ (pH 7.5), 1 mM DTT, 10% glycerol, 150 mM NaCl]. Dialysis buffer was then changed and dialysis was continued overnight at 4° C. This procedure yielded approximately 100–150 µg/µl EE-E1 (>95% pure). 20 µl aliquots of purified EE-E1 were quick-frozen on dry ice and stored at −70° C. until use.

Baculovirus infected cell nuclear extract containing E2 in Buffer C (3 mg/ml) was applied to an Econo-Pac Heparin column cartridge (Bio-Rad No. 732-0075) at 4° C. After washing with five column volumes of Buffer C containing proteinase inhibitor cocktail at a flow rate of 1 ml/min. E2 was eluted in five column volumes of Buffer C containing 0.7M NaCl and 0.5 ml column fractions were collected. Fractions containing E2 were determined by Comassie staining of SDS-PAGE gels loaded with aliquots of eluted fractions. This procedure yielded 300–500 µg/µl E2, which was stored at −70° C. until use.

In vitro replication reactions. In vitro replication reactions were essentially as described by Kuo et al. (18) in 25 µl reactions at 37° C. for indicated times. Standard reactions were for 2 hours, and were terminated by addition of 200 µl stop solution (20 mM Tris-HCl pH 7.5, 10 mM EDTA, 0.1% SDS, and 20 µg/ml RNase A). After incubation at 37° C. for 15 minutes, proteinase K was added (200 µg/ml) and incubation was continued 30 minutes. Samples were extracted with 250 µl phenol/chloroform/isoamyl alcohol (25:24:1), ethanol precipitated, washed with 70% ethanol, dried, resuspended in 20–30 µl TE, and analyzed on a 0.8% agarose gel (TAE). The agarose gel was dried onto Hybond N+ membrane (Amersham), and replicated DNA was visualized by autoradiography. Bands were quantitated by Phosphorimager analysis. Replication templates were pKS7838–7905 (nt7838–7905/1–130) containing the HPV16 replication origin, and pUC7874-99 containing the HPV11 origin of replication (nt7874–7933/1–99). pUC7874-99 was a generously provided by Dr. Louise Chow.

Use of EE-EIC. The carboxy terminus of HPV16-E1, from amino acid 424 to 649, is the minimal domain necessary for interaction with E2 (Yasugi et al. 1997). An epitope tagged form of this domain (EE-EIC) was used in the E1–E2 interaction assays presented here. EE-EIC was shown to act the same as the full-length E1 protein with regard to inhibition by peptides (Kasukawa et al. 1998; unpublished data).

Fusion moieties (WP15 and membrane-translocating peptide). Fusion moieties were designed to contain the WP15 fused to either the membrane-translocating HIVderived Tat protein (aa 48–60) or the membrane-translocating *Drosophila* Antennapedia protein (aa 42–58). Synthesis of Tat-WP and -WP was carried out by Genosys Company (Texas). Both membrane-translocating carrier peptides were positioned at the aminoterminus and contained a Gly-Gly spacer between the transporter moiety and the WP 15 amino acid sequence.

In vitro HPV E1–E2 competition binding assay. HPV-16 EE-EIC (240 ng) in 500 1 NET gel buffer (50 mM Tris-HCl [pH 7.5], 150 mM NaCl, 0.1% NP-40, 1 mM EDTA, 0.25% gelatin) were pre-incubated with 0 µM, 10 µM, 20 µM, or 40 µM peptide for 10 minutes on ice. The final concentration of DMSO, the peptide solvent, was kept constant in all samples. Nuclear extract containing HPV-16 E2 was then added, and the mixture was incubated with shaking at 4° C. for 1 hour. Anti-EE monoclonal antibody (1 mg/ml) (BAbCo) was added, and the mixture was incubated with shaking for 30 minutes. Immune complexes were precipitated with protein G-agarose beads for an additional 30 minutes at 4° C. The beads were washed with 500 1 ice-cold NET-gel buffer three times.

In Vitro Replication of HPV16 DNA.

Figure 1:
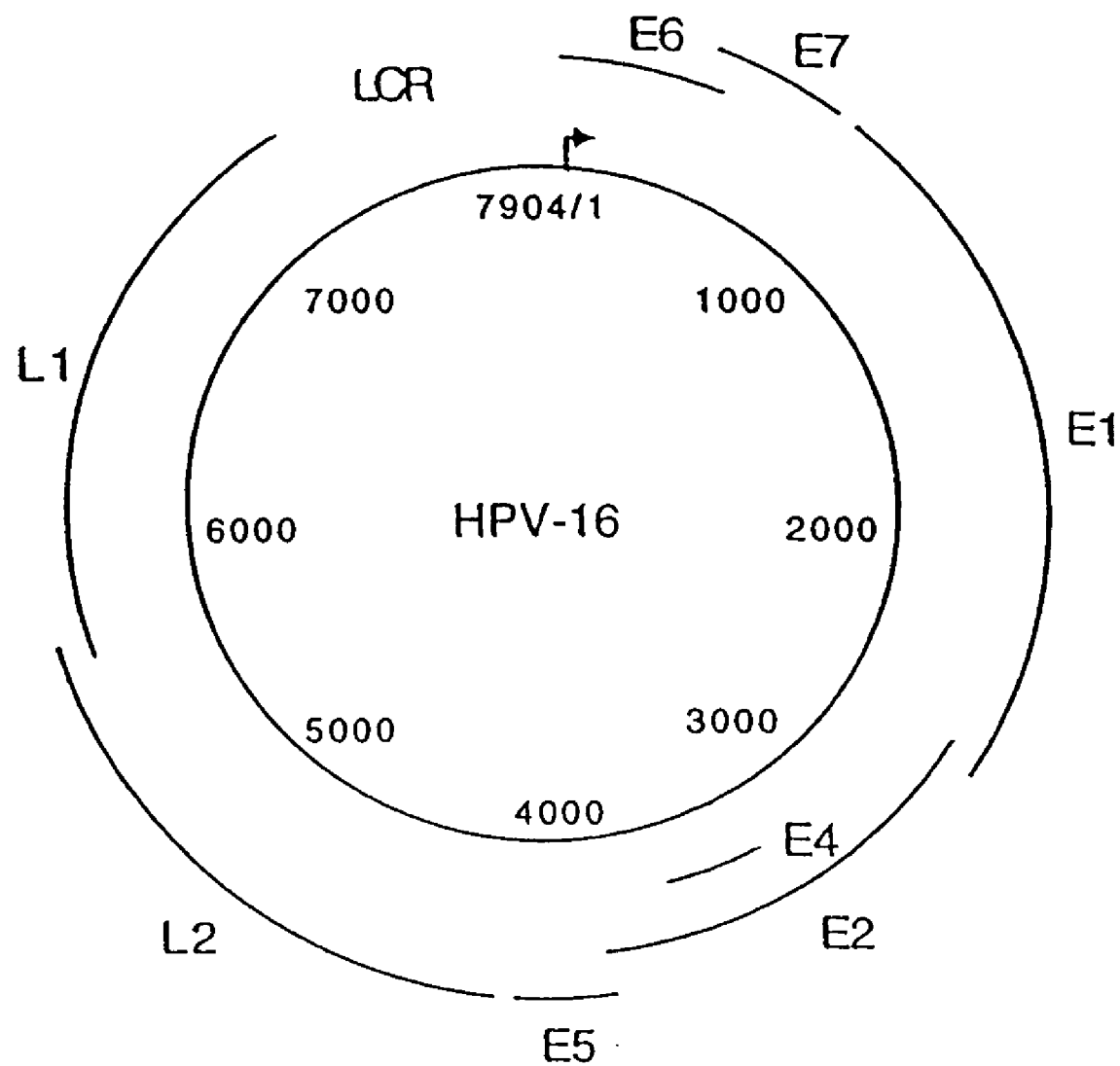
FIG. 1. Genomic Map of HPV-16. The genome is a double-stranded circular DNA molecule containing 7,904 base pairs. Transcription occurs in a clock-wise manner. Only one promoter has been identified thus far. Open reading frames deduced from the DNA sequences are designated E1–E7 and L1–L2. The viral long control region (LCR) contains transcriptional and replication regulatory elements. Diagram courtesy of Peter Howley (Fields Virology, Third Edition 1996).
Figure 2:
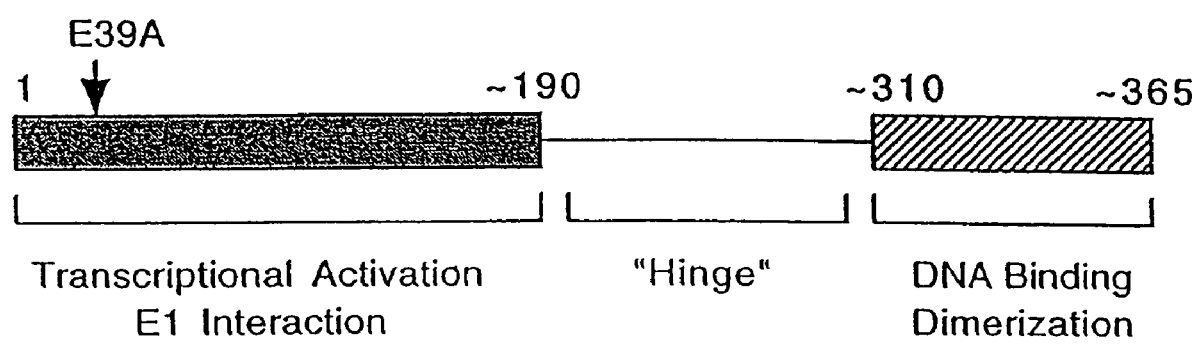
FIG. 2. Functional domains of the papillomavirus E2 protein. The E2 regulatory protein is composed of two well-conserved domains. Transcriptional activation and E1 interaction functions have been localized to a domain spanning aa1–190. This domain encompasses the E39 residues which is critical for viral DNA replication. The E2 DNA binding and dimerization domain spans approximately the carboxy-terminal 100 amino acids. The amino-terminal and carboxy-terminal domains are connected by a hinge region.
Figure 3:
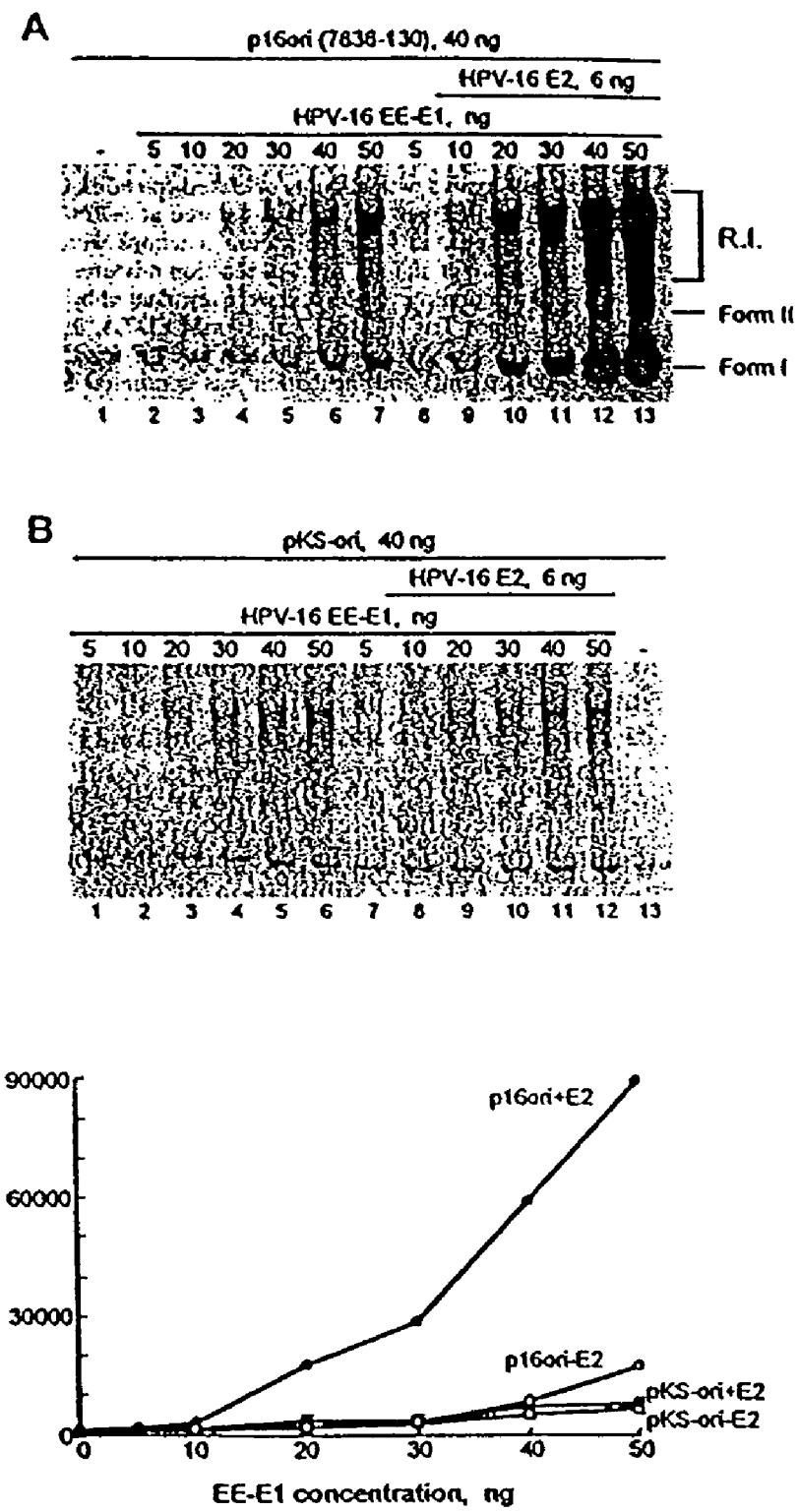
FIG. 3, Panels A, B and C. E2 stimulates replication of HPV16 in vitro. A. Replication of the HPV16 origin containing plasmid p16ori, a Bluescript KS+ plasmid containing HPV16 genomic sequences (7838–139), using 293 cell extract and increasing amounts of EE-16E1 (10–50 ng) in the presence (lanes 8–13) or absence (lanes 2–7) of HPV16 E2. The reaction in lane 1 contained no HPV16 E1 or E2. Replicative intermediates (RI), Form I and Form II DNA analogous to those observed by Kuo et al. (18) are indicated. B. In vitro HPV16 DNA replication is origin dependent. Minimal replication of the Bluescript KS+ plasmid that does not contain HPV16 origin sequences is observed under conditions identical to those described in A. C. Phosphorimager quantitation of the replication experiments shown in FIGS. 1A and B.

Transient replication assays have demonstrated that interaction between HPV 16 E1 and E2 is required for efficient origin dependent papillomavirus replication in vivo (31). E2 stimulation of BPV and HPV11 replication has been previously demonstrated in vivo (9, 19, 38, 40) and in vitro (18, 19, 43). We sought to establish a system for the study of HPV16 DNA replication in vitro, and to determine whether specific interaction between HPV16 E1 and E2 was required for HPV16 DNA replication in this system. FIG. 3A shows replication of an HPV16 ori containing plasmid in vitro using 293 cell extracts, along with partially purified HPV16 E2 and increasing amounts of affinity purified HPV16 EE-E1. As has been documented for other papillomavirus E1 proteins, some replication was observed using relatively large amounts of E1 in the absence of E2 (lanes 2 through 7) (6, 16, 22, 33, 40, 48). Addition of 6ng of E2 greatly stimulated in vitro replication (lanes 8–13), whereas no replication was observed in the absence of EE-E1 (lane 1). Replication in this assay is ori-dependent, since the small amount of replication of the pKS plasmid lacking the HPV16 origin detected at high concentrations of EE-E1 (FIG. 3B, lanes 1–6) was not stimulated by E2 (FIG. 1B, lanes 7–12). Quantitation of these results is shown in FIG. 3C.

E1 Interaction is Required for E2 Stimulation of HPV16 Replication In Vitro.

Figure 4:
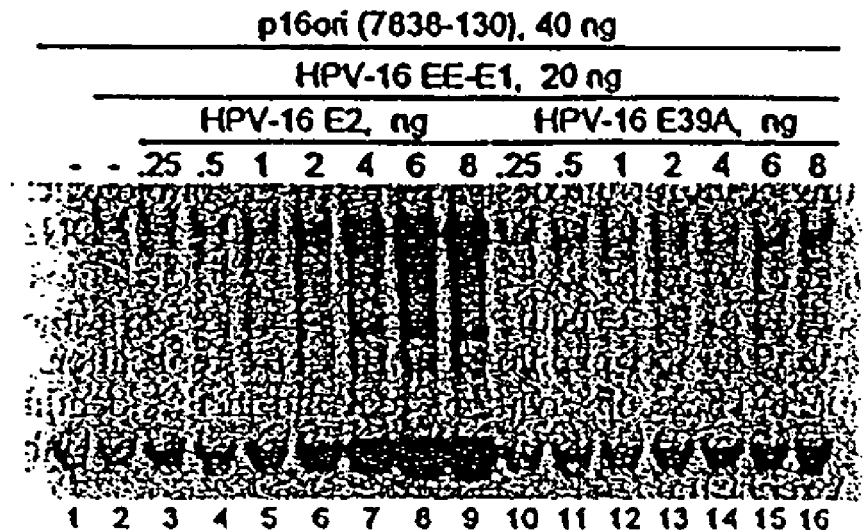
FIG. 4, Panels A and B. Interaction of the E2 amino terminus with E1 is required for HPV16 DNA replication in vitro. A. Replication of p16ori (40 ng) was determined in the presence of 293 cell extract, 20 ng EE-E1, and increasing amounts of wild type (lanes 2–9) or E1 interaction defective E39A HPV16 E2 (lanes 10–16). B. Phosphorimager quantitation of the replication experiments shown in FIG. 4A.
Figure 4:
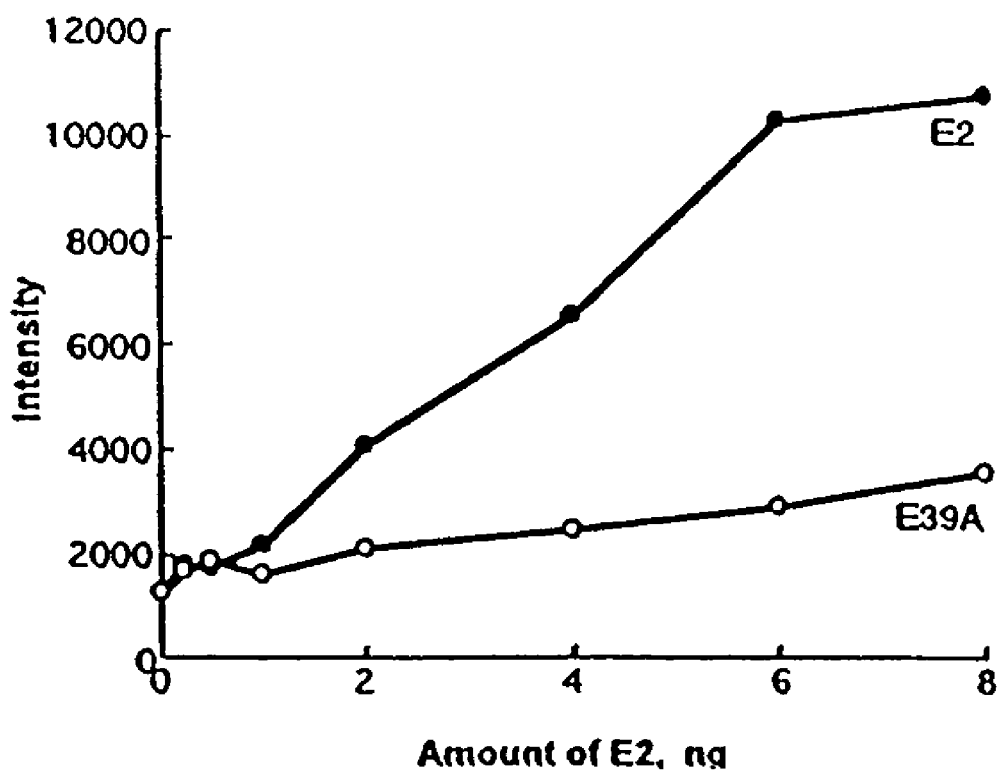

We have previously demonstrated that substitution of alanine for the conserved glutamic acid residue at amino acid residue 39 of HPV16 E2 (E39A) disrupts both HPV16 E1 interaction and transient HPV16 DNA replication in transient co-transfection assays. E39A is, however, fully competent as a transcriptional activator (31). To test the capacity of this mutant E2 protein to support HPV16 DNA replication in vitro, increasing amounts of wild type HPV16 E2 or the E39A HPV16 E2 mutant protein were tested for in vitro replication activity in the presence of 20ng EE-E1 (FIG. 4A). Wild type E2 greatly stimulated in vitro replication in a dose responsive manner, whereas the E39A mutant of HPV16 E2, which does not interact with E1, had only a slight stimulatory effect, even at relatively high concentrations. This result demonstrated the dependence of E2 amino terminal mediated interaction with E1 in in vitro replication. Quantitation of these results is shown in FIG. 4B.

Inhibition of Interaction Between HPV16 E1 and E2 In vitro.

The results described above suggested that a region of HPV16 E2 including the E39 residue might encompass a domain sufficient for interaction with E1. Therefore, we reasoned that a peptide encompassing this domain of HPV16 E2 might inhibit interaction between HPV16 E1 and E2, thereby inhibiting HPV16 DNA replication (FIG. 5). In order to test this possibility, HPV16 E2 and epitope tagged full length HPV6 E1 (EE16-E1) proteins were expressed separately using baculovirus vectors. EE-E1 and associated E2 proteins were immunoprecipitated using an anti-EE epitope monoclonal antibody. Precipitated E2 was detected by Western blot using polyclonal antiserum raised to the DNA binding domain of HPV16 E2 (35). As shown in lane 2 of FIG. 6A, E2 co-immunoprecipitated with EE16-E1, but was not precipitated by the EE epitope antibody in the absence of EE16-E1 (lane 1). Peptides encompassing HPV16 E2 amino acids 29–51 (E2N-WP23) or residues 33–47 (E2N-WP15) of HPV16 E2 were then tested for inhibition of E1-E2 interaction. These peptide sequences were derived from the sequence of HPV16 E2, and were based on an alignment of amino terminal residues that are conserved among the papillomavirus E2 proteins (FIG. 5). Lanes 3–9 of FIG. 6A (upper panel) show the inhibitory effects of increasing concentrations of the E2N-WP23 peptide. The smaller E2N-WP15 peptide displayed comparable inhibition of E1–E2 interaction (FIG. 6A; lower panel, lanes 3–9). Both the HPV16 E2 protein itself and the E2 derived peptides act specifically in these assays, since the E39A replication defective HPV16 E2 mutant bound only slightly to EE16-E1 (lanes 14). Furthermore, 23-mer and 15-mer peptides containing an amino acid substitution analogous to that of the HPV16 E2 E39A mutant did not inhibit E1–E2 interaction at concentrations at which the wild type peptide could do so (lanes 10–13). These peptides are named E2N-MP23 and E2N-MP15, respectively (see FIG. 5). Quantitation of these results is shown in FIG. 6B. The $IC_{50}$ for inhibition of E1–E2 interaction by the E2N-WP23 and E2N-WP15 in these assays was 5 mM and 7.5 mM, respectively. In addition, when inhibition of E1–E2 interaction by peptide was plotted as a function of substrate concentration, this analysis indicated that the E2N-WP23 and E2N-WP15 peptides act through competitive inhibition (data not shown). We have previously shown that a domain spanning amino acids 421–647 of the HPV16 E1 carboxy terminus is necessary and sufficient for E2 interaction (45). Comparable and specific peptide inhibition of E2 interaction was observed using an epitope tagged form of this HPV16 E1 aa421–647 carboxyl terminal domain (data not shown).

Since the E2N-WP23 and E2N-WP15 peptides could inhibit interaction between HPV6 E1 and E2, their ability to inhibit in vitro HPV16 DNA replication was also tested (FIGS. 7A and 7B). FIG. 7C shows the compiled quantitative results of several independent experiments. Both the 23-mer and 15-mer forms of the wild type peptide could effectively inhibit in vitro replication. The inhibitory effects of E2N-MP23 and E2N-MP15 were also tested as specificity controls. Each of the wild type peptides inhibited replication much more effectively than the respective E39A substituted analog, a result consistent with the importance of the E39 residue of HPV16 E2 in the interaction with E1. The replication inhibitory effects of the peptides are a result of inhibition of E1-E2 interaction, since the peptides had no effect on the low levels of replication observed with E1 alone (data not shown). Smaller peptides derived from sequences within the E2N-WP15 did not inhibit HPV16 E1–E2 interaction or replication in vitro (data not shown).

Peptide Inhibition of In Vitro E1–E2 Interaction and Replication is Not Limited to HPV16.

Very little is known about the physical properties of domains within the papillomavirus E1 and E2 proteins that are involved in intermolecular recognition and association. Within the sequence of the HPV16 E2 derived 15 amino acid minimal peptide that inhibits HPV16 E1–E2 interaction, there are seven well conserved residues (W-X-X-M/V/I-R-X-E-X-X-I/L-X-X-X-X-A-R) (see also FIG. 5). We reasoned that if these residues adequately represented a conserved E1 interaction domain, the HPV16 E2 derived peptide might also inhibit interaction between other HPV E1 and E2 proteins. We therefore tested the inhibitory effects of the E2N-WP15 peptide using the HPV11 E1 and E2 proteins. Epitope tagged versions of the HPV11 (HPV11 EE-E1) and HPV16 E1 (HPV16 EE-E1) proteins were tested for binding to HPV11 and HPV16 E2. The effect of the E2N-WP15 peptide on these interactions was also assessed. As shown in FIG. 7A, E2N-WP15 effectively inhibited interaction between HPV11 E1 and HPV16 E2 (lanes 10–13), along with HPV11 E1/E2 interaction (lanes 20–24). As was the case for interaction between HPV16 E2 and HPV16 E1, the HPV16 E2 E39A mutant did not bind HPV11 E1 (lanes 8 and 16). The E2N-MP15 peptide did not inhibit HPV 11/11 E1-E2 interaction or interaction between HPV11 E1 and HPV16 E2. This suggests that the domain of HPV16 E2 that interacts with HPV16 E1, its natural counterpart, can also interact specifically with HPV11 E1. Interaction between HPV11 E1 and HPV16 E2 was not observed (data not shown). This is consistent with the inability of HPV16 E1 and HPV11 E2 to support transient replication in co-transfection assays (47). Thus, although many elements of E1–E2 interaction are conserved among the HPV subtypes, these interactions are not completely interchangeable. Further examination of the nature of this non-reciprocal functionality may reveal important determinants in the specificity of E1-E2 interaction.

The ability of the E2N-WP15 peptide to inhibit HPV11 E1 mediated replication in vitro was also tested. As shown in FIG. 7B (lanes 1–9), HPV11 E1 could cooperate with HPV16 E2 in supporting dose responsive in vitro replication of the HPV11 ori. (These proteins also functioned in replication of the HPV16 origin, but less efficiently than the HPV11 ori; data not shown). The E2N-WP15 peptide inhibited HPV16 E2/HPV11 E1 dependent replication of the HPV11 origin with approximately the same effectiveness as its inhibition of HPV16 E1/E2 mediated in vitro replication (FIG. 7B, lanes 11–16). The E39A HPV16 E2 mutant had only a slight effect on replication in these assays (lanes 17–19). Thus, the effects of inhibitory peptides on in vitro replication mirrors those observed in E1–E2 interaction assays.

The Dynamics of E1-E2 Interaction

Alanine substitutions. In order to discern the effect of each residue on the ability of the peptide to inhibit HPV-16 E1-E2 interaction, substitution with alanine at each position of the 15-amino acid inhibitory peptide was performed. Alanine scanning mutagenesis generates a small and systematic set of mutant peptides whose inhibitory activity can be readily tested using an in vitro competition binding assay (Cunningham et al., *Science*, 244:1081, 1989). Alanine substitution does not impose new structural effects related to hydrogen bonding, unusual hydrophobicity, or steric bulk, and it is expected to cause minimal perturbation of secondary structure; alanine is compatible with all secondary structures in both buried and solvent-exposed positions (Abroi et al., *J. Virology*, 70(9):6169, 1996; Cunningham et al., *Science*, 244: 1081, 1989; Rose et al., *Science*, 229:834, 1985; Klapper et al., *Biochem Biophys Res Communic*, 78(3):1018, 1977; Chothia et al., *J. Molecu Biol*, 105(1):1, 1976). Also, in contrast to amino acid deletions, substitution with alanine preserves the original spacing of residues. Thus, alanine scanning is a useful technique for isolating the effect of one amino acid within the context of an existing peptide or protein structure.

Little is known about the ordered assembly of the papillomavirus E1 and E2 proteins at the origin of replication, and the formation of the replication initiation complex. Two types of BPV E1-E2-ori complexes have been observed. One complex contains both BPV E1 and E2 (22, 34); the other complex contains only E1, which forms an oligomeric ring around the DNA (33). Although this latter complex can form at high E1 concentrations in the absence of E2 (22, 34), E2 stimulates assembly of the oligomeric E1 complex.

Figure 9:
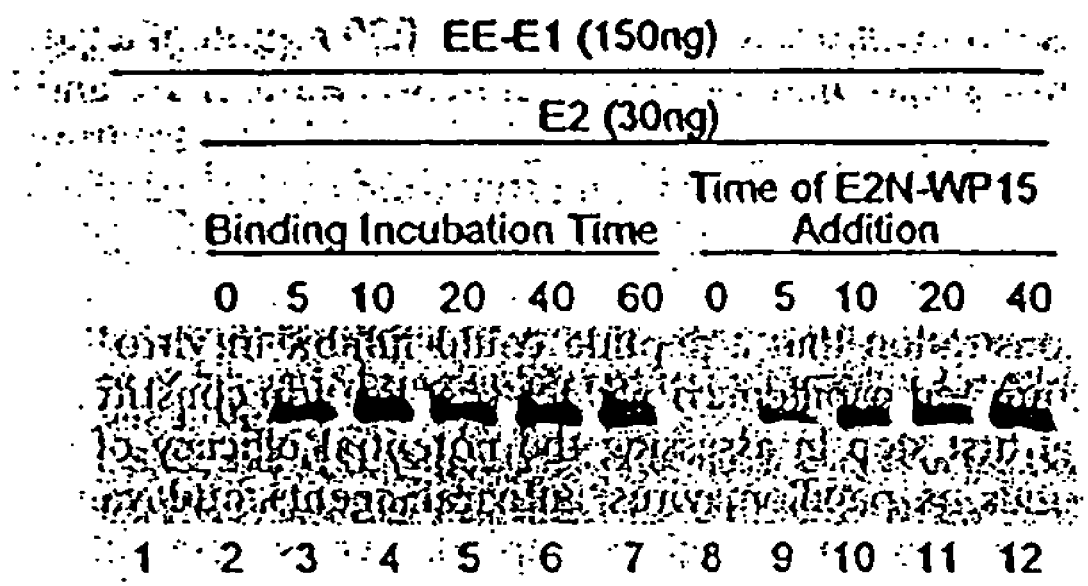
FIG. 9. Kinetics of interaction between HPV16 EE-E1 and E2 in the binding assay in vitro. In vitro E1–E2 binding assays were carried out for the indicated times (lanes 2–7), and E1–E2 complexes were determined by immunoprecipitation using anti-EE monoclonal antibody, followed by Western blot using antiserum to the C-terminus of HPV16 E2. In parallel reactions, E2N-WP15 peptide (50 μM final concentration) was added to the E1–E2 binding reaction at the indicated times (lanes 8–12), and reactions were continued through termination at 60 minutes.
Figure 11:
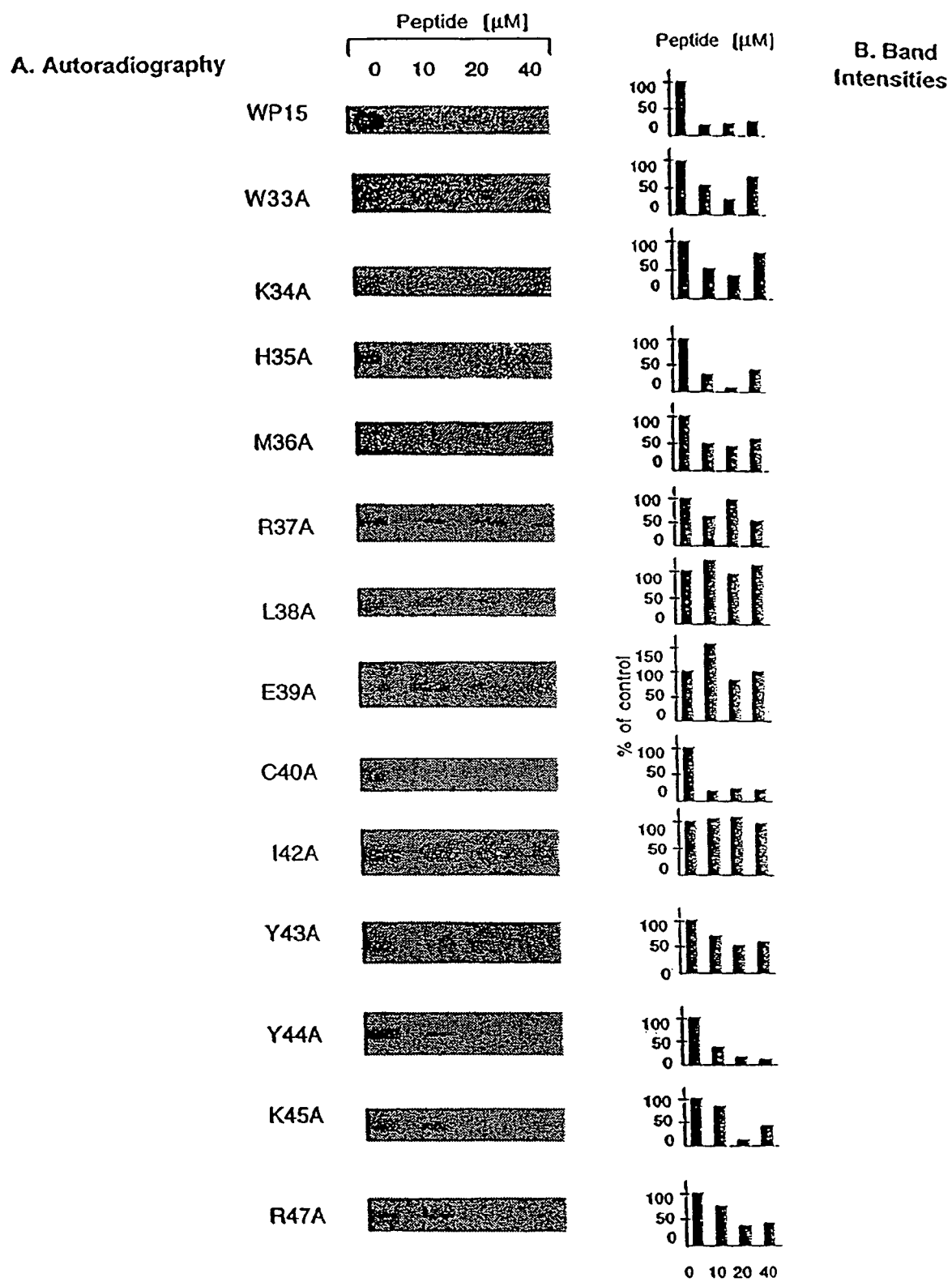
FIG. 11. In vitro inhibition of HPV-16 E1–E2 interaction by alanine-scanning mutant E2 peptides. Binding assays were performed in the presence of 0, 10, 20 or 40 μM peptide. Bound E2 was detected by Western Analysis. (A) Autoradiography data. (B) Intensities of bands were determined by NIH Image Program. For each peptide, the positive control (binding assay in the absence of peptide) was standardized to 100% E2 binding.

As a preliminary step in examining the assembly of replication factors in HPV16 DNA replication, we performed experiments to determine the timing of E1-E2 complex formation. As shown in FIG. 9, HPV16 E1-E2 complexes form rapidly; the binding reaction was 50% complete after approximately 3 minutes, and this binding reached a saturated steady state within 10 minutes (lanes 2–7). We also sought to utilize the E2N-WP15 peptide to study the E1-E2 binding reaction itself by adding peptide (50 µM final concentration) at various times after starting the E1-E2 binding reaction. Addition of peptide at 5 minutes resulted in significant inhibition of subsequent E1–E2 interaction, but addition of peptide at or after 10 minutes had only a minimal effect on the stability of this E1-E2 interaction. We interpret this to mean that complex formation between HPV16 E1 and E2 is rapid, and that the E2N-WP15 inhibits formation of this complex, but has no effect upon the E1-E2 complex in the binding reaction after its formation.

Testing of Tat- and Antennapedia-WP15 Fusion Peptides for Inhibition of E1–E2 Interaction Rationale. Although the full-length HPV-16 E2 protein and its various mutant forms have been tested in vivo for both transcriptional activation and transient replication activity, analogous studies of the WP15 E2 peptide have not been attempted. The characterization of the efficacy and activity of WP15 in vivo is an important goal; however, efficient and reliable introduction of peptides into mammalian cells is technically difficult.

Figure 13:
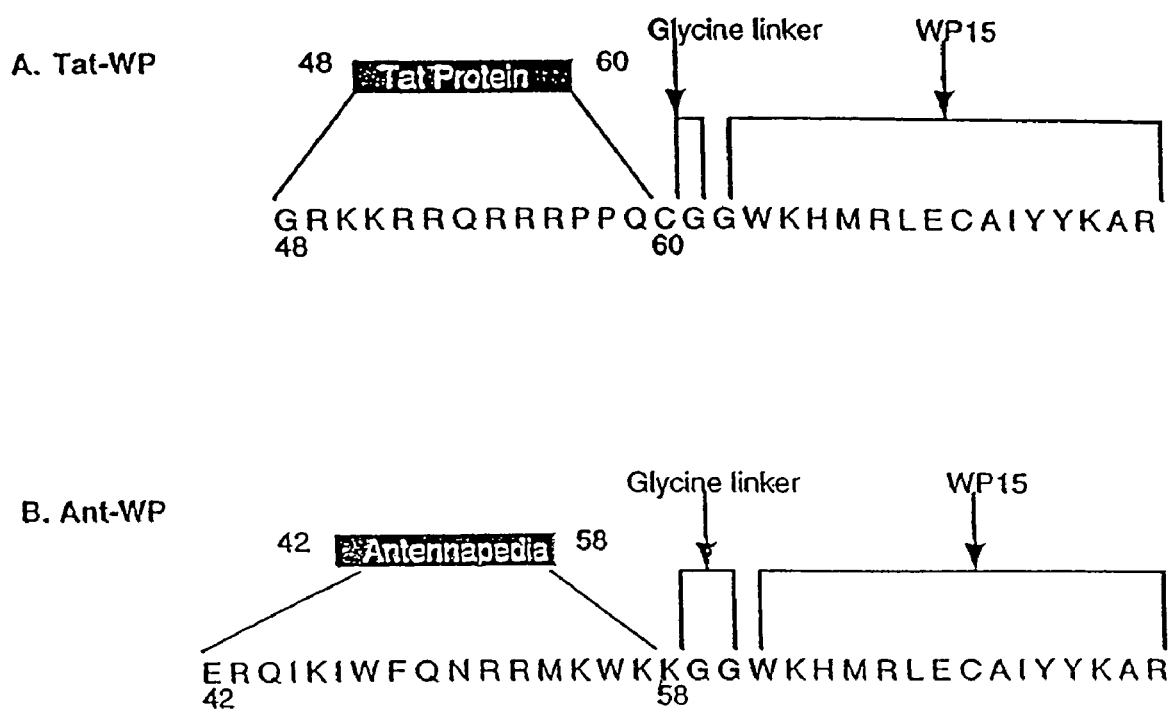
FIG. 13. Amino acid sequence of HPV-16 E2 fusion peptides. (A) A fusion peptide containing thirteen amino acids derived from the basic translocating domain of the Tat protein (aa48–60 Y, followed by WF115 was synthesized. These moieties were separated by a Gly-Gly linker. This peptide is referred to as HTat-WP". (B) Another fusion peptide containing 17amino acids derived from the third homeodomain of Antennapedia(aa42–58) protein, followed by the WP15 (Ant-WP) was tested for inhibition of E1–E2 interaction.

WP15 fusion peptides that contained portions of either the HIV Tat or *Drosophila* Antennapedia protein (Ant) were designed and synthesized (FIG. 13). Small peptides derived from both Tat and Ant have been shown to translocate through mammalian cell plasma membranes and localize in the nucleus. It has been demonstrated that peptides chemically coupled to Tat become functionally internalized into the nuclei of several mammalian cell lines (Vives et al., *JBC*, 272:16010–17, 1997). Similarly, a 16-amino acid polypeptide derived from the third helix of Antennapedia translocates into the nucleus in an energy-independent mechanism (Derossi et al., *J. Biol. Chem*, 269:10444, 1994; Schurze-Redelmeier et al., *J. of Immunology*, 157:650, 1996; Bonfanti et al., *Cancer Research*, 57:1442, 1997).

As a pre-requisite for testing the peptides for inhibition of papillomavirus DNA replication in vivo, fusion peptides were first tested for their ability to inhibit HPV-16 E1-E2 interaction in vitro.

Figure 14:
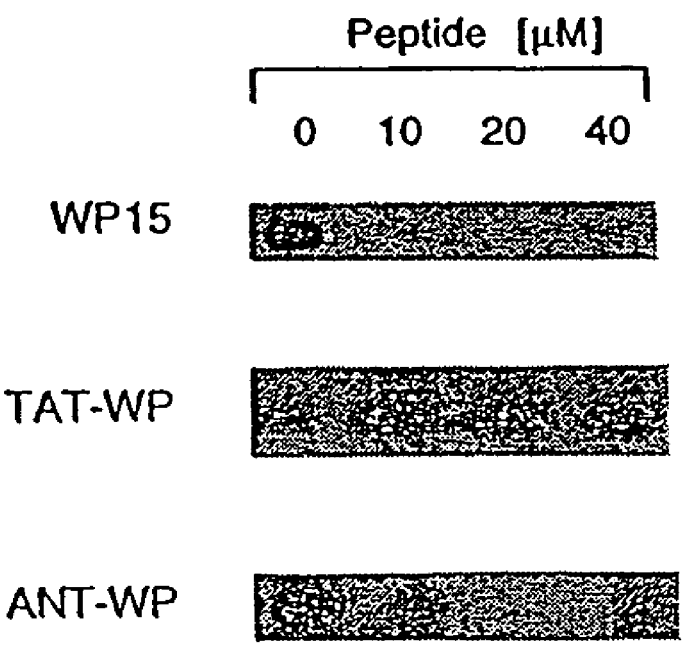
FIG. 14. In vitro inhibition of HPV-16 E1–E2 interaction by Tat- and Ant-WP fusion peptides. Assays were performed in the presence of 0, 10, 20, or 40 μM peptide. Western Analysis was performed and bands were detected by E2-antibody. (A) Autoradiography data. (B) Intensities of bands were determined by NIH Image Program. For each peptide, the positive control (E1–E2 binding in the absence of peptide) was normalized to 100% E2 binding.
Figure 14:
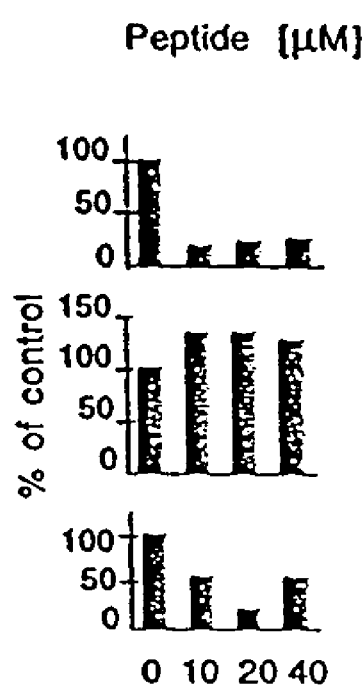

Antennapedia fusion peptide retains the original inhibitory activity of WP15. A second membrane-translocating peptide, Antennapedia protein (Ant) was also linked to the wild-type peptide and tested in the in vitro inhibition of E1-E2 binding assay. The Ant-WP peptide inhibited HPV-16 E1-E2 interaction with levels comparable to that of wild-type peptide (FIG. 14). Based upon the above results, it would be expected that E39A would also inhibit HPV replication in vitro.

Tat fusion peptide interferes with inhibitory activity of wild-type peptide. The first peptide tested was derived from the HIV-I Tat basic protein domain. This fusion moiety was tested in the in vitro inhibition of E1-E2 binding assay to determine whether or not linkage to the translocating peptide affected the activity of the wild-type inhibitory peptide. E1-E2 complex formation was not inhibited in the presence of 10 µM, 20 µM, and 40 µM of Tat-WP, suggesting that linkage to the Tat peptide, completely disrupted the inhibitory activity of the wild-type peptide (FIG. 14).

DISCUSSION

The papillomavirus E1 and E2 proteins carry out the critical step necessary for viral DNA replication: assembly of the replication initiation complex at the origin of replication. This process requires specific interaction of the E2 amino terminus with the E1 protein. *Papillomavirus* replication is otherwise dependent on host cell polymerases and other components of the host cell replication machinery.

We have mapped a number of viral DNA replication associated activities within the HPV16 µl protein (45). The E2 interaction domain of HPV16 µl resides within the carboxy-terminal 223 amino acids (aa421–647), a region that also includes the ATP binding domain. This region is also capable of interacting with other E1 molecules in two-hybrid assays (46). Many missense mutations within this domain of HPV16 E1 simultaneously disrupt multiple E1 activities, including transient replication, E1-E1 association, formation of E1-E2 complexes, ATPase activity, and the ability of E1 to interact with cellular proteins in two-hybrid assays. The pleiotropic effects of many of these HPV16 E1 mutations have led us to speculate that such E1 functions are tightly clustered or functionally interdependent (46).

The initial deletion mapping studies of the BPV1 E2 amino terminus identified domains necessary for transcriptional activation and viral DNA replication (24, 42), but failed to discriminate between these two E2 functions. Non-overlapping deletions within the conserved amino terminus of BPV E2 (e.g. aa1–15, aa92–161, and aa195–282) disrupted both transcriptional activation and replication functions. These results implied either that the E2 transcriptional activation and replication functions co-exist within an extended domain of the amino terminus, or that such deletion mutations caused concurrent disruption of multiple functional moieties within the amino terminus.

More recent studies of the HPV16 E2 and BPV1 E2 amino terminal domains that employed alanine substitution mutagenesis successfully separated the E2 amino terminal replication and transcriptional activation functions. Mutation of the conserved glutamic acid residue at position 39 of HPV16 E2 to alanine specifically abrogates its ability to stimulate transient papillomavirus replication. This mutant no longer interacts with E1, but is proficient for transcriptional activation. Alternatively, substitution of alanine for the conserved isoleucine at position 73 of HPV16 E2 abrogates transcriptional activation, but has no effect on E1 interaction and DNA replication (31). Similar directed mutagenesis studies have extended these results to BPV E2 (1, 6, 7, 10). A genetic screen based on BPV E2 transcriptional activation in yeast has identified additional E2 mutants that have lost either or both of these functions (6, 13).

Such studies have provided convincing evidence that the papillomavirus E2 amino terminus is composed of at least two separable functional domains: one domain defined by isoleucine 73 that is required for transcriptional activation, and a separate domain defined by the glutamic acid residue at position 39 that is required for E1 interaction and replication. In this sense, it is notable that the BPV E2 deletion mutants mentioned above that disrupted both transcriptional activation and replication overlap neither the E39 nor 173 domain. Indeed, even missense mutations scattered throughout the first 200 amino acids of E2 are capable of abrogating either or both functions (1, 6, 13, 31, 42). Thus, although the transcriptional activation and replication functions of the E2 amino terminus are functionally independent, the domains required for these respective functions do not necessarily retain their functional integrity when removed from their normal context. Furthermore, in our mapping studies of HPV16 E2, we defined a domain encompassing amino acids 1–90 as the smallest domain capable of interaction with HPV16 µl in two hybrid assays (45). For these reasons, it was uncertain whether a peptide derived from the E39 region of HPV16 E2 would be capable of competing with intact E2 proteins for specific interaction with the HPV16 E1 carboxy terminus. In this study, we demonstrate that a fifteen amino acid peptide derived from the amino terminus of HPV16 E2 and centered upon E39 can inhibit both HPV16 E1-E2 interaction and papillomavirus replication in vitro. This inhibition is specific, since an equivalent peptide containing an alanine substitution at position 39 had minimal inhibitory activity in both assays. The ability of this peptide to act as a competitive inhibitor of in vitro E1-E2 interaction suggests that a specific E1 recognition activity is contained within a relatively small part of the E2 amino terminus and that this domain is able to adopt a conformation suitable for occupancy of a critical E2 binding site of E1.

The E1-E2 interaction and peptide inhibition experiments presented here indicate functional conservation in E1-E2 recognition and interaction between the E1 and E2 proteins of HPV11 and HPV16. The E39 residue of E2 seems to be a conserved functional component of E1-E2 interaction among these proteins, since this residue is required for interaction between HPV16 E1 and E2, as well as HPV1 E1 and HPV16 E2. E39 is also critical for the replication function of BPV-1 E2 (10). Our peptide inhibition experiments have reiterated the importance of this residue in both HPV16 and HPV11 E1-E2 interaction and replication, since E2N-WP15 disrupted interaction between all combinations of HPV16 and HPV11 E1 and E2 proteins. The lack of interaction we observed between HPV11 E1 and HPV16 E2 in binding assays is consistent with the inability of these proteins to support transient replication when transfected into 293 cells (47). HPV16 E1 seems to be particularly selective in selection of its E2 partner, as compared to HPV11 E1, which can cooperate functionally in replication assays with the E2 proteins of HPV6, HPV11, HPV16, or HPV18 (9, 38). Experiments using HPV11 and HPV16 chimeric E1 proteins have identified the carboxyl-terminal 284 amino acids of HPV16 E1 as the domain that mediates selective binding of HPV16 E1 to HPV16 E2 (47). This selectivity has been attributed to steric interference within this domain of HPV16 E1 that somehow prevents HPV11 E2 binding. Testing the ability of an extended set of peptides derived from the E39 region of a variety of E2 proteins to inhibit interaction between other E1 and E2 proteins may provide greater insight into the exact nature of this selectivity and thus allow an estimation of the spectrum of HPV subtypes against which an individual peptide or small molecule might be effective.

We also used the E2N-WP15 peptide to examine early events in formation of E1-E2 complexes and initiation of viral DNA replication. Formation of the HPV16 E1-E2 complex occurred quickly, within 10 minutes, under the conditions of the in vitro E1-E2 interaction assay.

Demonstration that a peptide could inhibit in vitro E1-E2 interaction and papillomavirus DNA replication constitutes an essential first step in assessing the potential efficacy of small compounds as papillomavirus antiviral agents and validates this approach to the design of papillomavirus antiviral compounds.

REFERENCES

1. Abroi, A., R. Kurg, and M. Ustav. 1996. Transcriptional and replicational activation functions in the papillomavirus type 1 E2 protein are encoded by different structural determinants. J. Virol. 70: 6169–6179.

2. Androphy, E. J., D. R. Lowy, J. T. Schiller. 1987. Bovine papillomavirus E2 trans-activating gene product binds to specific sites in papillomavirus DNA. Nature 325: 70–73.

3. Blitz, I. L. and L. A. Laimins. 1991. The 68-kilodalton E1 protein of bovine papilloavirus is a DNA binding phosphoprotein which associates with the E2 transcriptional activator in vitro. J. Virol. 65: 649–656.

4. Bonne-Andrea, C., S. Santucci, P. Clertant, and F. Tillier. 1995. Bovine papillomavirus E1 protein binds specifically DNA polymerase alpha but replication protein A. J. Virol. 69: 2341–2350.

5. Bonne-Andrea, C., S. Santucci, and P. Clemtant. 1995. Bovine papillomavirus E1 protein can, by itself, efficiently drive multiple rounds of DNA synthesis in vitro. J. Virol. 69: 3201–3205.

6. Breiding, D. E., M. J. Grossel, and E. J. Androphy. 1996. Genetic analysis of the bovine papillomavirus E2 transcriptional activation domain. Virology 221: 34–43.

7. Brokaw, J. L., M. Blanco, and A. A. McBride. 1996. Amino acids critical for the functions of the bovine papillomavirus type 1 transactivator. J. Virol. 70: 23–29.

8. Clertant, P. and I. Seif. 1984. A common function for polyoma virus large-T and papillomavirus E1 proteins, Nature 311: 276–279.

9. Delvecchio, A. M., H. Romanczuk, P. M. Howley, and C. C. Baker. 1992. Transient replication of human papillomavirus DNAs. J. Virol. 66: 5949–5958.

10. Ferguson, M. F., and M. R. Botchan. 1996. Genetic analysis of the activation domain of bovine papillomavirus protein E2: its role in transcription and replication. J. Virol. 70: 4193–4199.

11. Gillette, T. G., M. Lusky. and J. A. Boroweic. 1994. Induction of structural changes in the bovine papillomavirus type 1 origin of replication by the viral E1 and E2 proteins. Proc. Natl. Acad. Sci. USA 91: 8846–8850.

12. Gopalakarishan, V. and S. A. Khan. 1994. E1 protein of human papillomavirus type 1a is sufficient for initiation of viral DNA replication. Proc. Natl. Acad. Sci. USA 91: 9597–9601.

13. Grossel, M. J., F. Sverdrup, D. E. Breiding, and E. J. Androphy. 1996. Transcriptional activation function is not required for stimulation of DNA replication by bovinr papillomavirus type 1 E2. J. Virol. 70: 7264–7269.

14. Holt, S. E., G. Schuller, and V. G. Wilson. 1993. DNA binding specificity of the bovine papillomavirus E1 protein is determined by the sequences contained within an 18-base-pair inverted repeat element at the origin of replication. J. Virol. 68: 1094–1102.

15. Holt, S. E. and V. G. Wilson. 1995. Mutational analysis of the 18-base-pair inverted repeat element at the bovine papillomavirus origin of replication: identification of critical sequences for E1 binding and in vivo replication. J. Virol. 69: 6525–6532.

16. Hughes, F. J., and M. A. Romanos. 1993. E1 protein of human papillomavirus is a DNA helicase/ATPase. Nucleic Acids Res. 21: 5817–5823.

17. Jenkins, O., D. Earnshaw, G. Sarginson, A. Delvecchio, J. Tsai, H. Kallender, B. Amegadzie, and M. Browne. 1996. Characterization of the helicase and ATPase activity of human papillomavirus type 6b E1 protein. J. Gen. Virol. 77 (Part 8): 1805–1809.

18. Kuo, S.-R., J.-S. Liu, T. R. Broker, and L. T. Chow. 1994. Cell-free replication of human papillomavirus DNA with homologous viral E1 and E2 proteins and human cell extracts. J. Biol. Chem. 269: 24058–24065.

19. Li, R. and M. Botchan. 1994. Acidic transcription factors alleviate nucleosome-mediated repression of DNA replication of bovine papillomavirus type 1. Proc. Natl. Acad. Sci. USA 91: 7051–7055.

20. Liu, J.-S., S.-R. Kuo, T. R. Broker, and L. T. Chow. 1995. The functions of human papillomavirus type 11 E1, E2, and E2C proteins in cell-free DNA replication. J. Biol. Chem. 270: 27283–27291.

21. Lusky, M., J. Hurwitz, and Y.-S. Seo. 1993. Cooperative assembly of the bovine papilloma virus E1 and E2 proteins on the replication origin requires an intact E2 binding site. J. Biol. Chem. 268: 15795–15803.

22. Lusky, M., J. Hurwitz, and Y.-S. Seo. 1994. The bovine papillomavirus E2 protein modulates the assembly of but is not stably maintained in a replication-competent multimeric E1-replication origin complex. Proc. Natl. Acad. Sci. USA 91: 8895–8899.

23. Mansky, K. C., A. Batiza, and P. F. Lambert. 1997. Bovine papillomavirus type 1 E1 and simian virus 40 large T antigen share regions of sequence similarity required for multiple functions. J. Virol. 71: 7600–7608.

24. McBride, A. A., R. Schlegel, and P. M. Howley. 1988. The carboxy-terminal domain shared by the bovine papillomavirus E2 transactivator and repressor proteins contains a specific DNA binding activity. EMBO J. 7: 533–539.

25. McBride, A. A., J. C. Byrne, and P. M. Howley. 1989. E2 polypeptides encoded by bovine papillomavirus type 1 form dimers through the common carboxyl-terminal domain: transactivation is mediated by the conserved amino-terminal domain. Pros. Natl. Acad. Sci. USA 86: 510–514.

26. Mendoza, R., L. Gandhi, and M. R. Botchan. 1995. E1 recognition sequences in the bovine papillomavirus type 1 origin of replication: interaction between half sites of the inverted repeats. J. Virol. 69: 3789–3798.

27. Melendy. T., J. Sedman, and A. Stenlund. 1995. Cellular factors required for papillomavirus DNA replication. J. Virol. 69: 7857–7867.

28. Mohr, I., J. R. Clark, S. Sun, E. J. Androphy, P. MacPherson, and M. R. Botchan. 1990. Targeting the E1 replication protein to the papillomavirus origin of replication by complex formation with the E2 transactivator. Science 250: 1694–1699.

29. MŸller, F., Y.-S. Seo, and J. Hurwitz. 1994. Replication of bovine papillomavirus type 1 origin-containing DNA in crude extracts and with purified proteins. J. Biol. Chem. 269: 17086–17094.

30. Park, P., W. Copeland, L. Yang, T. Wang, M. R. Botchan, and I. J. Mohr. 1994. The cellular DNA polymerase a-primase is required for papillomavirus DNA replication and associates with the viral E1 helicase. Proc. Natl. Acad. Sci. USA 91: 8700–8704.

31. Sakai, H., T. Yasugi, J. D. Benson, J. J. Dowhanick, and P. M. Howley. 1996. Targeted mutagenesis of the human papillomavirus type 16 E2 transactivation domain reveals separable transcriptional activation and DNA replication functions. J. Virol. 70: 1602–1611.

32. Sedman, J. and A. Stenlund. 1995. Cooperative interaction between the initiator E1 and the transcriptional activator E2 is required for replication of bovine papillomavirus in vivo and in vitro. EMBO J. 14: 6218–6228.

33. Sedman, J. and A. Stenlund. 1996. The initiator protein E1 binds to the bovine papillomavirus origin of replication as a trimeric ring-like structure. EMBO J. 15: 5085–5092.

34. Sedman, T., Sedman, J. and A. Stenlund. 1997. Binding of the E1 and E2 proteins to the origin of replication of bovine papillomavirus. J. Virol. 71: 2887–2896.

35. Seo, Y.-S., F. MŸller, M. Lusky, E. Gibbs, H.-Y. Kim, B. Phillips and J. Hurwitz. 1993. Bovine papilloma virus (BPV)-encoded E2 protein enhances binding of E1 protein to the BPV replication origin. Proc. Natl. Acad. Sci. USA 90: 2865–2869.

36. Seo, Y.-S., F. MŸller, M. Lusky, and J. Hurwitz. 1993. Bovine papillom virus (BPV)-encoded E1 protein contains multiple activities required for BPV DNA replication. Proc. Natl. Acad. Sci. USA 90: 702–706.

37. Sun, S., L. Thorner, M. Lentz, P. MacPherson, and M. Botchan. 1990. Identification of a 68-kilodalton nuclear ATP-binding phosphoprotein encoded by bovine papillomavirus type 1. J. Virol. 64: 5093–5105.

38. Sverdrup, F. and S. A. Khan. 1994. Replication of human papillomavirus (HyPV) DNAs supported by the HPV type 18 E1 and E2 proteins. J. Virol. 68: 505–509.

39. Thorner, L. K., D. A. Lim and M. R. Botchan. 1993. DNA-binding domain of bovine papillomavirus type 1 E1 helicase: structural and functional aspects. J. Virol. 67: 6000–6014.

40. Ustav, M. and A. Stenlund. 1991. Transient replication of BPV-1 requires two viral polypeptides encoded by the E1 and E2 open reading frames. EMBO J. 10: 449–457.

41. Wilson, V. G., and J. Ludes-Meyers. 1991. A bovine papillomavirus E1-related protein binds specifically to bovine papillomavirus DNA. J. Virol. 65: 5314–5322.

42. Winokur, P. L. and A. A. McBride. 1992. Separation of the transcriptional activation and replication functions of the bovine papillomavirus-1 E2 protein. EMBO J. 11: 4111–4118.

43. Yang, L., R. L1, I. J. Mohr, R. Clark, and M. R. Botchan. 1991. Activation of BPV-1 replication in vitro by the transcription factor E2. Nature 353: 628–632.

44. Yang, L., I. Mohr, E. Fouts, D. A. Lim, M. Nohaile, and M. Botchan. 1993. The E1 protein of bovine papillomavirus 1 is an ATP-dependent DNA helicase. Proc. Natl. Acad. Sci. USA 90: 5086–5090.

45. Yasugi, T., J. D. Benson, H. Sakai, M. Vidal, and P. M. Howley. 1997. Mapping and characterization of the interaction domains of the human papillomavirus type 16 E1 and E2 proteins. J. Virol. 71: 891–899.

46. Yasugi, T., M. Vidal, H. Sakai, P. M. Howley, and J. D. Benson. 1997. Two classes of human papillomavirus type 16 E1 mutants suggest pleiotropic conformational constraints affecting E1 multimerization, E2 interaction, and interaction with cellular proteins. J. Virol. 71: 5942–5951.

47. Zou, N., J.-S. Liu, S.-R. Kuo, T. R. Broker, and L. T. Chow. 1998. The carboxyl-terminal region of the human papillomavirus type 16 E1 protein determines E2 protein specificity during DNA replication. J. Virol. 72: 3436–3441.

48. zur Hausen, H. 1991. Viruses in human cancers. Science 254: 1167–1173.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

---

We claim:

1. A peptide comprising a core E2 sequence comprising at least 15 contiguous amino acids of SEQ ID NO: 22, wherein the peptide inhibits the interaction between HPV E1 and E2 proteins, and wherein, in addition to the core E2 sequence, the peptide comprises no more than about 25 contiguous amino acid residues of an HPV E2 protein.

2. The peptide of claim 1, consisting essentially of the amino acid sequence set forth in SEQ ID NO: 22 or 31.

3. The peptide of claim 1, comprising the amino acid sequence set forth in SEQ ID NO: 22 or 31.

4. The peptide of claim 3, consisting of the amino acid sequence set forth in SEQ ID NO: 22 or 31.

5. The peptide of claim 1, further linked to another moiety.

6. The peptide of claim 5, wherein the other moiety is an internalizing peptide, an accessory peptide or a transport moiety.

7. The peptide of claim 6, wherein the other moiety comprises amino acids 42–58 of the *Drosophila* Antennapedia protein (Ant).

8. The peptide of claim 1, which is a peptidomimetic.

9. The peptide of claim 8, wherein at least one amino acid is a D stereoisomer.

10. The peptide of claim 9, wherein every amino acid is a D stereoisomer.

11. A peptide analog of the peptide of claim 1, wherein at least one amino acid is reversed.

12. The peptide analog of claim 11, wherein the amino acid that is reversed is a D stereoisomer.

13. The peptide analog of claim 11, wherein every amino acid is reversed.

14. The peptide of analog of claim 13, wherein every amino acid is a D stereoisomer.

15. The peptide of claim 1, consisting essentially of at least 15 contiguous amino acids of SEQ ID NO: 22.

16. The peptide of claim 1, wherein, in addition to the core E2 sequence, the peptide comprises no more than 10–15 contiguous amino acid residues of an HPV E2 protein.

17. The peptide of claim 1, wherein, in addition to the core E2 sequence, the peptide comprises no more than 6 contiguous amino acid residues of an HPV E2 protein.

18. The peptide of claim 1, wherein the core E2 sequence consists essentially of the amino acid sequence set forth in SEQ ID NO: 22 or 31.

19. The peptide of claim 1, wherein the core E2 sequence consists of the amino acid sequence set forth in SEQ ID NO: 22 or 31.

20. The peptide of claim 1, consisting essentially of a core E2 sequence consisting of at least 15 contiguous amino acids of SEQ ID NO: 22, wherein the peptide inhibits the interaction between HPV E1 and E2 proteins, and wherein, in addition to the core E2 sequence, the peptide comprises no more than about 25 contiguous amino acid residues of an HPV E2 protein.

* * * * *